(12) United States Patent
Shen et al.

(10) Patent No.: US 11,248,013 B2
(45) Date of Patent: Feb. 15, 2022

(54) TRICYCLIC INHIBITORS OF POLY(ADP-RIBOSE)POLYMERASE

(71) Applicant: Rakovina Therapeutics Inc., Vancouver (CA)

(72) Inventors: Wang Shen, San Mateo, CA (US); Jack Maung, Daly City, CA (US); Aimin Zhang, Castro Valley, CA (US); Xiaoling Zheng, Fremont, CA (US)

(73) Assignee: Rakovina Therapeutics Inc., Vancouver (CA)

( * ) Notice: Subject to any disclaimer, the term of this patent is extended or adjusted under 35 U.S.C. 154(b) by 0 days.

(21) Appl. No.: 16/666,307

(22) Filed: Oct. 28, 2019

(65) Prior Publication Data

US 2020/0299315 A1 Sep. 24, 2020

Related U.S. Application Data

(63) Continuation of application No. 15/624,201, filed on Jun. 15, 2017, now abandoned, which is a continuation of application No. 15/089,131, filed on Apr. 1, 2016, now abandoned, which is a continuation of application No. 14/122,983, filed as application No. PCT/US2012/040304 on May 31, 2012, now abandoned.

(60) Provisional application No. 61/491,851, filed on May 31, 2011.

(51) Int. Cl.
    *C07F 9/6584* (2006.01)
(52) U.S. Cl.
    CPC .................. *C07F 9/6584* (2013.01)
(58) Field of Classification Search
    CPC .................................................... C07F 9/6584
    See application file for complete search history.

(56) References Cited

U.S. PATENT DOCUMENTS

| | | |
|---|---|---|
| 6,284,781 B1 | 9/2001 | Danishefsky |
| 6,288,237 B1 | 9/2001 | Hoefle |
| 7,402,580 B2 | 7/2008 | Seko |
| 2002/0183325 A1 | 12/2002 | Martin |
| 2005/0107358 A1 | 5/2005 | Himmelsbach |
| 2006/0063767 A1 | 3/2006 | Javaid |
| 2008/0161280 A1 | 7/2008 | Gandhi |
| 2008/0269234 A1 | 10/2008 | Gandhi |
| 2014/0221314 A1 | 8/2014 | Shen |
| 2017/0057984 A1 | 3/2017 | Shen |
| 2018/0094010 A1 | 4/2018 | Shen |
| 2020/0299315 A1 | 9/2020 | Shen |

FOREIGN PATENT DOCUMENTS

| | | |
|---|---|---|
| JP | 2006519827 A | 8/2006 |
| JP | 2008510783 A | 4/2008 |
| JP | 2009544611 A | 12/2009 |
| JP | 2011500655 A | 1/2011 |
| WO | 200044777 A1 | 8/2000 |
| WO | 200050032 A1 | 8/2000 |
| WO | 200061186 A1 | 10/2000 |
| WO | 200236576 A1 | 5/2002 |
| WO | 2003070707 A1 | 8/2003 |
| WO | 2003093261 A1 | 11/2003 |
| WO | 2004080976 A1 | 9/2004 |
| WO | 2006021801 A1 | 3/2006 |
| WO | 2007045877 A1 | 4/2007 |
| WO | 2007138351 A2 | 12/2007 |
| WO | 2008010985 A2 | 1/2008 |
| WO | 2008010985 A3 | 4/2008 |
| WO | 2007138351 A3 | 8/2008 |
| WO | 2008114023 A2 | 9/2008 |
| WO | 2008122810 A1 | 10/2008 |
| WO | 2008114023 A3 | 11/2008 |
| WO | 2009004356 A1 | 1/2009 |
| WO | 2009034326 A1 | 3/2009 |
| WO | 2009050469 A1 | 4/2009 |
| WO | 2009063244 A1 | 5/2009 |
| WO | 2009093032 A1 | 7/2009 |
| WO | 2011002523 A1 | 1/2011 |

OTHER PUBLICATIONS

Alli, E. et al. (Apr. 15, 2009, e-pub. Apr. 7, 2009). "Defective Repair of Oxidative DNA Damage in Triple-Negative Breast Cancer Confers Sensitivity to Inhibition of Poly(ADP-Ribose) Polymerase," Cancer Res. 69(8):3589-3596.

Amé, J.-C. et al. (2004). "The PARP Superfamily," BioEssays 26:882-893.

Bartha, E. et al. (Sep. 2008). "Effect of L-2286, A Poly(ADP-Ribose)Polymerase Inhibitor and Enalapril on Myocardial Remodeling and Heart Failure," J. Cardiovasc. Pharmacol. 52(3):253-261.

Ben-Hur, E. et al. (1984). Inhibitors of Poly (ADP-ribose) Synthesis Enhance Radiation Response by Differentially Affecting Repair of potentially Lethal Versus Sublethal Damage,: Br. J. Cancer 49(Suppl. VI):39-42.

(Continued)

*Primary Examiner* — Emily A Bernhardt

(74) *Attorney, Agent, or Firm* — Morrison & Foerster LLP

(57) ABSTRACT

The invention provides for compositions comprising phosphorous containing tricyclic compounds, including phthalazin-1(2H)-one derivatives. The compounds are potent inhibitors of the enzyme poly(ADP-ribose)polymerase (PARP), particularly PARP-1 and potentially PARP-2. The also show good cellular activity in inhibiting poly(ADP-ribose) oligomer formation. The compounds may be useful as mono-therapy or in combination with other therapeutic agents in the treatment conditions where PARP is implicated, such as cancer, inflammatory diseases and ischemic conditions. Thus, also provided are methods for the treatment of a condition where PARP is implicated comprising administering to an effective amount of a compound of the invention to an individual in need thereof.

23 Claims, No Drawings

(56) References Cited

OTHER PUBLICATIONS

Bowes, J. et al. (Oct. 23, 1998). "Reduction of Myocardial Reperfusion Injury by an Inhibitor of Poly (ADP-Ribose) Synthetase in the Pig," Eur. J. Pharmacol. 359:143-150.
Brower, V. (Oct. 1999). "Tumor Angiogenesis-New Drugs on the Block," Nature Biotechnology 17:963-968.
Bryant, H.E. et al. (Apr. 14, 2005)."Specific Killing of BRCA2-Deficient Tumours With Inhibitors of Poly(ADP-Ribose) polymerase" Nature 434(7035):913-917. With Correction Page and Addendum.
Bundscherer, A. et al. (Sep. 2009). "Targeting The Tumor Stroma With Peroxisome Proliferator Activated Receptor (PPAR) Agonists," Anti-Cancer Agents in Medicinal Chemistry 9(7):815-821.
Bürkle, A. et al. (Jul. 2005). "Ageing and PARP," Pharmacological Research 52(1):93-99.
Calabrese, C.R. et al. (Jan. 7, 2004). "Anticancer Chemosensitization and Radiosensitization by The Novel Poly(ADP-Ribose) Polymerase-1 Inhibitor AG14361," J. Natl. Cancer Inst. 96(1):56-67.
Cancer Drug Design and Discovery, (2008) Neidle, Stephen,ed. (Elsevier/Academic Press), pp. 427-431.
Cantoni, O. et al. (Oct. 30, 1989). "Hydrogen Peroxide Insult in Cultured Mammalian Cells: Relationships Between DNA Single-Strand Breakage, Poly(ADP-Ribose) Metabolism and Cell Killing," Biochim. Biophys. Acta 1014 (1):1-7.
Chakraborty, I. et al. (Apr. 1996). "Developmental Expression of the Cyclo-Oxygenase-1 and Cyclo-Oxygenase-2 Genes in the Peri-Implantation Mouse Uterus and Their Differential Regulation by the Blastocyst and Ovarian Steroids," J. Mol. Endocrinol. 16(2):107-122.
Chalmers, A.J. (Feb. 2004). "Poly(ADP-Ribose) Polymerase-1 and Ionizing Radiation: Sensor, Signaller and Therapeutic Target," Clin. Oncol. 16(1):29-39.
Chappuis, P.O. et al. (2002). "Risk Assessment & Genetic Testing," Chapter 2 in Ovarian Cancer, Stack, MS et al. (eds), Kluwer Academic Publisher, Boston Cancer Treat. Res. 107:29-59.
Chen, G. et al. (1993). "Reversal of Acquired Cisplatin Resistance by Nicotinamide In Vitro and In Vivo," Cancer Chemother. Pharmacol 33(2):157-162.
Chiarugi, V. et al. (Dec. 1998). "Cox-2, iNOS and p53 as Play-Makers of Tumor Angiogenesis," Intl. J. Mol. Med. 2(6):715-719.
Cosi, C. et al. (Sep. 1, 1994). "Poly(ADP-Ribose) Polymerase: Early Involvement in Glutamate-Induced Neurotoxicity in Cultured Cerebellar Granule Cells," J. Neurosci. Res. 39(1):38-46.
Cuzzocrea, S. (Jul. 2005). "Shock, Inflammation and PARP," Pharmacological Research 52(1):72-82.
Daniel, R.A. (Feb. 15, 2009, e-pub. Jan. 27, 2009). "Inhibition of Poly(ADP-Ribose) Polymerase-1 Enhances Temozolomide andTopotecan Activity against Childhood Neuroblastoma," Clin. Cancer Res. 15(4):1241-1249.
Dedes, K.J. et al. (Oct. 13, 2010). "PTEN Deficiency in Endometrioid Endometrial Adenocarcinomas Predicts Sensitivity to PARP Inhibitors," Sci. Transl. Med. 2(53):53ra75. pp. 1-8.
Delaney, C.A. et al. (Jul. 2000). "Potentiation of Temozolomide and Topotecan Growth Inhibition and Cytotoxicity by Novel Poly(adenosine Diphosphoribose) Polymerase Inhibitors in a Panel of Human Tumor Cell Lines," Clin. Cancer Res. 6:2860-2867.
Devalaraja-Narashimha, K. et al. (Jul. 2005). "Poly(ADP-ribose) Polymerase-Mediated Cell Injury in Acute Renal Failure," Pharmacological Research 52(1):44-59.
Donawho, C.K. et al. (May 1, 2007). "ABT-888, an OrallyActive Poly(ADP-Ribose) Polymerase Inhibitor that Potentiates DNA-Damaging Agents in Preclinical Tumor Models," Clin. Cancer Res. 13(9):2728-2737.
Drew, Y. et al. (Feb. 16, 2011). "Therapeutic Potential of Poly(ADP-ribose) Polymerase Inhibitor AG014699 in Human Cancers With Mutated or Methylated BRCA1 or BRCA2," J. Natl. Cancer Inst. 103(4):334-346.
Dunne, K.S. et al. (Dec. 23, 2005, e-pub. Nov. 24, 2005). "Diastereoselective Ring-Closing Metathesis: Synthesis of P-stereogenic Phosphinates From Prochiral Phosphinic Acid Derivatives," Org. Chem. 70 (26): 10803-10809.
D'Adda Di Fagagna, F. et al.(Sep. 1999). "Functions of Poly(ADP-Ribose) Polymerase in Controlling Telomere Length and Chromosomal Stability," Nature Gen. 23(1):76-80.
Eliel, E.L. et al. (1994). "Chirality in Molecules Devoid of Chrial Centers," Chapter 14 in Stereochemistry of Carbon Compounds, John Wiley & Sons, New York pp. 1119-1190.
Extended European Search Report dated Nov. 27, 2014, for EP Patent Application No. 12792550.1, filed on May 31, 2012, 7 pages.
Farmer, H. et al. (Apr. 14, 2005). "Targeting the DNA Repair Defect in BRCA Mutant Cells as a Therapeutic Strategy," Nature 434(7035):917-920.
Faro, R. et al. (2002). "Myocardial Protection by PJ34, a Novel Potent Poly (ADP-Ribose) Synthetase Inhibitor," Ann. Thorac. Surg. 73:575-581.
Fathallah-Shaykh, H.M. et al. (2000). "Gene Transfer of IFN-γ Into Established Brain Tumors Represses Growth by Antiangiogenesis," J. Immunol. 164:217-222.
Fernandez, L.A. et al. (Feb. 1985). "Neovascularization Produced by Angiotensin II," J. Lab. Clin. Med. 105(2):141-145.
Ferraris, D.V. (2010). "Evolution of Poly(ADP-ribose) Polymerase-1 (PARP-1) Inhibitors. From Concept to Clinic," J. Med. Chem. 53(12):4561-4584.
Final Office Action dated Sep. 28, 2018, for U.S. Appl. No. 15/624,201, filed Jun. 15, 2017, 23 pages.
Gäken, J.A. et al. (Jun. 1996). "Efficient Retroviral Infection of Mammalian Cells Is Blocked by Inhibition of Poly(ADP-Ribose) Polymerase Activity," J. Virology 70(6):3992-4000.
Hall, S.J. et al. (1997). "Gene Therapy '97 the Promise and Reality of Cancer Gene Therapy," Am. J. Hum. Genet. 61:785-789.
Hla, T. et al. (Aug. 1992). "Human Cyclooxygenase-2 cDNA," Proc. Natl. Acad. Sci. USA 89:7384-7388.
Hughes-Davies, L. (Nov. 26, 2003) "EMSY Links the BRCA2 Pathway to Sporadic Breast and Ovarian Cancer," Cell 115:523-535.
International Preliminary Report on Patentability for PCT/US2012/040304 dated Dec. 122, 2013, filed on May 31, 2012, 5 pages.
International Search Report for PCT/US2012/040304 dated Jun. 25, 2012, filed on May 31, 2012, 6 pages.
Jagtap, P. et al. (May 2005). "Poly(ADP-Ribose) Polymerase and the Therapeutic Effects of Its Inhibitors," Nature Review Drug Discovery 4(5):421-440.
Janatová, M. et al. (2003). "Detection of the Most Frequent Mutations in BRCA1 Gene on Polyacrylamide Gels Containing Spreadex Polymer NAB," Neoplasma 50(4):246-250.
Jancarkova, N. et al. (Jan. 2003). "Detection and Occurrence of BRCA 1 Gene Mutation in Patients With Carcinoma of the Breast and Ovary," Ceska Gynekol 68(1):11-16. English Abstract Only.
Japanense Notice of Allowance dated Jun. 23, 2016 for Japanese Patent Application No. 2014-513717 English Translation of Amended Claims only, 24 pages.
Jasin, M. (2002). "Homologous Repair of DNA Damage and Tumorigenesis:The BRCA Connection," Oncogene 21 (58):8981-8993.
Khanna, K.K. (Mar. 2001). "DNA Double-Strand Breaks: Signaling, Repair and the Cancer Connection," Nat. Genet. 27(3):247-254.
Kim, K.J. et al. (Apr. 29, 1993). "Inhibition of Vascular Endothelial Growth Factor-Induced Angiogenesis Suppresses Tumour Growth In Vivo," Nature 362(6423):841-844.
Kufe, D.W. et al. (2000). "Section 17: Principles of Gene Therapy," in Cancer Medicine, 5th Ed. BC Decker, Inc., Hamilton pp. 876-889.
Le Rhun, Y. et al. (Apr. 7, 1988). "Cellular Responses to DNA Damage in the Absence of Poly(ADP-ribose) Polymerase," Biochem. Biophys. Res. Commun. 245(1):1-10.
Li, H. et al. (Aug. 1998). "Adenovirus-Mediated Delivery of a uPA/uPAR Antagonist Suppresses Angiogenesis-Dependent Tumor Growth and Dissemination in Mice," Gene Therapy 5(8):1105-1113.
Li, J.-H. et al. (Jul. 1, 2001). "PARP Inhibitors," Drugs, 4:804-812.
Lord, C.J. et al. (Aug. 2008). "Targeted Therapy for Cancer Using PARP Inhibitors," Current Opinion in Pharmacology, 8:363-369.

(56) References Cited

OTHER PUBLICATIONS

Löser, D.A. et al. (Jun. 2010, e-pub. Jun. 8, 2010). "Sensitization to Radiation and Alkylating Agents by Inhibitors of Poly(ADP-ribose) Polymerase Is Enhanced in Cells Deficient in DNA Double-Strand Break Repair," Mol. Cancer Ther. 9(6):1775-1787.
Maier, V. L. (1971). "Organische Phosphorverbindungen 44 Darstellung und Eigenschaften von Bis-(β-chloräthyl)-phosphinsäure-Derivaten," Helv. Chim. Acta 54(1):275-277. English Abstract Only.
Majima, M. et al. (1997). "Significant Roles of Inducible Cyclooxygenase (COX)-2 in Angiogenesis in Rat Sponge Implants," Jpn. J. Pharmacol. 75:105-114.
McCabe, N. et al. (Sep. 2005). "BRCA2-Deficient CAPAN-1 cells Are Extremely Sensitive to the Inhibition of Poly (ADP-Ribose) Polymerase: An Issue of Potency" Cancer Biology & Therapy 4(9):934-936.
McEllin, B. et al. (Jul. 1, 2010). "PTEN loss Compromises Homologous Recombination Repair in Astrocytes: Implications for GBM Therapy With Temozolomide or PARP Inhibitors," Cancer Res. 70(13):5457-5464.
Mendes-Pereira, A.M. et al. (2009). "Synthetic Lethal Targeting of PTEN Mutant Cells With PARP Inhibitors," EMBO Mol. Med. 1:315-322.
Menear, K.A. et al. (Oct. 23, 2008, e-pub. Sep. 19, 2008). "4-[3-(4-Cyclopropanecarbonylpiperazine-1-Carbonyl)-4-Fluorobenzyl]-2H-Phthalazin-1-One: A Novel Bioavailable Inhibitor of Poly(ADP-Ribose) Polymerase-1," J. Med. Chem. 51(20):6581-6591.
Miknyoczki, S.J. et al. (Apr. 2003). "Chemopotentiation of Temozolomide, Irinotecan, and Cisplatin Activity by CEP-6800, a Poly(ADP-Ribose) Polymerase Inhibitor," Mol. Cancer. Ther. 2(4):371-382.
Neuhausen, S.L. et al. (1997). "Mutation Testing of Early-Onset Breast Cancer Genes BRCA1 and BRCA2," Genet. Test 1(2):75-83.
Non-Final Office Action dated Apr. 30, 2019, for U.S. Appl. No. 15/624,201, filed Jun. 15, 2017.
Non-Final Office Action dated Dec. 15, 2016, for U.S. Appl. No. 15/089,131, filed Apr. 1, 2016, 12 pages.
Non-Final Office Action dated Feb. 2, 2018, for U.S. Appl. No. 15/624,201, filed Jun. 15, 2017.
Non-Final Office Action dated Oct. 2, 2015, for U.S. Appl. No. 14/122,983, filed Apr. 14, 2014, 14 pages.
Pinedo, H.M. et al. (2000). "Translational Research: The Role of VEGF in Tumor Angiogenesis," The Oncologist 5(Suppl. 1):1-2.
Prasad, C.B. et al. (2017, e-pub. Oct. 9, 2017). "Olaparib Modulates DNA Repair Efficiency, Sensitizes Cervical Cancer Cell to Cisplatin and Exhibits Anti-Metastatic Property," Scientific Reports 7:12876, p. 1-15.
Radice, P. (Sep. 2002). "Mutations of BRCA Genes in Hereditary Breast and Ovarian Cancer," J. Exp. Clin. Cancer Res. 21(Suppl. 3):9-12.
Rattan, S.I. et al. (Jun. 15, 1994). "Kinetin Delays the Onset of Ageing Characteristics in Human Fibroblasts," Biochem. Biophys. Res. Comm. 201(2):665-672.
Said, S.I. et al. (May 1996). "Excitotoxicity in the Lung: N-Methyl-D-aspartate-Induced, Nitric Oxide-Dependent, Pulmonary Edema Is Attenuated by Vasoactive Intestinal Peptide and by Inhibitors of Poly(ADP-ribose) Polymerase," Proc. Natl. Acad. Sci. USA 93:4688-4692.
Schlicker, A. et al. (1999). "4-Amino-1,8-Naphthalimide: A Novel Inhibitor of Poly(ADP-Ribose) Polymerase and Radiation Sensitizer," Int. J. Radial Biol. 75(1):91-100.
Seed, M.P. et al. (May 1, 1997). The Inhibition of Colon-26 Adenocarcinoma Development and Angiogenesis by Topical Diclofenac in 2.5% Hyaluronan,: Cancer Res. 57:1625-1629.
Shen, W.H. et al. (Jan. 12, 2007). "Essential Role for Nuclear PTEN in Maintaining Chromosomal Integrity," Cell 128:157-170.
Szabo, C. (Jul. 2005). "Cardioprotective Effects of Poly(ADP-Ribose) Polymerase Inhibition," Pharmacological Research 52(1):34-43.
Szabó, C. (Jul. 2005). "Roles of Poly(ADP-Ribose) Polymerase Activation in the Pathogenesis of Diabetes Mellitus and Its Complications," Pharmacological Research 52(1):60-71.
Szabó, C. et al. (Aug. 1997). "Endothelial Dysfunction in a Rat Model of Endotoxic Shock: Importance of the Activation of Poly (ADP-ribose) Synthetase by Peroxynitrite," J. Clin. Invest. 100(3):723-735.
Szabó, G. et al. (May 2004). "INO-1001 a Novel Poly(ADP-Ribose) Polymerase (PARP) Inhibitor Improves Cardiac and Pulmonary Function After Crystalloid Cardioplegia and Extracorporal Circulation," Shock. 21(5):426-432.
Taiwanese Search Report for Application No. 101119653 dated Jun. 1, 2016, 2 pages.
Tentori, L. et al. (Jul. 2005). "Chemopotentiation by PARP inhibitors in Cancer Therapy," Pharmacological Research 52(1):25-33.
Thiemermann, C. et al. (Jan. 1997). "Inhibition of the Activity of Poly(ADP Ribose) synthetase Reduces Ischemia-Reperfusion Injury in the Heart and Skeletal Muscle," Proc. Natl. Acad. Sci. USA 94:679-683.
Tsujii, M. et al. (May 29, 1998). "Cyclooxygenase Regulates Angiogenesis Induced by Colon Cancer," Cells Cell 93:705-716.
Tutt, A. et al. (Dec. 2002). "The Relationship Between the Roles of BRCA Genes in DNA Repair and Cancer Predisposition," Trends Mol. Med. 8(12):571-576.
Tutt, A. et al. (Jul. 24, 2010). "Oral Poly(ADP-Ribose) Polymerase Inhibitor Olaparib in Patients With BRCA1 or BRCA2 Mutations and Advanced Breast Cancer: A Proof-Of-Concept Trial," The Lancet 376(9737):235-244.
Underhill, C. et al. (Feb. 2011). "A Review of PARP Inhibitors: From Bench to Bedside," Annals of Oncology Advance Access 22:268-279.
Virág, L. (Jul. 2005). "Poly(ADP-Ribosyl)ation in Asthma and Other Lung Diseases," Pharmacological Research 52(1):83-92.
Wood, R.D. et al. (Feb. 16, 2001). "Human DNA Repair Genes," Science 291:1284-1289.
Written Opinion Search Report for PCT/US2012/040304, dated Jun. 25, 2012, filed on May 31, 2012, 3 pages.
Xin, X. et al. (Mar. 26, 1999). "Peroxisome Proliferator-Activated Receptor γ Ligands Are Potent Inhibitors of Angiogenesis in Vitro and in Vivo," J. Biol. Chem. 274(13):9116-9121.
Zhang, J. (1999). "PARP Inhibition: A Novel Approach to Treat Ischaemia/Reperfusion and Inflammation-Related Injuries," Emerging Drugs, 4:209-221.

TRICYCLIC INHIBITORS OF POLY(ADP-RIBOSE)POLYMERASE

CROSS-REFERENCE TO RELATED APPLICATIONS

This application is a continuation of application of U.S. patent application Ser. No. 15/624,201, filed on Jun. 15, 2017, which is a continuation application of U.S. patent application Ser. No. 15/089,131, filed on Apr. 1, 2016, which is a continuation application of U.S. Patent application Ser. No. 14/122,983, which is a National Phase filing under 35 U.S.C. § 371 of International Application No. PCT/US2012/040304 having an international filing date of May 31, 2012, which claims priority to U.S. Provisional Patent Application No. 61/491,851 filed May 31, 2011, the disclosures of which are incorporated herein by reference in their entirety.

FIELD OF INVENTION

The present invention relates to phosphorous containing heterocyclic compounds, such as phthalazin-1(2H)-one derivatives, which are inhibitors of the enzyme poly(ADP-ribose)polymerase (PARP). The compounds may be useful as mono-therapy or in combination with other therapeutic agents in the treatment conditions where PARP is implicated, such as cancer, inflammatory diseases and ischemic conditions.

BACKGROUND OF THE INVENTION

Poly(ADP-ribose) polymerases (PARP) constitute a family of eighteen proteins containing PARP catalytic domains (Arne et al. BioEssays (2004) 26:882). These proteins include PARP-1, PARP-2, PARP-3, tankyrase-1, tankyrase-2, and others. The founding member, and also the most studied PARP-1 is the most abundant protein in nucleus. PARP-1 consists of three main domains: an amino (N)-terminal DNA-binding domain (DBD) containing two zinc fingers, the automodification domain, and a carboxy (C)-terminal catalytic domain.

PARP enzymes are nuclear and cytoplasmic enzymes that cleave $NAD^+$ to nicotinamide and ADP-ribose to form long and branched ADP-ribose polymers on target proteins, including topoisomerases, histones and PARP itself (Le Rhun et al, Biochem. Biophys. Res. Commun. (1998) 245:1-10).

Poly(ADP-ribosylation) has been implicated in several biological processes, including DNA repair, gene transcription, cell cycle progression, cell apoptosis, cell necrosis, chromatin functions and genomic stability. Thus PARP inhibitors may be useful in the treatment a variety of conditions where activities of PARP enzymes are implicated.

The vast majority of known PARP inhibitors interact with the nicotinamide binding domain of the enzyme and behave as competitive inhibitors with respect to $NAD^+$ (Ferraris, J. Med. Chem. (2010) 53(12):4561-4584 and Bundschere et al, Anti-Cancer Agents in Medicinal Chemistry (2009) 9:816-821). Structural analogues of nicotinamide, such as benzamide and derivatives were among the first compounds to be investigated as PARP inhibitors.

Amide or aryl substituted 4-benzyl-2H-phthalazin-1-ones derivatives have been disclosed as inhibitors of PARP, e.g. in WO 2002/036576, WO 2003/070707, WO 2003/093261, WO 2004/080976, WO 2007/045877, WO 2007/138351, WO 2008/114023, WO 2008/122810, and WO 2009/093032, Certain amide substituted 6-benzylpyridazin-3(2H)-one derivatives were disclosed as potent inhibitors of PARP enzymes, e.g. in WO 2007/138351, US20080161280, US2008/0269234, WO2009/004356, WO2009/063244, and WO 2009/034326.

However, many known PARP inhibitors suffer from either a weak inhibitory activity or lack of desirable pharmaceutical properties. Thus, there remains a need for potent inhibitors of the PARP enzyme with appropriate pharmaceutical properties for clinical applications.

BRIEF SUMMARY OF THE INVENTION

Disclosed are methods and compositions for the treatment of a condition where PARP is PARP is implicated, such as cancer, inflammatory diseases and ischemic conditions.

In one aspect, provided is a compound of the formula (I):

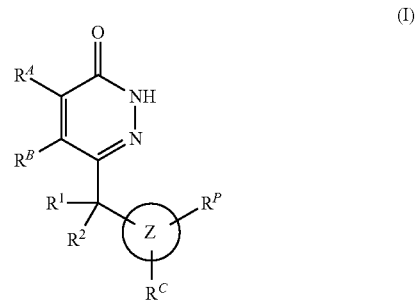

wherein
each $R^A$ and $R^B$ is independently halo, substituted or unsubstituted $C_1$-$C_6$ alkyl or $R^A$ and $R^C$ are taken together with the carbon atoms to which they are attached to form a substituted or unsubstituted 5, 6 or 7-membered ring containing 0, 1 or 2 heteroatoms selected from S, O and N;
each $R^1$ and $R^2$ is independently hydrogen, halo, hydroxy, substituted or unsubstituted $C_1$-$C_3$ alkyl or substituted or unsubstituted $C_1$-$C_3$ alkoxy;
Z is a 5 or 6-membered aryl or heteroaryl substituted with $R^C$ and $R^F$;
$R^C$ is hydrogen, halo, —$CF_3$, substituted or unsubstituted $C_1$-$C_3$ alkyl or substituted or unsubstituted alkoxy;
$R^P$ is a moiety of the formula (Ia) or (Ib):

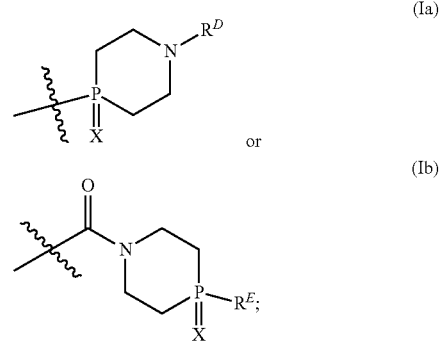

each X is independently O, S or absent;
$R^D$ is hydrogen, substituted or unsubstituted alkyl, substituted or unsubstituted cycloalkyl, substituted or unsubstituted aryl, substituted or unsubstituted heteroaryl, substituted or unsubstituted heterocyclyl, —SO$_2$R$^3$, —C(O)R$^4$, —C(=N—CN)NR$^8$R$^9$ or —C(O)NR$^5$R$^6$;

R$^3$ is a substituted or unsubstituted alkyl or substituted or unsubstituted cycloalkyl;

R$^4$ is a substituted or unsubstituted alkyl, substituted or unsubstituted cycloalkyl, substituted or unsubstituted alkoxy, or substituted or unsubstituted heterocyclyl;

each R$^5$ and R$^6$ is independently hydrogen, substituted or unsubstituted alkyl or substituted or unsubstituted cycloalkyl;

each R$^8$ and R$^9$ is independently hydrogen, substituted or unsubstituted alkyl or substituted or unsubstituted cycloalkyl, or R$^8$ and R$^9$ are taken together with the nitrogen atom to which they are attached to form a heterocyclyl;

R$^E$ is substituted or unsubstituted alkyl, substituted or unsubstituted cycloalkyl, substituted or unsubstituted aryl, or —OR$^7$; and R$^7$ is a substituted or unsubstituted alkyl or substituted or unsubstituted cycloalkyl;

or a pharmaceutically acceptable salt or solvate thereof.

In one embodiment, the PARP inhibitor compound includes any one, any combination, or all of the compounds of Table 1; or a pharmaceutically acceptable salt or solvate thereof. In some embodiments, the compound is capable of inhibiting PARP-1 enzymatic activity with an IC$_{50}$ of less than about 100 nM. In some embodiments, the compound has a PARP-1 enzyme inhibition IC$_{50}$ of less than about 1,000 nM, less than about 750 nM, less than about 500 nM, less than about 250 nM, less than about 150 nM, less than about 100 nM, less than about 50 nM, less than about 10 nM, or less than about 1 nM, as measured using the HT Universal Colorimetric PARP Assay Kit. In some embodiments, the compound is capable of inhibiting intracellular poly(ADP-ribose) formation with an EC$_{50}$ of less than about 100 nM. In some embodiments, the compound is capable of inhibiting intracellular poly(ADP-ribose) formation with an EC$_{50}$ of less than about 1,000 nM, less than about 750 nM, less than about 500 nM, less than about 250 nM, less than about 150 nM, less than about 100 nM, less than about 50 nM, less than about 10 nM, or less than about 1 nM in human cancer cells such as a human cervical carcinoma (e.g., C41 cells).

In another aspect, provided is any one of the PARP (e.g. PARO-1) inhibitor compounds present in a substantially pure form.

In another aspect, provided are formulations comprising any one of the compounds described herein and a carrier (e.g., a pharmaceutically acceptable carrier). In some embodiments, the formulation is suitable for administration to an individual. In some embodiments, the formulation comprises an effective amount of any one of the compounds described herein and a carrier (e.g., a pharmaceutically acceptable carrier). In another aspect, provided are pharmaceutical formulations comprising a PARP (e.g. PARP-1) inhibitor compound or a PARP (e.g. PARP-1) inhibitor compound in combination with a pharmaceutically acceptable carrier.

In another aspect, the invention provides method for the treatment or prevention of a condition which can be ameliorated by inhibition of PARP (e.g. PARP-1) in an individual in need thereof, the method comprising administering to the individual an effective amount of a compound detailed herein, such as a compound of the formula (I), (II), (III), (IV), (V) or any variations thereof. In some embodiments, the condition is cancer, such as a breast cancer, an ovarian cancer or a brain cancer, a cancer which is deficient in FR dependent DNA DSB repair activity, a BRCA-1 or BRCA-2 deficient tumor, or a PTEN mutant tumor. In some embodiments, the condition is an inflammatory disease or an autoimmune disease. In some embodiments, the condition is ischemia, reperfusion or renal failure, in some embodiments, the condition is a retroviral infection.

Also provided is use of compounds detailed herein, such as a compound of the formula (I), (II), (III), (IV), (V) or any variations thereof, in the manufacture of a medicament for the treatment or prevention of a condition which can be ameliorated by inhibition of PARP (e.g. PARP-1) in an individual in need thereof.

In another aspect, provided are kits for the treatment or prevention in an individual of a condition which can be ameliorated by inhibition of PARP (e.g. PARP-1), comprising any one of the compounds detailed herein or a pharmaceutically acceptable salt or solvate thereof; and packaging. In some embodiments, the kit comprises a formulation of any one of the compounds described herein or a pharmaceutically acceptable salt or solvate thereof; and packaging.

DETAILED DESCRIPTION OF THE INVENTION

The invention provides, inter alia, compositions comprising PARP inhibitors and methods for their use, including methods of treating conditions where PARP is implicated such as cancer, inflammatory diseases and ischemic conditions.

Definitions

Unless clearly indicated otherwise, the terms "a," "an," and the like, refer to one or more.

Reference to "about" a value or parameter herein includes (and describes) embodiments that are directed to that value or parameter per se. For example, description referring to "about X" includes description of "X".

It is also understood and clearly conveyed by this disclosure that reference to "the compound" or "a compound" includes and refers to any compounds or pharmaceutically acceptable salt or other form thereof as described herein.

The abbreviations used herein have their conventional meaning within the chemical and biological arts, unless otherwise specified.

"Alkyl" as used herein by itself or as part of another substituent, refers to, unless otherwise stated, a saturated straight (i.e., unbranched), branched or cyclic hydrocarbon chain, or combination thereof. Particular alkyl groups are those having 1 to 20 carbon atoms (a "C$_1$-C$_{20}$ alkyl"). More particular alkyl groups are those having 1 to 8 carbon atoms (a "C$_1$-C$_8$ alkyl"). When an alkyl residue having a specific number of carbons is named, any and all geometric isomers having that number of carbons are intended to be encompassed and described; thus, for example, "butyl" is meant to include n-butyl, sec-butyl, isobutyl, tert-butyl and cyclobutyl; "propyl" includes n-propyl, isopropyl and cyclopropyl. When an alkyl residue having a specified range of carbon atoms is named, any and all alkyl groups having any specific number(s) of carbon atoms within the specified range, inclusive, are intended to be encompassed and described; thus a "C$_1$-C$_6$ alkyl" includes an alkyl group having 1, 2, 3, 4, 5 or 6 carbon atoms. Alkyl is exemplified by groups such as methyl, ethyl, n-propyl, iso-propyl, n-butyl, tert-butyl, iso-butyl, pentyl, hexyl, cyclopropyl, cyclobutyl, cyclopentyl and cyclohexyl and the like.

Cycloalkyl is a subset of alkyl and can consist of one ring, such as cyclohexyl, or multiple rings, such as adamantyl. A cycloalkyl comprising more than one ring may be fused, Spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl and the like.

"Aryl" or "Ar" as used herein by itself or as part of another substituent, refers to, unless otherwise, stated, an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position. Examples of aryl groups include, but are not limited to, phenyl, 1-naphthyl, 2-naphthyl, and 4-biphenyl.

"Heteroaryl" or "HetAr" as used herein by itself or as part of another substituent, refers to, unless otherwise stated, an unsaturated aromatic cyclic group having from 1 to 10 annular carbon atoms and at least one annular heteroatom, including but not limited to heteroatoms such as nitrogen, oxygen and sulfur. A heteroaryl group may have a single ring (e.g., pyridyl, thiazolyl) or multiple condensed rings (e.g., phthalazinyl, quinazolinyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. Non-limiting examples of heteroaryl groups are pyrroyl, pyrazolyl, pyrazinyl, oxazolyl, isoxazolyl, thiazolyl, thiadiazolyl, furyl, pyridyl, pyrimidyl, benzothiazolyl, purinyl, benzimidazolyl, indolyl, isoquinolyl, quinolyl, quinoxalinyl, quinazolinyl, phthalazinyl, and the like.

"Halo" or "halogen" as used herein by itself or as part of another substituent, refers to, unless otherwise stated, a fluorine, chlorine, bromine, or iodine atom.

"Alkoxy" as used herein by itself or as part of another substituent, refers to, unless otherwise stated, the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like, "Substituted alkoxy" refers to the group substituted alkyl-O—.

"Heterocycle", "heterocyclic", or "heterocyclyl" as used herein by itself or as part of another substituent, refers to, unless otherwise stated, a stable saturated or unsaturated non-aromatic group having a single ring or multiple condensed rings, and having from 1 to 10 annular carbon atoms and from 1 to 4 annular heteroatoms selected from the group consisting of O, N, P, Si and S, and wherein the nitrogen, phosphorus and sulfur atoms may optionally be oxidized and the nitrogen heteroatom may optionally be quaternized. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position. Examples of heterocyclyl include, but are not limited to, 1,2-dihydrophthalazin-1-yl, phthalazin-1(2H)-one-4-yl, 1,4-azaphosphinanyl, 1-piperidinyl, 2-piperidinyl, 3-piperidinyl, 4-morpholinyl, 3-morpholinyl tetrahydrofuran-2-yl, tetrahydrofuran-3-yl, pyrrolidin-1-yl, pyrrolidin-2-yl, tetrahydrothien-2-yl, tetrahydrothien-3-yl, 1-piperazinyl, 2-piperazinyl, 1-azetidinyl, and the like.

The term "substituted" refers to the replacement of one or more hydrogen atoms of a moiety with a monovalent or divalent radical. "Optionally substituted" indicates that the moiety may be substituted or unsubstituted. A moiety lacking; the terms "optionally substituted" and "substituted" is intended to be an unsubstituted moiety (e.g., "phenyl" is intended as an unsubstituted phenyl unless indicated as a substituted phenyl or an optionally substituted phenyl). In some embodiments, an "optionally substituted" group is an unsubstituted group. In some embodiments, an "optionally substituted" group is a substituted group. For example, an "optionally substituted alkyl" in one embodiment is an unsubstituted alkyl and in another embodiment is a substituted alkyl.

Unless clearly indicated otherwise, "an individual" as used herein intends a mammal, including but not limited to a human. The invention may find use in both human medicine and in the veterinary context.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The "pharmaceutically effective amount" or "therapeutically effective amount" will vary depending on the composition being administered, the condition being treated/prevented, the severity of the condition being treated or prevented, the age and relative health of the individual, the route and form of administration, the judgment of the attending medical or veterinary practitioner, and other factors appreciated by the skilled artisan in view of the teaching provided herein.

The term "treatment" refers to the treatment of a mammal afflicted with a pathological condition and refers to an effect that alleviates the condition, e.g., by killing the cancerous cells, but also to an effect that results in the inhibition of the progress of the condition, and includes a reduction in the rate of progress, a halt in the rate of progress, amelioration of the condition, and cure of the condition.

The term "prevention" includes providing prophylaxis with respect to occurrence or recurrence of a disease in an individual. An individual may be predisposed to, susceptible to the disease, or at risk of developing the disease, but has not yet been diagnosed with the disease.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being, compatible with the other ingredients of the formulation.

A "pharmaceutically suitable carrier" or "pharmaceutically acceptable carrier," as used herein refers to pharmaceutical excipients, for example, pharmaceutically, physiologically, acceptable organic, or inorganic carrier substances suitable for enteral or parenteral application which do not deleteriously react with the extract.

The term "adjunct" refers to the use of compounds in conjunction with known therapeutic means. Such means include cytotoxic regimes of drugs and/or ionizing radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e, g, DTIC, temozolamide) and platinum based drugs (e.g. carboplatin, cisplatin) used in treating cancer.

PARP Inhibitors

In one aspect, provided is a compound of the formula (I):

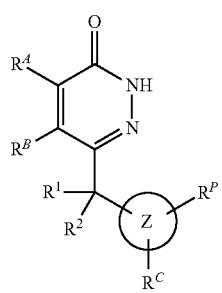

(I)

wherein
each $R^A$ and $R^B$ is independently halo, substituted or unsubstituted $C_1$-$C_6$ alkyl or $R^A$ and $R^B$ are taken together with the carbon atoms to which they are attached to form a substituted or unsubstituted 5, 6 or 7-membered ring containing 0, 1 or 2 heteroatoms selected from S, O and N;
each $R^1$ and $R^2$ is independently hydrogen, halo, hydroxy, substituted or unsubstituted $C_1$-$C_3$ alkyl or substituted or unsubstituted $C_1$-$C_3$ alkoxy;
Z is a 5 or 6-membered aryl or heteroaryl substituted with $R^C$ and $R^P$;
$R^C$ is hydrogen, halo, —$CF_3$, substituted or unsubstituted $C_1$-$C_3$ alkyl or substituted or unsubstituted $C_1$-$C_3$ alkoxy;

$R^P$ is a moiety of the formula (Ia) or (Ib):

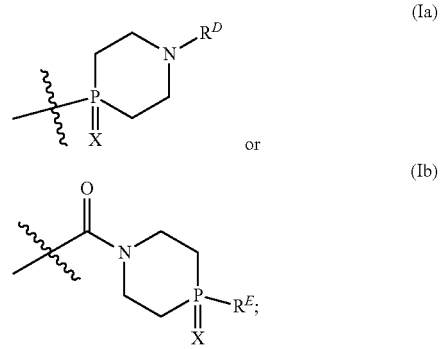

each X is independently O, S or absent;
$R^D$ is hydrogen, substituted or unsubstituted alkyl, substituted or unsubstituted cycloalkyl, substituted or unsubstituted aryl, substituted or unsubstituted heteroaryl, substituted or unsubstituted heterocyclyl, —C(O)$R^4$, —C(=N—CN)N$R^8R^9$ or —C(O)N$R^5R^6$;
$R^3$ is a substituted or unsubstituted alkyl or substituted or unsubstituted cycloalkyl;
$R^4$ is a substituted or unsubstituted alkyl, substituted or unsubstituted cycloalkyl, substituted or unsubstituted alkoxy, or substituted or unsubstituted heterocyclyl;
each $R^5$ and $R^6$ is independently hydrogen, substituted or unsubstituted alkyl or substituted or unsubstituted cycloalkyl;
each $R^8$ and $R^9$ is independently hydrogen, substituted or unsubstituted alkyl or substituted or unsubstituted cycloalkyl, or $R^8$ and $R^9$ are taken together with the nitrogen atom to which they are attached to form a heterocyclyl;
$R^F$ is substituted or unsubstituted alkyl, substituted or unsubstituted cycloalkyl, substituted or unsubstituted aryl, or —$OR^7$; and
$R^7$ is a substituted or unsubstituted alkyl or substituted or unsubstituted cycloalkyl;
or a pharmaceutically acceptable salt or solvate thereof.

In one aspect, provided is a compound of the formula (I-1):

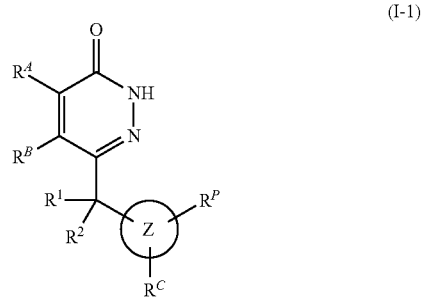

(I-1)

wherein
each $R^A$ and $R^B$ is independently halo, substituted or unsubstituted $C_1$-$C_6$ alkyl or $R^A$ and $R^B$ are taken together with the carbon atoms to which they are attached to form a substituted or unsubstituted 5, 6 or 7-membered ring containing 0, 1 or 2 heteroatoms selected from S, O and N;

each $R^1$ and $R^2$ is independently hydrogen, halo, substituted or unsubstituted $C_1$-$C_1$ alkyl or substituted or unsubstituted $C_1$-$C_3$ alkoxy;

Z is a 5 or 6-membered aryl or heteroaryl substituted with $R^C$ and $R^P$;

$R^C$ is hydrogen, halo, —$CF_3$, substituted or unsubstituted $C_1$-$C_3$ alkyl or substituted or unsubstituted $C_1$-$C_3$ alkoxy;

$R^P$ is a moiety of the formula (Ia) or (Ib):

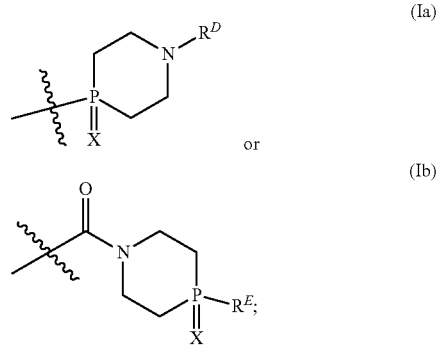

each X is independently O, S or absent;

$R^D$ is hydrogen, substituted or unsubstituted alkyl, substituted or unsubstituted cycloalkyl, substituted or unsubstituted aryl, substituted or unsubstituted heteroaryl, substituted or unsubstituted heterocyclyl, —$SO_2R^3$, —$C(O)R^4$, —$C(=N-CN)NR^8R^9$ or —$C(O)NR^5R^6$;

$R^3$ is a substituted or unsubstituted alkyl or substituted or unsubstituted cycloalkyl;

$R^4$ is a substituted or unsubstituted alkyl, substituted or unsubstituted cycloalkyl, substituted or unsubstituted alkoxy, or substituted or unsubstituted heterocyclyl;

each $R^5$ and $R^6$ is independently hydrogen, substituted or unsubstituted alkyl or substituted or unsubstituted cycloalkyl;

each $R^8$ and $R^9$ is independently hydrogen, substituted or unsubstituted alkyl or substituted or unsubstituted cycloalkyl, or $R^8$ and $R^9$ are taken together with the nitrogen atom to which they are attached to form a heterocyclyl;

$R^E$ is substituted or unsubstituted alkyl, substituted or unsubstituted cycloalkyl, substituted or unsubstituted aryl, or $OR^7$; and $R^7$ is a substituted or unsubstituted alkyl or substituted or unsubstituted cycloalkyl;

or a pharmaceutically acceptable salt or solvate thereof.

A "substituted" moiety, such as a substituted alkyl, substituted alkoxy, substituted aryl, substituted heteroaryl or substituted heterocyclyl, may have one or more substituents. The substituents on an substituted moiety of the formula (I) may be one, two, three, or more groups selected from, but not limited to, hydroxyl, nitro, amino (e.g., —$NH_2$ or dialkyl amino), imino, cyano, halo (such as F, Cl, Br, I), haloalkyl (such as —$CCl_3$ or —$CF_3$), thio, sulfonyl, thioamido, amidino, imidino, oxo, oxamidino, methoxamidino, imidino, guanidino, sulfonamido, carboxyl, formyl, alkyl, alkoxy, alkoxy-alkyl, alkylcarbonyl, alkylcarbonyloxy (—OCOR), aminocarbonyl, arylcarbonyl, aralkylcarbonyl, carbonylamino, heteroarylcarbonyl, heteroaralkyl-carbonyl, alkylthio, aminoalkyl, cyanoalkyl, carbamoyl (—NHCOOR— or —OCONHR—), urea (—NHCONHR—), aryl and the like, where R is any suitable group, e.g., alkyl or alkylene. In some embodiments, the optionally substituted moiety is optionally substituted only with select radicals, as described herein. In some embodiments, the above groups (e.g., alkyl groups) are optionally substituted with, for example, alkyl (e.g., methyl or ethyl), haloalkyl (e.g., —$CCl_3$, —CH—CHO, or —$CF_3$), cycloalkyl (e.g., —$C_3H_5$, —$C_4H_7$, —$C_5H_9$), amino (e.g., —$NH_2$ or dialkyl amino), alkoxy (e.g., methoxy), heterocyclyl (e.g., as morpholine, piperazine, piperidine, azetidine), hydroxyl, and/or heteroaryl oxazolyl). In some embodiments, a substituent group is itself optionally substituted. In some embodiments, a substituent group is not itself substituted. The group substituted onto the substitution group can be, for example, carboxyl, halo, nitro, amino, cyano, hydroxyl, alkyl, alkenyl, alkynyl, alkoxy, aminocarbonyl, —SR, thioamido, —$SO_3H$, —$SO_2R$ or cycloalkyl, where R is any suitable group, e.g., a hydrogen or alkyl.

In some embodiments, each $R^1$ and $R^2$ is hydrogen. In some embodiments, one of $R^1$ and $R^2$ is hydrogen and the other is halo, substituted or unsubstituted $C_1$-$C_3$ alkyl or substituted or unsubstituted $C_1$-$C_3$ alkoxy. In some embodiments, each $R^1$ and $R^2$ is independently halo, substituted or unsubstituted $C_1$-$C_3$ alkyl or substituted or unsubstituted $C_1$-$C_3$ alkoxy. In some embodiments, each $R^1$ and $R^2$ is independently hydrogen or halogen.

In some embodiments, each $R^1$ and $R^2$ is hydrogen, and one or both of $R^1$ and $R^2$ are isotopically enriched with deuterium ($^2H$). In one variation one of $R^1$ and $R^2$ is hydrogen and the other is deuterium. In another variation, both $R^1$ and $R^2$ are deuterium. In some embodiments, one of $R^1$ and $R^2$ is hydroxy. In some embodiments, one of $R^1$ and $R^2$ is hydrogen and the other is hydroxy.

It is understood and clearly conveyed herein that each and every variation of $R^1$ and $R^2$ described herein may be combined with each and every variation of other variables (e.g., $R^A$, $R^B$, Z, $R^C$ and $R^P$) described herein, where applicable, as if each and every combination were listed separately.

In some embodiments, each $R^A$ and $R^H$ is independently halo or substituted or unsubstituted $C_1$-$C_6$ alkyl. In some embodiments, each $R^A$ and $R^B$ is independently a halo group. In some embodiments, each $R^A$ and $R^H$ is independently a substituted or unsubstituted $C_1$-$C_6$ alkyl. In some embodiments, one of $R^A$ and $R^H$ is a halo group and the other is a substituted or unsubstituted $C_1$-$C_6$ alkyl. In some embodiments, $R^A$ and $R^B$ are taken together with the carbon atoms to which they are attached to form a substituted or unsubstituted 5, 6 or 7-membered ring containing 0, 1 or 2 heteroatoms selected from S, O and N. In some embodiments, $R^A$ and $R^B$ are taken together with the carbon atoms to which they are attached to form a substituted or unsubstituted 5, 6 or 7-membered carbocycle. In some embodiments, $R^A$ and $R^B$ are taken together with the carbon atoms to which they are attached to form a substituted or unsubstituted 6-membered carbocycle. In some embodiments, $R^A$ and $R^H$ are taken together with the carbon atoms to which they are, attached to form a substituted or unsubstituted 5, 6 or 7-membered ring containing 1 or 2 heteroatoms selected from S, O and N. In some embodiments, $R^A$ and $R^H$ are taken together with the carbon atoms to which they are attached to form a substituted or unsubstituted 5, 6 or 7-membered ring containing one heteroatom selected from S, O and N. In some embodiments, $R^A$ and $R^B$ are taken together with the carbon atoms to which they are attached to form a substituted or unsubstituted 6-membered aromatic ring (e.g., a phenyl ring). In some embodiments, $R^A$ and $R^B$ are taken together with the carbon atoms to which they are attached to form a substituted or unsubstituted heteroaromatic ring.

In some embodiments, the compound of formula (I) where $R^A$ and $R^B$ are together with the atoms to which they are attached to form an aromatic ring has the formula (II):

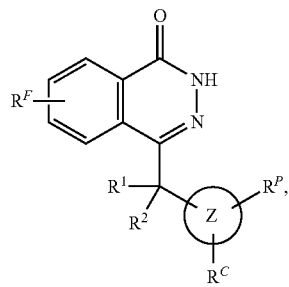

(II)

wherein $R^1$, $R^2$, $R^C$, $R^P$ and Z are as defined for the formula (I) and $R^F$ is hydrogen, halo, —$CF_3$, substituted or unsubstituted $C_1$-$C_3$ alkyl or substituted or unsubstituted $C_1$-$C_3$ alkoxy; or a pharmaceutically acceptable salt or solvate thereof.

In some embodiments, $R^F$ is hydrogen. In some embodiments, $R^F$ is halo (e.g., fluoro). In some embodiments, $R^F$ is —$CF_3$, or substituted or unsubstituted $C_1$-$C_3$ alkyl. In some embodiments, $R^F$ is substituted or unsubstituted $C_1$-$C_3$ alkoxy.

It is understood and clearly conveyed herein that each and every variation of $R^A$ and $R^B$ described herein may be combined with each and every variation of other variables (e.g., $R^1$, $R^2$, Z, $R^C$ and $R^P$) described herein, where applicable, as if each and every combination were listed separately.

In some embodiments, at least one of $R^1$ and $R^2$ is hydrogen. In some embodiments, each $R^1$ and $R^2$ is hydrogen. In some embodiments, each $R^F$, $R^1$ and $R^2$ is hydrogen.

In some embodiments, Z is a 5 or 6-membered heteroaryl substituted with $R^C$ and $R^P$. In some embodiments, Z is a 5-membered heteroaryl substituted with $R^C$ and $R^P$. In some embodiments. Z is a 6-membered heteroaryl substituted with $R^C$ and $R^P$. In some embodiments, Z is a 5 or 6-membered aryl substituted with $R^C$ and $R^P$. In some embodiments, Z is a 5-membered aryl substituted with $R^C$ and $R^P$. In some embodiments, Z is a 6-membered aryl substituted with $R^C$ and $R^P$. In some embodiments, Z is a phenyl substituted with $R^C$ and $R^P$.

It is understood and clearly conveyed herein that each and every variation of Z described herein may be combined with each and every variation of other variables (e.g., $R^1$, $R^2$, $R^A$, $R^B$, $R^C$ and $R^P$) described herein, where applicable, as if each and every combination were listed separately.

In some embodiments, the compound is of the formula (II), where $R^1$, $R^2$, $R^C$, $R^F$ and Z are as defined for the formula (II) and $R^P$ is a moiety of the formula (Ia); the compound is of the formula (IIa). In some embodiments, the compound is of the formula (II), where $R^1$, $R^2$, $R^C$, $R^F$ and Z are as defined for the formula (II) and R is a moiety of the formula (Ib); the compound is of the formula (IIb).

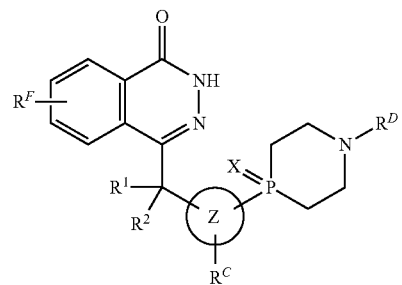

(IIa)

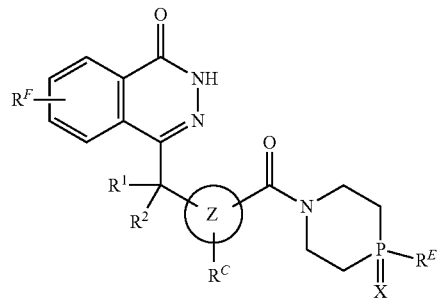

(IIb)

The present invention also provides compounds of formula (III):

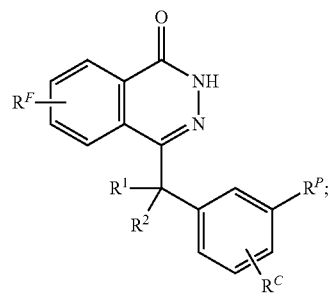

(III)

wherein $R^1$, $R^2$, $R^C$, $R^P$ and $R^F$ are as defined for the formula (I) or (II); or a pharmaceutically acceptable salt or solvate thereof.

In some embodiments, at least one of $R^1$ and $R^2$ is hydrogen. In some embodiments, each $R^1$ and $R^2$ is hydrogen. In some embodiments, $R^F$ is hydrogen. In some embodiments, $R^F$ is halo (e.g., fluoro). In some embodiments, one or both $R^1$ and $R^2$ is isotopically enriched with deuterium. In some embodiments, each $R^1$ and $R^2$ is deuterium.

In some embodiments, $R^C$ is hydrogen. In some embodiments, $R^C$ is halo, —$CF_3$, substituted or unsubstituted $C_1$-$C_3$ alkyl or substituted or unsubstituted $C_1$-$C_3$ alkoxy. In some embodiments. $R^C$ is a halo group (e.g., fluoro). In some embodiments, $R^C$ is —$CF_3$. In some embodiments, $R^C$ is substituted or unsubstituted $C_1$-$C_3$ alkyl. In some embodiments, $R^C$ is substituted or unsubstituted $C_1$-$C_3$ alkoxy. In some embodiments, $R^C$ is connected to the phenyl ring at a position ortho to the $R^P$ group. In some embodiments, $R^C$ is connected to the phenyl ring at a position para to the $R^P$ group. In some embodiments, $R^C$ is connected to the phenyl ring at a position meta to the $R^P$ group.

In some embodiments, $R^P$ is of the formula (Ia) where X is absent. In some embodiments, $R^P$ is of the formula (Ia) where X is O. In some embodiments, $R^P$ is of the formula (Ia) where X is S.

In some embodiments, $R^P$ is of the formula (Ib) where X is absent. In some embodiments, $R^P$ is of the formula (Ib) where X is O. In some embodiments, $R^P$ is of the formula (Ib) where X is S.

In some preferred embodiments, the compound is of the formula (IIIa):

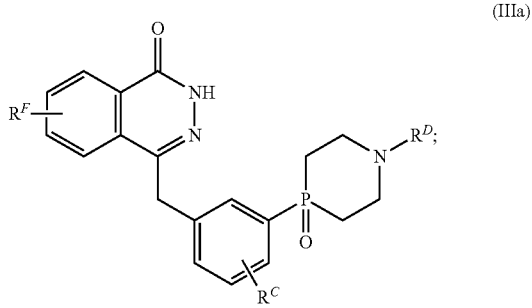

(IIIa)

wherein $R^C$, $R^D$ and $R^F$ are as defined for the formula (I), (II) or (III); or a pharmaceutically acceptable salt or solvate thereof.

In one variation, $R^D$ is hydrogen, substituted or unsubstituted alkyl, or substituted or unsubstituted cycloalkyl. In another variation, $R^D$ is substituted or unsubstituted $C_1$-$C_6$ alkyl. In some embodiments, $R^D$ is an unsubstituted $C_1$-$C_6$ alkyl. In another variation, $R^D$ is a substituted or unsubstituted $C_1$-$C_6$ cycloalkyl. In another variation, $R^D$ is selected from the group consisting of hydrogen, methyl, ethyl, n-propyl, isopropyl, n-butyl, isobutyl, t-butyl, isopentyl, trifluoroethyl, cyclopropylmethyl, cyclopropyl, cyclobutyl and cyclopentyl. In another variation, $R^D$ is hydrogen, methyl or ethyl.

In some embodiments, $R^D$ is methyl or ethyl. In another variation, $R^D$ is a substituted or unsubstituted aryl. In another variation, $R^D$ is substituted or unsubstituted phenyl. In another variation, $R^D$ is substituted or unsubstituted heteroaryl. In another variation, $R^D$ is a substituted or unsubstituted 6-membered heteroaryl. In another variation, $R^D$ is a substituted or unsubstituted 5-membered heteroaryl. In another variation, $R^D$ is a substituted or unsubstituted heteroaryl selected from the group consisting of pyridinyl, pyridazinyl, pyrimidinyl, quinazolinyl, imidazolyl, oxazolyl, oxadiazolyl, pyrazolyl, thiazoly, and thiadiazolyl. In another variation, $R^D$ is a substituted or unsubstituted heteroaryl selected from the group consisting of pyridinyl, pyridazinyl, pyrimidinyl, quinazolinyl, thiazoly, and thiadiazolyl. In another variation, $R^D$ is a substituted or unsubstituted pyridinyl (e.g., 2-pyridyl, 3-pyridiyl or 4-pyridyl). In another variation, $R^D$ is a substituted or unsubstituted pyrimidinyl (e.g., 2-pyrimidiyl, 4-pyrimidiyl or 5-pyrimidyl), In another variation, $R^D$ is substituted or unsubstituted heterocyclyl.

In one variation. $R^D$ is —C(O)NR$^5$R$^6$, where each $R^5$ and $R^6$ is independently hydrogen, substituted or unsubstituted alkyl or substituted or unsubstituted cycloalkyl. In another variation, each $R^5$ and $R^6$ is independently hydrogen or an unsubstituted alkyl. In one particular variation, each $R^5$ and $R^6$ is methyl.

In one variation, $R^D$ is —SO$_2$R$^3$ where $R^3$ is a substituted or unsubstituted alkyl or substituted or unsubstituted cycloalkyl. In another variation, $R^3$ is a substituted or unsubstituted cycloalkyl (e.g., cyclopropyl). In another variation, $R^3$ is a substituted or unsubstituted alkyl (e.g., methyl).

In some embodiments, $R^D$ is —C(O)R$^4$ where $R^4$ is a substituted or unsubstituted alkyl, substituted or unsubstituted cycloalkyl, substituted or unsubstituted alkoxy, or substituted or unsubstituted heterocyclyl. In another variation, $R^4$ is a substituted or unsubstituted alkyl or substituted or unsubstituted cycloalkyl. In another variation, $R^4$ is an unsubstituted $C_1$-$C_6$ alkyl or unsubstituted $C_1$-$C_6$ cycloalkyl. In another variation, $R^4$ is a substituted or unsubstituted heterocyclyl. In another variation, $R^4$ is a substituted or unsubstituted heterocyclyl selected from pyrrolidinyl and tetrahydrofuranyl.

In some embodiments, $R^D$ is —C(=N—CN)NR$^8$R$^9$ where each $R^8$ and $R^9$ is independently hydrogen, substituted or unsubstituted alkyl or substituted or unsubstituted cycloalkyl. In some embodiments. $R^D$ is —C(=N—CN)NR$^8$R$^9$ where $R^8$ and $R^9$ are taken together with the nitrogen atom to which they are attached to form a substituted or unsubstituted heterocyclyl. In another variation, $R^D$ is —C(=N—CN)NR$^8$R$^9$ where $R^8$ and $R^9$ are taken together with the nitrogen atom to which they are attached to form 1-azetidinyl.

In some embodiments, $R^D$ is selected from the group consisting of:

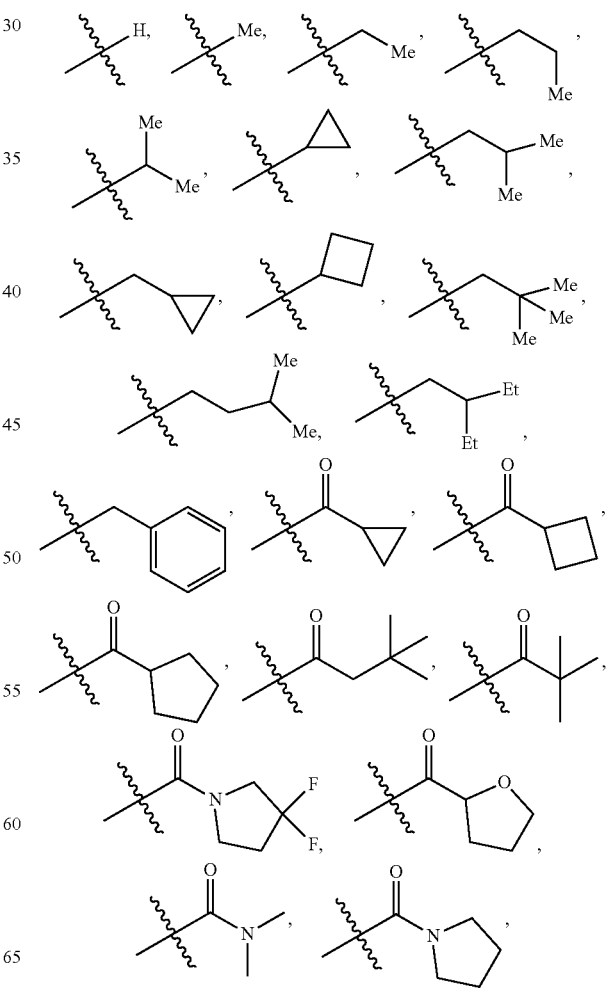

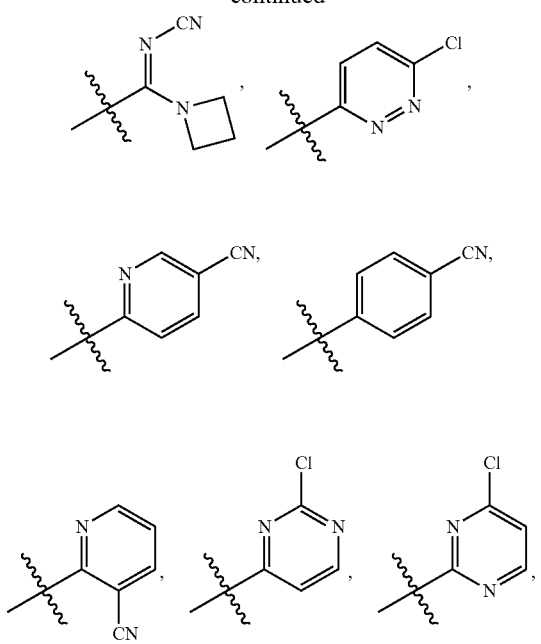

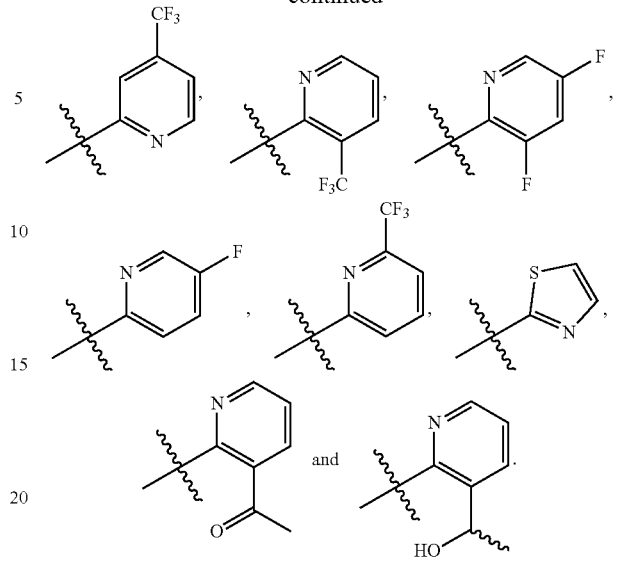

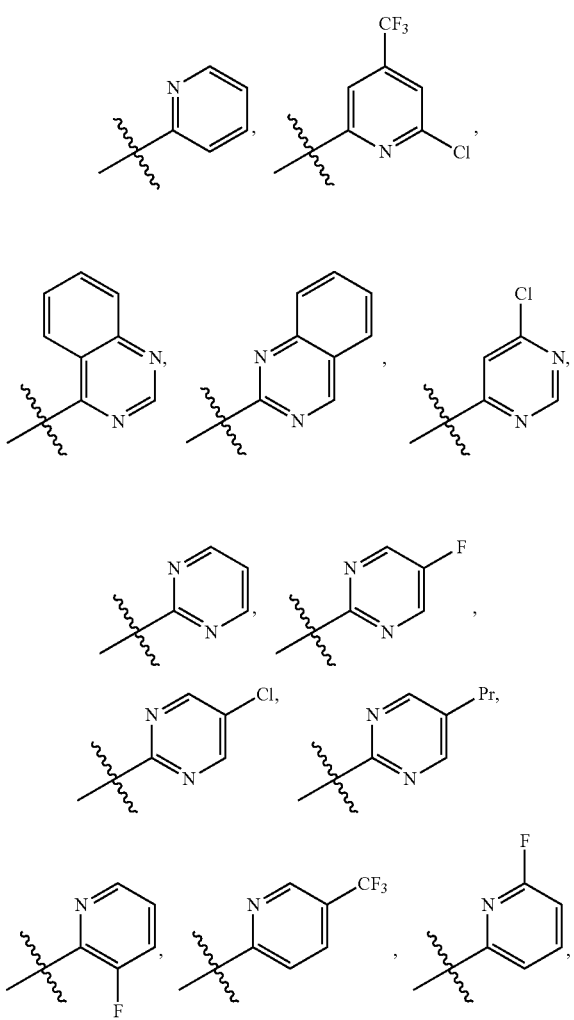

In some preferred embodiments, the compound is of the formula (IIIb):

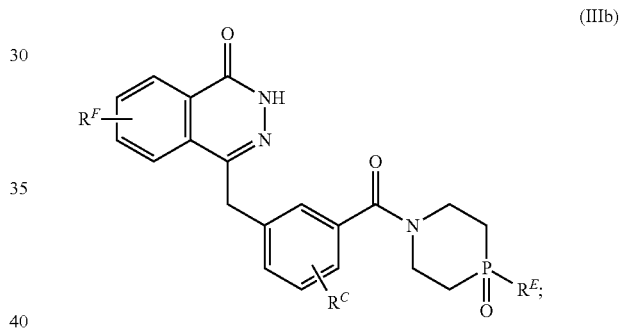

(IIIb)

wherein $R^C$, $R^E$ and $R^F$ are as defined for the formula (I), (II) or (III); or a pharmaceutically acceptable salt or solvate thereof.

In some embodiments, $R^E$ is substituted or unsubstituted alkyl, or substituted or unsubstituted cycloalkyl. In another variation, $R^E$ is a substituted or unsubstituted alkyl. In another variation, $R^E$ is an unsubstituted alkyl. In another variation, $R^E$ is an unsubstituted $C_1$-$C_6$ alkyl. In another variation, $R^E$ is methyl, ethyl or isopropyl. In another variation, $R^E$ is substituted or unsubstituted aryl.

In some embodiments, $R^E$ is —$OR^7$ where $R^7$ is a substituted or unsubstituted alkyl or substituted or unsubstituted cycloalkyl. In one variation, $R^7$ is a substituted or unsubstituted $C_1$-$C_6$ alkyl or substituted or unsubstituted $C_1$-$C_6$ cycloalkyl. In another variation, $R^7$ is an unsubstituted $C_1$-$C_6$ alkyl (e.g., methyl or ethyl).

The embodiments and variations described herein are suitable for compounds of any formulae detailed herein, where applicable.

In referring to "variations" of formula (I), (II), (III), and/or (IV), unless clearly dictated otherwise by context or inconsistent with chemical rationale, it is intended that variations refer, for example, to various sub-formulae of formula (II), (III), and/or (IV), for example, formula (Ia), (IIb), (IIa), (IIIb), (IVa), (IVb), etc. as set forth herein.

In some preferred embodiments, the compound is of the formula (IV):

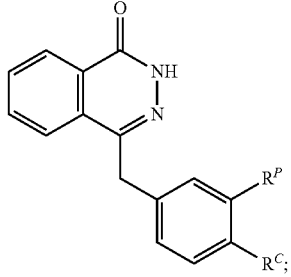

(IV)

wherein $R^C$ is hydrogen, halo, —$CF_3$, substituted or unsubstituted $C_1$-$C_3$ alkyl or substituted or unsubstituted $C_1$-$C_3$ alkoxy;

$R^P$ is a moiety of the formula (Ia) or (Ib):

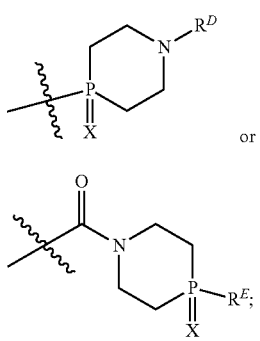

(Ia)

or (Ib)

X is O;

$R^D$ is hydrogen, substituted or unsubstituted alkyl, substituted or unsubstituted cycloalkyl, substituted or unsubstituted aryl, substituted or unsubstituted heteroaryl, substituted or unsubstituted heterocyclyl, —$SO_2R^3$, —$C(O)R^4$, —$C(=N-CN)NR^8R^9$ or —$C(O)NR^5R^6$;

$R^3$ is a substituted or unsubstituted alkyl or substituted or unsubstituted cycloalkyl;

$R^4$ is a substituted or unsubstituted alkyl, substituted or unsubstituted cycloalkyl, substituted or unsubstituted alkoxy, or substituted or unsubstituted heterocyclyl;

each $R^5$ and $R^6$ is independently hydrogen, substituted or unsubstituted alkyl or substituted or unsubstituted cycloalkyl;

each $R^8$ and $R^9$ is independently hydrogen, substituted or unsubstituted alkyl or substituted or unsubstituted cycloalkyl, or $R^8$ and $R^9$ are taken together with the nitrogen atom to which they are attached to form a heterocyclyl;

$R^E$ is substituted or unsubstituted alkyl, substituted or unsubstituted cycloalkyl, substituted or unsubstituted aryl, or —$OR^7$; and $R^7$ is a substituted or unsubstituted alkyl or substituted or unsubstituted cycloalkyl; or a pharmaceutically acceptable salt or solvate thereof.

In some preferred embodiments, the compound is of the formula (IVa):

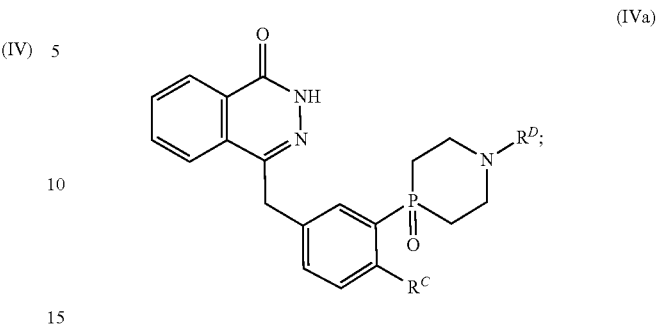

(IVa)

wherein $R^C$ and $R^D$ are as defined for the formula (IV); or a pharmaceutically acceptable salt or solvate thereof.

In some variations, the compound is of the formula (IVa) where $R^D$ is as defined for variations of the formula (IIIa), where applicable, as if each and every variation is individually recited for the formula (IVa).

In one variation, the compound is of the formula (IVa) where $R^D$ is hydrogen, substituted or unsubstituted alkyl, or substituted or unsubstituted cycloalkyl, or a pharmaceutically acceptable salt or solvate thereof. In another variation, $R^D$ is selected from the group consisting of hydrogen, methyl, ethyl, n-propyl, isopropyl, n-butyl, isobutyl, t-butyl, isopentyl, trifluoroethyl, cyclopropylmethyl, cyclopropyl, cyclobutyl and cyclopentyl. In another variation, $R^D$ is a substituted or unsubstituted aryl or substituted or unsubstituted heteroaryl. In a particular variation, $R^D$ is substituted or unsubstituted phenyl. In one variation, $R^D$ is a substituted or unsubstituted heteroaryl selected from the group consisting of pyridinyl, pyridazinyl, pyrimidinyl, quinazolinyl, imidazolyl, oxazolyl, oxadiazolyl, pyrazolyl, thiazoly, and thiadiazolyl. In another variation, $R^D$ is —$C(O)NR^5R^6$, —$SO_2R^3$, or —$C(=N-CN)NR^8R^9$. In another variation, $R^D$ is —$C(O)NR^5R^6$ where each $R^5$ and $R^6$ is methyl. In another variation, $R^D$ is —$C(=N-CN)NR^8R^9$ where each $R^8$ and $R^9$ is independently hydrogen, substituted or unsubstituted alkyl or substituted or unsubstituted cycloalkyl. In another variation, $R^D$ is —$C(=N-CN)NR^8R^9$ where $R^8$ and $R^9$ are taken together with the nitrogen atom to which they are attached to form a heterocyclyl (e.g., 1-azetidinyl). In another variation, $R^D$ is —$C(O)R^4$. In some of these variations, $R^4$ is an unsubstituted $C_1$-$C_6$ alkyl or unsubstituted $C_1$-$C_6$ cycloalkyl. In some of these variations, $R^4$ is a substituted or unsubstituted heterocyclyl selected from pyrrolidinyl and tetrahydrofuranyl.

In one variation, provided is a compound of the formula (IVa), where $R^C$ is halo (e.g., fluoro) and $R^D$ is as defined for the formula (IV). In some of these variations, $R^D$ is selected from the group consisting of:

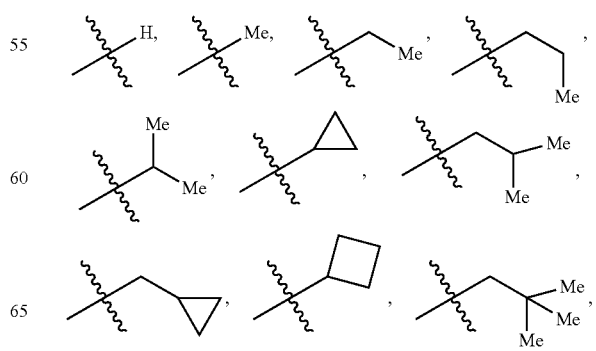

-continued

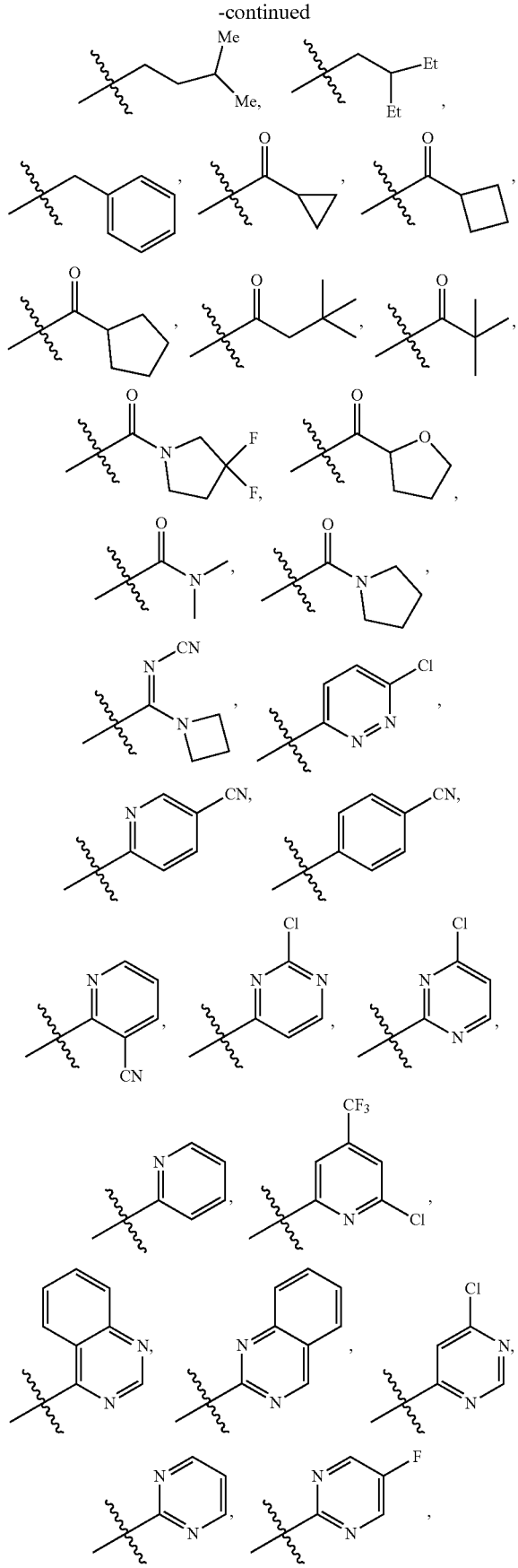

-continued

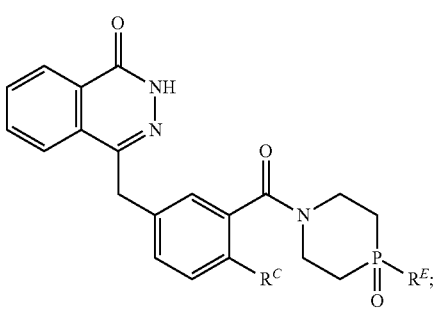

In some preferred embodiments, the compound is of the formula (IVb):

(IVb)

[structure of formula IVb]

wherein $R^C$ and $R^E$ are as defined for the formula (IV); or a pharmaceutically acceptable salt or solvate thereof.

In one variation, the compound is of the formula (IVb) where $R^D$ is substituted or unsubstituted alkyl, substituted or unsubstituted cycloalkyl or —$OR^7$; or a pharmaceutically acceptable salt or solvate thereof. In some of these variations, $R^E$ is an unsubstituted $C_1$-$C_6$ alkyl. In some of these variations, $R^E$ is —$OR^7$ where $R^7$ is an unsubstituted $C_1$-$C_6$ alkyl.

In another variation, the compound is of the formula (IVb) where $R^C$ is halo (e.g., fluoro) and $R^E$ is substituted or unsubstituted alkyl, substituted or unsubstituted cycloalkyl or —$OR^7$; or a pharmaceutically acceptable salt or solvate thereof. In some of these variations, $R^E$ is an unsubstituted $C_1$-$C_6$ alkyl (e.g., methyl, ethyl or isopropyl). In some of these variations, $R^E$ is —$OR^7$ where $R^7$ is an unsubstituted $C_1$-$C_6$ alkyl (e.g., ethyl).

In some embodiments, the compound is of the formula (V):

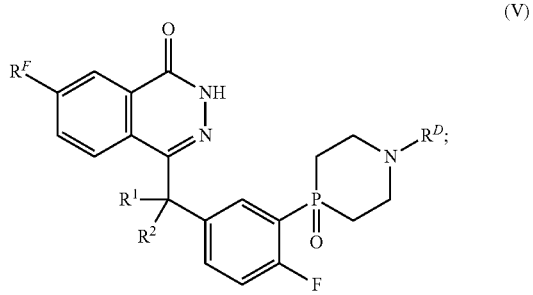

wherein
- each $R^1$ and $R^2$ is independently hydrogen, halo, hydroxy, substituted or unsubstituted $C_1$-$C_3$ alkyl or substituted or unsubstituted $C_1$-$C_3$ alkoxy;
- $R^D$ is hydrogen, substituted or unsubstituted alkyl, substituted or unsubstituted cycloalkyl, substituted or unsubstituted aryl, substituted or unsubstituted heteroaryl, or substituted or unsubstituted heterocyclyl; and
- $R^F$ is hydrogen, halo, —$CF_3$, substituted or unsubstituted $C_1$-$C_3$ alkyl or substituted or unsubstituted $C_1$-$C_3$ alkoxy;

or a pharmaceutically acceptable salt or solvate thereof.

In some embodiments, $R^F$ is hydrogen. In some embodiments, $R^F$ is halo (e.g., fluoro). In some embodiments, $R^D$ is hydrogen, substituted or unsubstituted alkyl, substituted or unsubstituted cycloalkyl, or substituted or unsubstituted heteroaryl. In some embodiments, $R^D$ is hydrogen. In some embodiments, $R^D$ is substituted alkyl (e.g., benzyl). In some embodiments, $R^D$ is substituted or unsubstituted cycloalkyl (e.g., cyclopropyl). In some embodiments. $R^D$ is substituted or unsubstituted heteroaryl (e.g., 2-pyrimidinyl). In some embodiments, each $R^1$ and $R^2$ is independently hydrogen or hydroxy. In some embodiments, each $R^1$ and $R^2$ is hydrogen. In some embodiments, each $R^1$ and $R^2$ is hydrogen, and one or both of $R^1$ and $R^2$ are isotopically enriched with deuterium ($^2H$). In one variation one of $R^1$ and $R^2$ is hydrogen and the other is deuterium. In another variation, both $R^1$ and $R^2$ are deuterium. In some embodiments, one of $R^1$ and $R^2$ is hydroxy. In some embodiments, one of $R^1$ and $R^2$ is hydrogen and the other is hydroxy.

The compounds depicted herein may be present as salts even if salts are not depicted and it is understood that the invention embraces all salts and solvates (e.g., hydrate) of the compounds depicted here, as well as the non-salt and non-solvate form of the compound, as is well understood by the skilled artisan. In some embodiments, the salts of the compounds of the invention are pharmaceutically acceptable salts.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Where one or more tertiary amine moiety is present in the compound, such as the compound of the formula (I), (II), (III) or (IV), the N-oxides are also provided and described. The N-oxides may be formed by conventional means, such as reacting the compound of formula (I) with oxone in the presence of wet alumina.

The compounds depicted herein may have asymmetric centers, chiral axis, and/or chiral planes (as described in: E. L. Eliel and S. H. Wilen, Stereochemistry of Carbon Compounds, John Wiley & Sons, New York, 1994, pages 1119-1190), and occur as racemates, racemic mixtures where one enantiomer may be enriched, individual diastereomers, and mixtures of stereoisomers. All stereoisomers, including enantiomers and diastereomers are embraced by the present invention.

The compounds depicted herein may exist as tautomers. Both tautomeric forms are intended to be encompassed by the scope of the invention, even though only one tautomeric structure may be depicted.

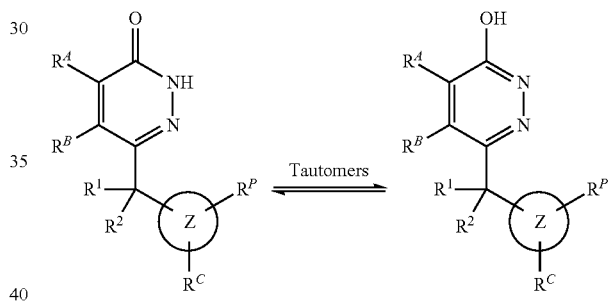

The compounds herein may also contain unnatural proportions of atomic isotopes at one or more of the atoms that constitute such compounds. In some embodiments, the compound is isotopically-labeled, such as an isotopically-labeled compound of the formula (I), (II), (III) or (IV), where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2H$, $^3H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^3H$ and $^{14}C$) are useful in compound or substrate tissue distribution study. Wherein certain heavier isotope (e.g. $^2H$) may afford certain therapeutic advantage resulting from possible greater metabolic stability.

The present invention includes within its scope prodrugs of the compound, such as the compound of the formula (I), (II), (III) or (IV). In general, such prodrugs are functional derivatives of the compound, such as functional derivatives of the compound of the formula (I), (II), (III) or (IV), which are readily convertible in vivo into the required compound of the formula (I), (II), (III) or (IV), Conventional procedures for the selection and preparation of suitable prodrug derivatives are described, for example, in "Prodrugs: Challenges and Rewards", ed. V. J. Stella et al, Springer, 2007. A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfuric ester, or reduction or oxidation of a susceptible functionality.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 30% impurity, wherein the impurity denotes a compound other than the compound comprising the majority of the composition or a salt thereof. In some embodiments, a composition of substantially pure compound or a salt thereof is provided wherein the composition contains no more than about 30%, about 25%, about 20%, about 15%, about 10%, about 5%, about 3% or about 1% impurity.

In one aspect, provided are kits comprising a compound of the invention, or a salt or solvate thereof, and suitable packaging. In one embodiment, a kit further comprises instructions for use. In one aspect, a kit comprises a compound of the invention, or a salt or solvate thereof, and instructions for use of the compounds in the treatment or prevention of a condition which can be ameliorated by inhibition of PARP (e.g. PARP-1) in an individual in need thereof.

Articles of manufacture comprising a compound of the invention, or a salt or solvate thereof, in a suitable container are provided. The container may be a vial, jar, ampoule and the like.

Representative examples of compounds detailed herein, including intermediates and final compounds according to the invention are depicted in the Tables and Examples below. It is understood that in one aspect, any of the compounds may be used in the methods detailed herein, including, where applicable, intermediate compounds that may be isolated and administered to an individual.

Representative compounds of the invention are shown in Table 1. In some embodiments, the invention provides a compound of Table 1, in its free base form or as

TABLE 1

Exemplary compounds

| Compound | Example No. |
|---|---|
| (4-(3-(1-benzyl-4-oxido-1,4-azaphosphinan-4-yl)-4-fluorobenzyl)phthalazin-1(2H)-one | 1 |
| (4-(3-(1-(cyclopentanecarbonyl)-4-oxido-1,4-azaphosphinan-4-yl)-4-fluorobenzyl)phthalazin-1(2H)-one | 2 |
| 4-(3-(1-(cyclopropanecarbonyl)-4-oxido-1,4-azaphosphinan-4-yl)-4-fluorobenzyl)phthalazin-1(2H)-one | 3 |
| (4-(3-(1-(cyclobutanecarbon yl)-4-oxido-1,4-azaphosphinan-4-yl)-4-fluorobenzyl)phthalazin-1(2H)-one | 4 |
| 4-(3-(1-(3,3-dimethylbutanoyl)-4-oxido-1,4-azaphosphinan-4-yl)-4-fluorobenzyl)phthalazin-1(2H)-one | 5 |
| (4-(3-(1-(3,3-difluoropyrrolidine-1-carbonyl)-4-oxido-1,4-azaphosphinan-4-yl)-4-fluorobenzyl)phthalazin-1(2H)-one | 6 |
| 4-(4-fluoro-3-(4-oxido-1-(tetrahydrofuran-2-carbonyl)-1,4-azaphosphinan-4-yl)benzyl)phthalazin-1(2H)-one | 7 |
| 4-(4-fluoro-3-(4-oxido-1-pivaloyl-1,4-azaphosphinan-4-yl)benzyl)phthalazin-1(2H)-one | 8 |
| 4-(2-fluoro-5-((4-oxo-3,4-dihydrophthalazin-1-yl)methyl)phenyl)-N,N-dimethyl-1,4-azaphosphinane-1-carboxamide 4-oxide | 9 |
| 4-(4-fluoro-3-(4-oxido-1-pivaloyl-1,4-azaphosphinan-4-yl)benzyl)phthalazin-1(2H)-one | 10 |
| (E/Z)-N-(azetidin-1-yl(4-(2-fluoro-5-((4-oxo-3,4-dihydrophthalazin-1-yl)methyl)phenyl)-4-oxido-1,4-azaphosphinan-1-yl)methylene)cyanamide | 11 |
| 4-(4-(fluoro-3-(4-oxido-1-(pyrimidin-2-yl)-1,4-azaphosphinan-4-yl)benzyl)phthalazin-1(2H)-one | 12 |
| 4-(3-(1-(6-chloropyridazin-3-yl)-4-oxido-1,4-azaphosphinan-4-yl)-4-fluorobenzyl)phthalazin-1(2H)-one | 13 |
| 6-(4-(2-fluoro-5-((4-oxo-3 ,4-dihydrophthalazin-1-yl)methyl)phenyl)-4-oxido-1,4-azaphosphinan-1-yl)nicotinonitrile | 14 |
| 4-(4-(2-fluoro-5-((4-oxo-3,4-dihydrophthalazin-1-yl)-1-yl)phenyl)-4-oxido-1,4-azaphosphinan-l-yl)benzonitrile | 15 |
| 2-(4-(2-fluoro-5-((4-oxo-3,4-dihydrophthalazin-1-yl)methyl)phenyl)-4-oxido-1,4-azaphosphinan-l-yl)nicotinonitrile | 16 |
| 4-(3-(1-(2-chloropyrimidin-4-yl)-4-oxido-1,4-azaphosphinan-4-yl)-4-fluorobenzyl)phthalazin-1(2H)-one | 17 |
| 4-(3-(1-(4-chloropyrimidin-2-yl)-4-oxido-1,4-azaphosphinal-4-yl)-4-fluorobenzyl)phthalazin-1(2H)-one | 18 |
| 4-(4-fluoro-3-(4-oxido-1-(pyridin-2-yl)-1,4-azaphosphinan-4-yl)benzyl)phthalazin-1(2H)-one | 19 |
| 4-(3-(1-(3-chloro-5-(trifluoromethyl)pyridin-2-yl)-4-oxido-1,4-azaphosphinan-4-yl)-4-fluorobenzyl)phthalazin-1(2H)-one | 20 |
| 4-(4-fluoro-3-(4-oxido-1-(quinazolin-4-yl)-1,4-azaphosphinan-4-yl)benzyl)phthalazin-1(2H)-one | 21 |
| 4-(3-(1-(6-chloropyrimidin-4-yl)-4-oxido-1,4-azaphosphinan-4-yl)-4-fluorobenzyl)phthalazin-1(2H)-one | 22 |

TABLE 1-continued

Exemplary compounds

| Compound | Example No. |
|---|---|
| 4-(4-fluoro-3-(1-(3-fluoropyridin-2-yl)-4-oxido-1,4-azaphosphinan-4-yl)benzyl)phthalazin-1(2H)-one | 23 |
| 4-(4-fluoro-3-(4-oxido-1-(5-(trifluoromethyl)pyridin-2-yl)-1,4-azaphosphinan-4-yl)benzyl)phthalazin-1(2H)-one | 24 |
| 4-(4-fluoro-3-(1-(6-fluoropyridin-2-yl)-4-oxido-1,4-azaphosphinan-4-yl)benzyl)phthalazin-1(2H)-one | 25 |
| 4-(4-fluoro-3-(4-oxido-1-(4-(trifluoromethyl)pyridin-2-yl)-1,4-azaphosphinan-4-yl)benzyl)phthalazin-1(2H)-one | 26 |
| 4-(4-fluoro-3-(4-oxido-1-(3-(trifluoromethyl)pyridin-2-yl)-1,4-azaphosphinan-4-yl)benzyl)phthalazin-1(2H)-one | 27 |
| 4-(4-fluoro-3-(1-(3,5-difluoropyridin-2-yl)-4-oxido-1,4-azaphosphinan-4-yl)benzyl)phthalazin-1(2H)-one | 28 |
| 4-(4-fluoro-3-(1-(5-fluoropyridin-2-yl)-4-oxido-1,4-azaphosphinan-4-yl)benzyl)phthalazin-1(2H)-one | 29 |
| 4-(4-fluoro-3-(4-oxido-1-(quinazolin-2-yl)-1,4-azaphosphinan-4-yl)benzyl)phthalazin-1(2H)-one | 30 |
| 4-(4-fluoro-3-(4-oxido-1-(6-(trilluoromethyl)pyridin-2-yl)-1,4-azaphosphinan-4-yl)benzyl)phthalazin-1(2H)-one | 31 |
| 4-(4-fluoro-3-(4-oxido-1-(thiazol-2-yl)-1,4-azaphosphinan-4-yl)benzyl)phthalazin-1(2H)-one | 32 |
| 4-(4-fluoro-3-(4-oxido-1-(thiadiazol-2-yl)-1,4-azaphosphinan-4-yl)benzyl)phthalazin-1(2H)-one | 33 |
| 4-(4-fluoro-3-(4-oxido-1-(3-(acetyl)pyridin-2-yl)-1,4-azaphosphinan-4-yl)benzyl)phthalazin-1(2H)-one | 34 |
| (±)-4-(4-fluoro-3-(4-oxido-1-(3-(1-hydoxyethyl)pyridin-2-yl)-1,4-azaphosphinan-4-yl)benzyl)phthalazin-1(2H)-one | 35 |
| 4-(4-fluoro-3-(4-oxido-1-(5-(fluoro)pyrimidin-2-yl)-1,4-azaphosphinan-4-yl)benzyl)phthalazin-1(2H)-one | 35 |
| 4-(4-fluoro-3-(4-oxido-1-(5-(chloro)pyrimidin-2-yl)-1,4-azaphosphinan-4-yl)benzyl)phthatazin-1(2H)-one | 36 |
| 4-(4-fluoro-3-(4-oxido-1-(5-(n-propyl)pyrimidin-2-yl)-1,4-azaphosphinan-4-yl)benzyl)phthalazin-1(2H)-one | 37 |
| 4-(3-(1-cyclopropyl-4-oxido-1,4-azaphosphinan-4-yl)-4-fluorobenzyl)phthalazin-1(2H)-one | 38 |
| 4-(3-(1-cyclobutyl-4-oxido-1,4-azaphosphinan-4-yl)-4-fluorobenzyl)phthalazin-1-(2H)-one | 39 |
| 4-(4-fluoro-3-(1-methyl-4-oxido-1,4-azaphosphinan-4-yl)benzyl)phthalazin-1(2H)-one | 40 |
| 4-(3-(1-ethyl-4-oxido-1,4-azaphosphinan-4-yl)-4-fluorobenzyl)phthalazin-1(2H)-one | 41 |
| 4-(4-fluoro-3-(1-isopropyl-4-oxido-1,4-azaphosphinan-4-yl)benzyl)phthalazin-1(2H)-one | 42 |
| 4-(3-(1-(cyclopropylmethyl)-4-oxido-1,4-azaphosphinan-4-yl)-4-fluorobenzyl)phthalazin-1(2H)-one | 43 |
| 4-(4-fluoro-3-(1-isobutyl-4-oxido-1,4-azapliosphinan-4-yl)benzyl)phthalazin-1(2H)-one | 44 |
| 4-(4-fluoro-3-(4-oxido-45propyl-1,4-azaphosphinan-4-yl)benzyl)phthalazin-1(2H)-one | 45 |
| 4-(4-fluoro-3-(1-neopentyl-4-oxido-1,4-azaphosphinan-4-yl)benzyl)phthalazin-1(2H)-one | 46 |
| 4-(4-fluoro-3-(1-neopentyl-4-oxido-1,4-azaphosphinan-4-yl)benzyl)phthalazin-1(2H)-one | 47 |
| 4-(4-fluoro-3-(1-isopentyl-4-oxido-1,4-azaphosphinan-4-yl)benzyl)phthalazin-1(2H)-one | 48 |
| 4-(3-(1-cyclopropyl-4-oxido-1,4-azaphosphinan--4-yl)-4-fluorobenzyl)phthalazin-1(2H)-one | 49 |
| 4-[[4-fluoro-3-(4-methyl-4-oxo-1,4-azaphosphinane-1-carbonyl)phenyl]methyl]-2H-phthalazin-1-one | 50 |
| 4-[[4-fluoro-3-(4-ethyl-4-oxo-1,4-azaphosphinane-1-carbonyl)phenyl]methyl]-2H-phthalazin-1-one | 51 |
| 4-[[4-fluoro-3-(4-isopropyl-4-oxo-1,4-azaphosphinane-1-carbonyl)phenyl]methyl]-2H-phthalazin-1-one | 52 |
| 4-[[4-fluoro-3-(4-ethoxyl-4-oxo-1,4-azaphosphinane-1-carbonyl)phenyl]methyl]-2H-phthalazin-1-one | 53 |
| 4-(3-(1-cyclopropyl-4-oxido-1,4-azaphosphinan-4-yl)-4-fluorobenzyl)-7-fluorophthalazin-1(2H)-one | 54 |
| 4-[(3-(1-cyclopropyl-4-oxido-1,4-azaphosphinan-4-yl)-4-fluorophenyl)dideuteromethyl]-7-fluorophthalazin-1(2H)-one | 55 |
| 4-(4-fluoro-3-(4-oxido-1-(pyrimidin-2-yl)-1,4-azaphosphinan-4-yl)benzyl)-7-fluorophthalazin-1(2H)-one | 56 |
| 4-[(4-fluoro-3-(4-oxido-1-(pyrimidin-2-yl)-1,4-azaphosphinan-4-yl)phenyl)dideuteromethyl]-7-fluorophthalazin-1(2H)-one | 57 |

TABLE 1-continued

Exemplary compounds

| Compound | Example No. |
|---|---|
| (±)-4-[(3-(1-cyclopropyl-4-oxido-1,4-azaphosphinan-4-yl)-4-fluoro-1-phenyl)(hydroxymethl)]phthalazin-1(2H)-one | 58 |
| (±)-4-{[4-fluoro-3-(4-oxido-1-(pyrimidin-2-yl)-1,4-azaphosphinan-4-yl)phenyl)](hydroxymethyl)]-7-fluorophthalazin-1(2H)-one | 59 |

Pharmaceutical Compositions

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form, suitable for oral, buccal, parenteral, nasal, topical or rectal administration or a form suitable for administration by inhalation.

The present invention embraces the free base of compounds detailed herein, such as a compound of the formula (I), (II), (III), (IV), (V) or any variations thereof, as well as the pharmaceutically acceptable salts and stereoisomers thereof. The compounds of the present invention can be protonated at the N atom(s) of an amine and/or N containing heterocycle moiety to form a salt. The term "free base" refers to the amine compounds in non-salt form. The encompassed pharmaceutically acceptable salts not only include the salts exemplified for the specific compounds described herein, but also all the typical pharmaceutically acceptable salts of the free form of compounds detailed herein, such as a compound of the formula (I), (II) (III), (IV), (V) or any variations thereof. The free form of the specific salt compounds described may be isolated using techniques known in the art. For example, the free form may be regenerated by treating a salt with a suitable dilute aqueous base solution such as dilute aqueous NaOH, potassium carbonate, ammonia and sodium bicarbonate. The free base forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic, organic acid or polymeric acid. For example, conventional non-toxic salts include those derived from inorganic acids such as hydrochloric acid, hydrobromic acid, hydroiodic acid, sulfuric acid, sulfurous acid, sulfamic acid, phosphoric acid, phosphorous acid, nitric acid and the like, as well as salts prepared from organic acids such as acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxy-benzoic acid, fumaric acid, toluenesulfonic acid, methanesulfonic acid, ethanesulfonic acid, ethylene disulfonic acid, oxalic acid, isethionic acid, palmitic acid, gluconic acid c, ascorbic acid, phenylacetic acid, aspartic acid, cinnamic acid, pyruvic acid, valeric acid, trifluoroacetic acid and the like. Examples of suitable polymeric salts include those derived from the polymeric acids such as tannic acid and carboxymethyl cellulose. Preferably, a pharmaceutically acceptable salt of this invention contains 1 equivalent of a compound detailed herein, such as a compound of the formula (I), (II), (III), (IV), (V) or any variations thereof, and 1, 2 or 3 equivalent of an inorganic or organic acid. In some embodiments, the pharmaceutically acceptable salt contains 1 equivalent of a compound detailed herein, such as a compound of the formula (I), (II), (III), (IV), (V) or any variations thereof, and 1 equivalent of an inorganic or organic acid.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic, manganous, potassium, sodium, zinc salts, and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, lysine, betaine caffeine, choline, ethylamine, diethylamine, 2-diethylaminoethanol, 2-dimethylaminoethanol, ethanolamine, diethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine tripropylamine, tromethamine, dicyclohexylamine, butyl amine, benzyl amine, phenylbenzylamine, tromethamine, and the like.

General Synthetic Methods

Compounds of formula (I) may be prepared with procedures shown in Scheme 1, where X is selected from Cl, Br, I, OTf, and carboxylic acid; and $R^A$, $R^B$, $R^C$, $R^D$, $R^E$, and $R^F$ are as defined in formula (I) or any variations described herein.

Scheme 1

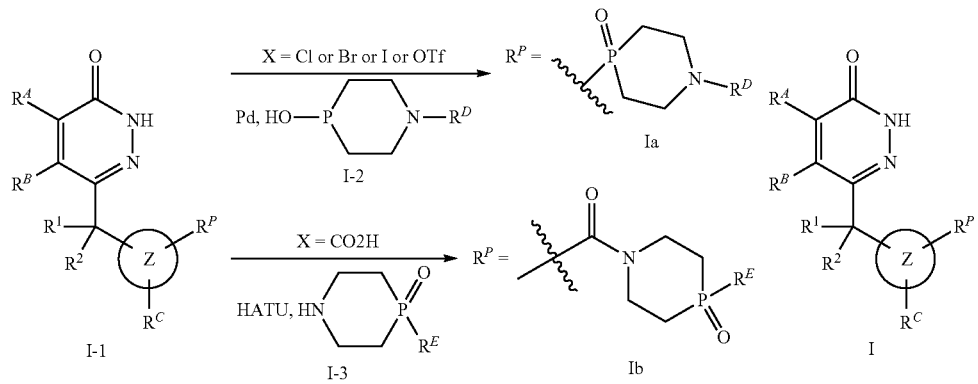

When X is selected from Cl, Br, I and OTf, compounds of formula I-1 can couple with compounds of Formula I-2 under palladium catalyzed condition to give compounds of Formula I where R is of Formula Ia.

Alternatively, when X is carboxylic acid, amide coupling of compounds of Formula I-1 and phosphorus containing amines of Formula I-3 provides compounds of the formula (I) where $R^P$ is of Formula Ib.

Compounds of Formula I-1 can be prepared according to the procedures disclosed in WO 2009/063244.

Compounds of Formula I-2 can be synthesized according to the method illustrated in Scheme 2, where R' is $C_1$-$C_6$ alkyl or aryl, and $R^D$ is as defined in formula (I) or any variations described herein.

Scheme 2

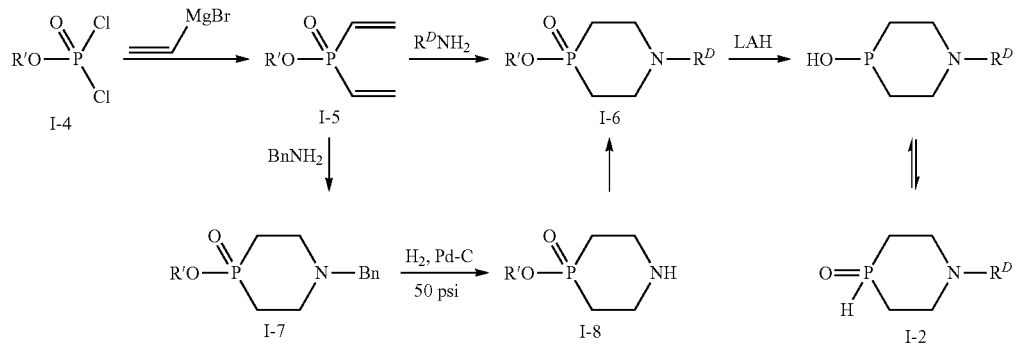

Commercially available compounds of Formula I-4 are reacted with 2 eq. of vinyl Grignard agent at low temperature to give rise to compound of Formula I-5. Michael addition of an alkylamine $R^DNH_2$ to compounds of Formula I-5 yields compounds of Formula I-6, which can be carefully reduced by lithium aluminum hydride at low temperature (−20 to 0° C.) to afford compounds of Formula I-2. Compounds of Formula I-2 exist in two tautomeric forms.

Alternatively, compounds of Formula I-5 react with benzylamine to give compounds of Formula I-7, which can be converted to compounds of Formula I-8 with palladium-on-carbon catalyzed hydrogenolysis under pressure. Compounds of Formula I-6 with a variety of $R^D$ can be prepared from compounds of Formula I-8, such as where $R^D$ is —$SO_2R^3$, —$C(O)R^4$, aryl and heteroaryl (from $S_NAr$ reaction or Pd catalyzed coupling), alkyl (via reductive amination).

Compounds of Formula I-3 can be prepared according to Scheme 3, where $R^E$ is as defined in formula (I) or any variations described herein.

Scheme 3

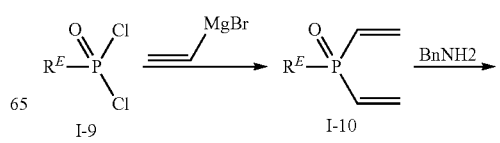

-continued

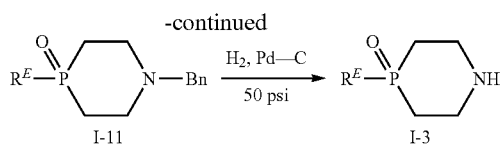

Compounds of Formula I-9 are reacted with 2 eq. of vinyl Grignard agent at low temperature to give rise to compound of Formula I-10. Michael addition with benzylamine gives compounds of Formula I-11, which can be converted to compounds of Formula I-3 with palladium-on-carbon catalyzed hydrogenolysis under pressure.

Compounds of Formula (II) may be prepared by reacting compound of Formula II-1, or a compound of Formula II-2 with hydrazine, for example, as shown in Scheme 4, where $R^F$, $R^C$, and $R^P$ are as defined in formula (I) or any variations described herein.

Scheme 4

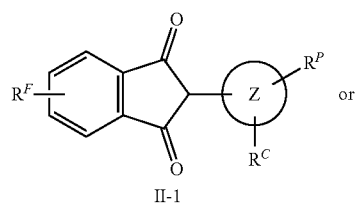
II-1 or

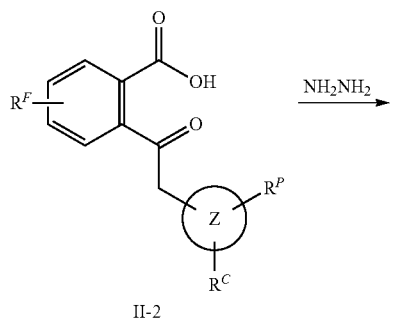
II-2

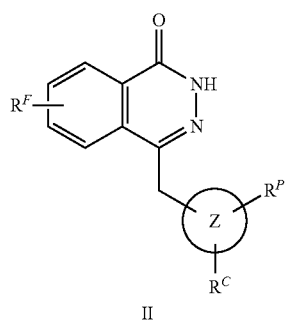
II

The reaction is generally carried out in refluxing a hydrazine source, such as hydrazine monohydrate or hydrazine hydrate for 1-24 hours.

Compounds of Formula III may be prepared according to Scheme 5, where R" is a $C_1$-$C_6$ alkyl (e.g., Me, Et, i-Pr), and $R^F$, $R^C$, and $R^P$ are as defined in formula (I) or any variations described herein.

Scheme 5

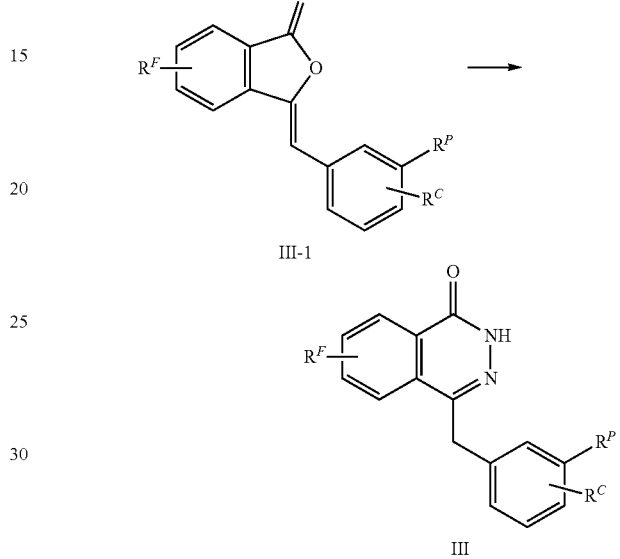
III

A compound of the formula (III) can be prepared by reacting a compound of Formula III-1 with a hydrazine source, such as hydrazine monohydrate or hydrazine hydrate, generally by refluxing for 1-24 hours.

Compounds of Formula III-1 may be synthesized by reacting a compound of Formula III-2 and a compound of Formula III-3. The reaction is generally carried out with a base, such as triethylamine or lithium hexamethylsilazide in a solvent, such as THF, at temperature between –78° C. to refluxing.

Methods

Phosphorous containing heterocyclic compounds of the invention, such as phthalazin-1(2H)-one derivatives, are inhibitors of the enzyme poly(ADP-ribose)polymerase (PARP), previously known as poly(ADP-ribose)synthase or poly(ADP-ribosyl)transferase. The compounds can be used in a method of treatment of the human or animal body by therapy.

The invention provides compounds for use in the treatment or prevention of conditions which can be ameliorated by the inhibition of poly(ADP-ribose)polymerase (PARP) (see, for example, Nature Review Drug Discovery (2005) 4:421-440).

Thus, the present invention provides a compound, such as a compound of the formula (I), (II), (III), (IV), (V) or any variations thereof, for use in the manufacture of a medicament for the treatment or prevention of conditions which can be ameliorated by the inhibition of poly(ADP-ribose)polymerase (PARP).

In some aspects, the compounds are useful as monotherapies in tumors with specific defects in DNA-repair pathways, such as cancers harboring PTEN, BRCA1, and BRCA2 mutations.

In some aspects, the compounds can act as enhancers of certain DNA-damaging chemotherapeutics such as anticancer alkylating agents, topoisomerase I inhibitors and radiotherapy.

In other aspects, the compounds may be useful for reducing cell necrosis (in stroke and myocardial infarction), down regulating inflammation and tissue injury, treating retroviral infections and protecting against the toxicity of chemotherapy.

The present invention also provides a method for the treatment or prevention of conditions which can be ameliorated by the inhibition of poly(ADP-ribose)polymerase (PARP), which method comprises administration to a patient in need thereof of an effective amount of a compound detailed herein, such as a compound of the formula (I), (II), (III), (IV), (V) or any variations thereof, or a composition comprising a compound detailed herein, such as a compound of the formula (I), (TI), (III), (IV), (V) or any variations thereof. In some embodiments, the condition ameliorated by inhibition of PARP is a condition selected from the group consisting of cancer, inflammatory diseases, and ischemic conditions. In some embodiments, the cancer is a breast cancer, an ovarian cancer or a brain cancer.

Most of the biological effects of PARP relate (1) to poly(ADP-ribosylation process which influences the properties and function of the target proteins; (2) to the PAR oligomers that, when cleaved from poly(ADP-ribosylated proteins, confer distinct cellular effects: (3) to the physical association of PARP with nuclear proteins to form functional complexes: and (4) to the lowering of the cellular level of its substrate $NAD^+$ (Jagtap et al, Nature Review Drug Discovery (2005) 4:421-440).

Oxygen radical DNA damage, which is recognized by PARP, is a major contributing factor to such disease states as demonstrated by PARP inhibition (J Neurosci. Res. (1994) 39:38-46 and PNAS (1996) 93:4688-4692).

The catalytic activity of PARP-1 and PARP-2 is stimulated by DNA breakages (Tentori et al. Pharmacological Research (2005) 52:25-33). In response to DNA damage, PARP-1 and PARP-2 bind to single and double DNA nicks. Under normal physiological conditions there is minimal PARP activity; however, upon DNA damage PARP activity immediately increases up to 500-fold. Both PARP-1 and PARP-2 detect DNA strand interruptions acting as nick sensors, providing rapid signals to halt transcription, and subsequently recruit enzymes required for DNA repair at the site of damage. Since cancer therapies such as radiation and many cytotoxic agents act by inducing DNA damage, PARP inhibitors are useful as chemo- and radio-sensitizers for cancer treatment. For example, Löser et al, (Mol Cancer Ther. (2010) 9(6): 1775-87) reported PARP inhibitors as effective in radio sensitizing tumor cells.

PARP inhibitors are useful for the specific killing of BRCA-1 and BRCA-2 deficient tumors (Bryant et al, Nature (2005) 434:913-916 and Farmer et al, Nature (2005) 434: 917-921; and Cancer Biology & Therapy (2005) 4:934-936; Drew et al, 0.1 Natl. Cancer Inst (2011) 103:1-13). Breast cancers with triple-negative status, i.e. lack of expression of estrogen receptor-A and progesterone receptor, and lack of overexpression or amplification of the HER2/NEU oncogene, frequently harbor mutations in the breast cancer susceptibility gene 1 (BRCA1). Breast cancer patients with triple negative status have low response rate to currently approved cancer therapies, but they may benefit from PARP inhibitors (Alli et al, Cancer Res (2009) 69(8):3589-96; Tutt et al. The Lancet (2010) 376(9737):235-244).

In some embodiments, the invention provides a method for the treatment or prevention of cancer, comprising administration to a patient in need thereof of an effective amount of a compound detailed herein, such as a compound of the formula (I), (II), (Ill), (IV), (V) or any variations thereof, or a composition comprising a compound detailed herein, such as a compound of the formula (I), (II), (III), (IV), (V) or any variations thereof. In some embodiments, the cancer is a cancer detailed below. In some embodiments, the cancer is a breast cancer, an ovarian cancer or a brain cancer.

The compounds of this invention may also be useful for the treatment or prevention of cancer including solid tumors such as fibrosarcoma, myxosarcoma, liposarcoma, chondrosarcoma, osteogenic sarcoma, chordoma, angiosarcoma, endothelio sarcoma, lymphangiosarcoma, lymphangioendothelio sarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, skin cancer, melanoma, neuroblastoma and retinoblastoma; blood-borne cancers such as acute lymphoblastic leukemia ("ALL"), acute lymphoblastic B-cell leukemia, acute lymphoblastic T-cell leukemia, acute myeloblasts leukemia ("AML"), acute promyelocytic leukemia ("APL"), acute monoblastic leukemia, acute erythro leukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia and multiple myeloma; acute and chronic leukemias such as lymphoblastic, myelogenous, lymphocytic, myelocytic leukemias; lymphomas such as Hodgkin's disease, non-Hodgkin's Lymphoma, Multiple myeloma, Waldenstrom's macroglobulinemia, Heavy chain disease and Polycythemia vera; and CNS and brain cancers such as glioma, pilocytic astrocytoma, astrocytoma, anaplastic astrocytoma, gliobiastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor and medulloblastoma.

Thus, the present invention provides a compound, such as a compound of the formula (I), (II), (III), (IV), (V) or any variations thereof, for use in the manufacture of a medicament for the treatment or prevention of cancer, such as a cancer detailed herein (e.g., a breast cancer, an ovarian cancer or a brain cancer).

The compounds of the present invention may also be used for the treatment of cancer which is deficient in Homologous Recombination (HR) dependent DNA DSB repair activity (see WO 2006/021801). The HR dependent DNA DSB repair pathway repairs double-strand breaks (DSBs) in DNA via homologous mechanisms to reform a continuous DNA helix (Nat. Genet. (2001) 27(3):247-254). The components of the HR dependent DNA DSB repair pathway include, but are not limited to, ATM, ATR, RAD51, RAD52, RAD54, DMC1, XRCC2, XRCC3, RAD52, RAD54L, RAD54B, BRCA-1, BRCA-2, RAD50, MREI IA, NBS1, ADPRT (PARP-1), ADPRTL2, (PARP-2) CTPS, RPA, RPA1, RPA2, RPA3, XPD5, ERCC1, XPF, MMS19, RAD51, XRCCR, XRCC3, BRCA1, BRCA2, RAD50.MRE11, NB51, WRN, BLMKU70, RU80, ATM, ATRCHK1, CHK2, FANCA, FANCB, FANCC, FANCD1, FANCD2, FANCE, FANCF, FANCG, FANCC, FANCD1, FANCD2, FANCE, FANCF, FANCG, RAD1 and RAD9. Other proteins involved in the HR dependent DNA DSB repair pathway include regulatory factors such as EMSY (Cell (2003) 115:523-535).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the FIR dependent DNA DSB repair pathway may be abolished in the one or more cancer cells of an individual having a cancer which is deficient in HR dependent DNA DSB repair. Components of the HR dependent DNA DSB repair pathway are well characterized in the art (see for example, Science (2001) 291: 1284-1289) and include the components listed above.

In some embodiments, the invention provides a method for the treatment or prevention of cancer which is deficient in HR dependent DNA DSB repair activity, comprising administration to a patient in need thereof of an effective amount of a compound detailed herein, such as a compound of the formula (I), (II), (III), (IV), (V) or any variations thereof, or a composition comprising a compound detailed herein, such as a compound of the formula (I), (II), (III), (IV), (V) or any variations thereof.

The present invention also provides a compound, such as a compound of the formula (I), (II), (III), (IV), (V) or any variations thereof, for use in the manufacture of a medicament for the treatment or prevention of a cancer which is deficient in HR dependent DNA DSB repair activity.

Some cancer cells have a BRCA1 and/or BRCA2 deficient phenotype. Cancer cells with this phenotype may be deficient in BRCA1 and/or BRCA2, i.e., expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Cell (2003) 115:523-535). BRCA1 and BRCA2 are known tumor suppressors whose wild-type alleles are frequently lost in tumors of heterozygous carriers (Oncogene, (2002) 21(58): 8981-93; Trends Mol. Med., (2002) 8(12):571-6). The association of BRCA1 and/or BRCA2 mutations with breast cancer has been well-characterized (Exp Clin. Cancer Res., (2002) 21 (S Suppl.):9-12). Amplification of the EMSY gene, which encodes a BRCA-2 binding factor, is also known to be associated with breast and ovarian cancer. Carriers of mutations in BRCA-1 and/or BRCA-2 are also at elevated risk of cancer of the ovary, prostate and pancreas. The detection of variation in BRCA-1 and BRCA-2 is well-known in the art and is described, for example in Genet. Test (1992) 1:75-83; Cancer Treat Res (2002) 107:29-59; Neoplasm (2003) 50(4):246-50; Ceska Gynekol (2003) 68(1): 11-16). Determination of amplification of the BRCA-2 binding factor EMSY is described in Cell 115:523-535. PARP inhibitors have been demonstrated as being useful for the specific killing of BRCA-1 and BRCA-2 deficient tumors (Nature (2005) 434:913-916 and 917-920).

In some embodiments, the invention provides a method for the treatment or prevention of BRCA-1 or BRCA-2 deficient tumors, comprising administration to an individual in need thereof of an effective amount of a compound detailed herein, such as a compound of the formula (I), (II), (III), (IV), (V) or any variations thereof or a composition comprising a compound detailed herein, such as a compound of the formula (I), (II), (III), (IV), (V) or any variations thereof.

Thus, the present invention provides a compound such as a compound of the formula (I), (II), (III), (IV), (V) or any variations thereof, for use in the manufacture of a medicament for the treatment or prevention of BRCA-1 or BRCA-2 deficient tumors.

Some cancer cells have a mutated tumor suppressor gene, phosphatase and tensin homolog (PTEN). PTEN deficiency causes a homologous recombination (HR) defect in human tumor (Mendes-Pereira et al, EMBO Mol Med, (2009) 1:315-322). PTEN is one of the most commonly mutated genes in human cancers. Recent evidence suggests that PTEN is important for the maintenance of genome stability cells (Shen et al, Cell (2007) 128:157-170). The HR deficiency caused by PTEN deficiency, sensitizes tumor cells to inhibitors of the DNA repair enzyme poly(ADP-ribose) polymerase (PARP), both in vitro and in vivo. PARP inhibitors are potentially benefit to patients with PTEN mutant tumors (Dedes et al, Sci. Transl. Med. (2010) 2(53):53ra75; and McEllin Cancer Res, (2010) 70(13):5457-64).

In some embodiments, the invention provides a method for the treatment or prevention of PTEN mutated tumors, comprising administration to an individual in need thereof of an effective amount of a compound detailed herein, such as a compound of the formula (I), (II), (III), (IV), (V) or any variations thereof or a composition comprising a compound detailed herein, such as a compound of the formula (I), (II), (III), (IV), (V) or any variations thereof.

Thus, the present invention provides a compound, such as a compound of the formula (I), (II), (III), (IV), (V) or any variations thereof, for use in the manufacture of a medicament for the treatment or prevention of PTEN mutated tumors.

PARP inhibitors are effective for the treatment of inflammation diseases (Cuzzocrea, Pharmacological Research (2005) 52:72-82 and Virág, Pharmacological Research (2005) 52:83-92).

In some embodiments, the invention provides a method for the treatment or prevention of inflammatory diseases, comprising administration to an individual in need thereof of an effective amount of a compound detailed herein, such as a compound of the formula (I), (II), (II), (IV), (V) or any variations thereof or a composition comprising a compound detailed herein, such as a compound of the formula (I), (II), (III), (IV), (V) or any variations thereof.

The compounds of the invention are useful for the treatment of inflammatory diseases, including conditions resulting from organ transplant rejection; chronic inflammatory diseases of the joints, including arthritis, rheumatoid arthritis; inflammatory bowel diseases such as ileitis, ulcerative colitis, Barrett's syndrome, and Crohn's disease; inflammatory lung diseases such as asthma, adult respiratory distress syndrome, and chronic obstructive airway disease: inflammatory diseases of the eye; chronic inflammatory diseases of the gum; inflammatory diseases of the kidney; inflammatory diseases of the skin; inflammatory diseases of the central nervous system; inflammatory diseases of the heart such as cardiomyopathy, ischemic heart disease, and atherosclerosis; as well as various other diseases that can have significant inflammatory components, including preeclampsia, chronic liver failure, brain and spinal cord trauma.

The present invention also provides a compound, such as a compound of the formula (I), (II), (III), (IV), (V) or any variations thereof, for use in the manufacture of a medicament for treating or preventing inflammatory diseases.

PARP enzymes may also act as a mediator of cell death. Its excessive activation in pathological conditions such as ischemia and reperfusion injury can result in substantial depletion of the intercellular $NAD^+$, which can lead to the impairment of several NAD dependent metabolic pathways and result in cell necrotic death (Devalaraja-Narashimha et al, Pharmacological Research (2005) 52:44-591). As a result of PARP activation, $NAD^+$ levels significantly decline, Extensive PARP activation leads to severe depletion of $NAD^+$ in cells suffering from massive DNA damage. The short half-life of poly(ADP-ribose) results in a rapid turnover rate, as once poly(ADP-ribose) is formed, it is quickly degraded by the constitutively active poly(ADP-ribose) glycohydrolase (PARG). PARP and PARG form a cycle that converts a large amount of $NAD^+$ to ADP-ribose, causing a drop of $NAD^+$ and ATP to less than 20% of the normal level, Such a scenario is especially detrimental during ischemia when deprivation of oxygen has already drastically compromised cellular energy output. Subsequent free radical production during reperfusion is assumed to be a major cause of tissue damage. Part of the ATP drop, which is typical in many organs during ischemia and reperfusion, could be linked to $NAD^+$ depletion due to poly(ADP-ribose) turnover. Thus, PARP inhibition is expected to preserve the cellular energy level thereby potentiating the survival of ischemic tissues after insult, Compounds which are inhibitors of PARP are therefore useful for treating conditions which result from PARP mediated cell death, including neurological conditions such as stroke, trauma and Parkinson's disease.

PARP inhibitors are also useful in treating acute and chronic myocardial diseases (Szabó, Pharmacological Research (2005) 52:34-43). For instance, single injections of PARP inhibitors reduced the infarct size caused by ischemia and reperfusion of the heart or skeletal muscle in rabbits (Thiemermann et al, PNAS (1997) 94:679-683). Similar findings have also been reported in pigs (Eur. J. Pharmacol. (1998) 359:143-150 and Ann. Thorac. Surg. (2002) 73:575-581), in dogs (Shock. (2004) 21:426-32), and in rats (Bartha et al, J Cardiovasc. Pharmacol. 2008 September; 52(3):253-61). PARP inhibitors were effective for treating certain vascular diseases, septic shock, ischemic injury and neurotoxicity (Biochim. Biophys. Acta (1989) 1014:1-7; J Clin. Invest. (1997) 100: 723-735).

In some embodiments, the invention provides a method for the treatment or prevention of ischemic conditions and for the prevention or treatment of stroke, comprising administration to an individual in need thereof of an effective amount of a compound detailed herein, such as a compound of the formula (I), (II), (II), (IV), (V) or any variations thereof or a composition comprising a compound detailed herein, such as a compound of the formula (I), (II), (III), (IV), (V) or any variations thereof.

The compounds of the instant invention may also be useful in the treatment or prevention of ischemic conditions, including those resulting from organ transplantation, such as stable angina, unstable angina, myocardial ischemia, hepatic ischemia, mesenteric artery ischemia, intestinal ischemia, critical limb ischemia, chronic critical limb ischemia, cerebral ischemia, acute cardiac ischemia, ischemia kidney disease, ischemic liver disease, ischemic retinal disorder, septic shock, and an ischemic disease of the central nervous system, such as stroke or cerebral ischemia.

Thus, the present invention provides a compound, such as a compound of the formula (I), (II), (III), (IV), (V) or any variations thereof, for use in the manufacture of a medicament for the treatment or prevention of ischemic conditions, and for the treatment or prevention of stroke.

In some embodiments, the invention provides a method for the treatment or prevention of reperfusion injuries, comprising administration to an individual in need thereof of an effective amount of a compound detailed herein, such as a compound of the formula (I), (II), (III), (IV), (V) or any variations thereof or a composition comprising a compound detailed herein, such as a compound of the formula (I), (II), (III), (IV), (V) or any variations thereof.

The compounds of the instant invention may also be useful in the treatment or prevention of reperfusion injuries, resulting from naturally occurring episodes and during a surgical procedure, such as intestinal reperfusion injury; myocardial reperfusion injury; reperfusion injury resulting from cardiopulmonary bypass surgery, aortic aneurysm repair surgery, carotid endarterectomy surgery, or hemorrhagic shock; and reoxygenation injury resulting from transplantation of organs.

Thus, the present invention provides a compound, such as a compound of the formula (I), (II), (III), (IV), (V) or any variations thereof, for use in the manufacture of a medicament for the treatment or prevention of reperfusion injuries.

The compounds of the instant invention may also be useful for the treatment or prevention of chronic or acute renal failure.

In some embodiments, the invention provides a method for the treatment or prevention of renal failure, comprising administration to an individual in need thereof of an effective amount of a compound detailed herein, such as a compound of the formula (I), (II), (III), (IV), (V) or any variations thereof or a composition comprising a compound detailed herein, such as a compound of the formula (I), (II), (III), (IV), (V) or any variations thereof.

Thus, the present invention provides a compound, such as a compound of the formula (I), (II), (III), (IV), (V) or any variations thereof, for use in the manufacture of a medicament for the treatment or prevention of renal failure.

PARP inhibition can efficiently block retroviral infection of mammalian cells. Such inhibition of recombinant retroviral vector infections occurs in various different cell types (J Virology, (1996) 70(6):3992-4000).

In some embodiments, the invention provides a method for the treatment or prevention of an retroviral infection, comprising administration to an individual in need thereof of an effective amount of a compound detailed herein, such as a compound of the formula (I), (II), (III), (IV), (V) or any variations thereof or a composition comprising a compound detailed herein, such as a compound of the formula (I), (II), (III), (IV), (V) or any variations thereof.

The invention also provides a compound, such as a compound of the formula (I), (II), (III), (IV), (V) or any variations thereof, for use in the manufacture of a medicament for the treatment or prevention of a retroviral infection.

PARP inhibitors have also found potential application in the treatment or prevention of autoimmune diseases such as Type I diabetes and diabetic complications, as demonstrated by in vitro and in vivo experiments (Szabó, Pharmacological Research (2005) 52:60-71).

In some embodiments, the invention provides a method for the treatment or prevention of an autoimmune disease (e.g., Type I diabetes), comprising administration to an individual in need thereof of an effective amount of a compound detailed herein, such as a compound of the formula (I), (II), (III), (IV), (V) or any variations thereof or a composition comprising a compound detailed herein, such as a compound of the formula (I), (II), (III), (IV), (V) or any variations thereof.

The invention also provides a compound, such as a compound of the formula (I), (II), (III), (IV), (V) or any variations thereof, for use in the manufacture of a medicament for the treatment or prevention of an autoimmune disease (e.g., Type I diabetes).

PARP plays an important role in controlling telomere function (Nature Gen., (1999) 23:76-80), and thus PARP inhibition may delay the onset of aging characteristics in human fibroblasts (Biochem. Biophys. Res. Comm. (1994) 201(2):665-672 and Bürkle et al, Pharmacological Research (2005) 52:93-99).

In some embodiments, the invention provides a method for delaying the onset of aging, comprising administration to an individual in need thereof of an effective amount of a compound detailed herein, such as a compound of the formula (I), (II, (IT), (IV), (V) or any variations thereof or a composition comprising a compound detailed herein, such as a compound of the formula (I), (II), (III), (IV), (V) or any variations thereof.

The invention also provides a compound, such as a compound of the formula (I), (II), (III), (IV), (V) or any variations thereof, for use in the manufacture of a medicament for delaying the onset of aging.

In another aspect, the invention provides a method for inhibiting PARP-1 enzyme activity, comprising contacting PARP-1 enzyme with a compound detailed herein, such as a compound of the formula (I), (II), (III), (IV), (V) or any variations thereof. In some embodiments. In some embodiments, the compound is capable of inhibiting PARP-1 enzymatic activity with an $IC_{50}$ of less than about 100 nM. In some embodiments, the compound has a PARP-1 enzyme inhibition $IC_{50}$ of less than about 1,000 nM, less than about 750 nM, less than about 500 nM, less than about 250 nM, less than about 150 nM, less than about 100 nM, less than about 50 nM, less than about 10 nM, or less than about 1 nM, as measured using the HT Universal Colorimetric PARP Assay Kit.

In another aspect, the invention provides a method for inhibiting intracellular poly(ADP-ribose) formation comprising contacting the cell with a compound detailed herein, such as a compound of the formula (I), (II), (III), (IV), (V) or any variations thereof. In some embodiments, the compound is capable of inhibiting intracellular poly(ADP-ribose) formation with an $EC_{50}$ of less than about 100 nM. In some embodiments, the compound is capable of inhibiting intracellular poly(ADP-ribose) formation with an $EC_{50}$ of less than about 1,000 nM, less than about 750 nM, less than about 500 nM, less than about 250 nM, less than about 150 nM, less than about 100 nM, less than about 50 nM, less than about 10 nM, or less than about 1 nM in C41 cells.

The compounds of this invention are capable of penetrating intact cell membrane and inhibiting intracellular PARP enzymatic activities, thus inhibiting poly(ADP-ribose) formation catalyzed by PARP.

Administration

The compounds of this invention, such as a compound of the formula (I), (II), (III), (IV), (V) or any variations thereof, may be administered to mammals, preferably humans, either alone or in combination with pharmaceutically acceptable carriers, excipients, diluents, adjuvants, fillers, buffers, stabilizers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly). The subject may be an animal or a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcelluose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame, Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compound, such as a compound of the formula (I), (II), (III), (IV), (V) or any variations thereof, may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol. When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. Where the active compound is a salt, an ester, prodrug, or the like, the amount administered is calculated on the basis of the parent compound and so the actual weight to be used is increased proportionately.

Combination Therapy

The compounds of the invention, such as a compound of the formula (I), (II), (III), (IV), (V) or any variations thereof, are also useful in combination with other anti-cancer agents or chemotherapeutic agents.

PARP inhibitors can enhance the efficacy of anticancer drugs (Tentori et al, Pharmacological Research (2005) 52:25-33), including platinum compounds such as cisplatin and carboplatin (Cancer Chemother. Pharmacol (1993) 33:157-162 and Mol Cancer Ther (2003) 2:371-382). PARP inhibitors have been shown to increase the antitumor activity of topoisomerase I inhibitors such as Irinotecan and Topotecan (Mol Cancer Ther (2003) 2:371-382; and Clin. Cancer Res (2000) 6:2860-2867; Daniel et al, Clin. Cancer Res (2009) 15(4):1241-1249) and this has been demonstrated in in vivo models (J Natl. Cancer Inst. (2004) 96:56-67).

PARP inhibitors also can restore susceptibility to the cytotoxic and antiproliferative effects of temozolomide (TMZ) (Donawho et al, Clin. Cancer Res (2007) 13(9): 2728-2737; Daniel et al, Clin. Cancer Res (2009) 15(4): 1241-1249); Menear et al, J. Med. Chem. (2008) 51:6581-6591).

PARP inhibitors can act as radiation sensitizers. PARP inhibitors sensitize radiation therapy in (hypoxic) tumor cells and enhance cell killing by preventing tumor cells from recovering from potentially lethal (Br. J. Cancer (1984) 49(Suppl. VI):34-42; and Int. J. Radial Biol. (1999) 75:91-100) and sub-lethal (Clin. Oncol, (2004) 16(1):29-39) damage of DNA after radiation therapy. The mechanism is presumably due to their ability to prevent DNA strand break rejoining and by affecting several DNA damage signaling pathways.

The compounds of this invention may be useful as chemo- and radiosensitizers for cancer treatment. They are useful for the treatment of mammals who have previously undergone or are presently undergoing treatment for cancer. Such previous treatments include prior chemotherapy, radiation therapy, surgery or immunotherapy, such as cancer vaccines.

In some embodiments, provided is a combination comprising a compound, such as a compound of the formula (I), (II), (III), (IV), (V) or any variations thereof, and an second anti-cancer agent for simultaneous, separate or sequential administration. In some embodiments, provided is a pharmaceutical composition comprising a compound, such as a compound of the formula (I), (II), (III), (IV), (V) or any variations thereof, an second anti-cancer agent, and a pharmaceutically acceptable carrier.

In some embodiments, the invention provides a combination of a compound, such as a compound of the formula (I), (II), (III), (IV), (V) or any variations thereof, a radiation therapy and another chemotherapeutic agent for simultaneous, separate or sequential administration.

The present invention also provides a compound, such as a compound of the formula (I), (II), (III), (IV), (V) or any variations thereof, for use in the manufacture of a medicament for use as an adjunct in cancer therapy or for potentiating tumor cells by combination with ionizing radiation or chemotherapeutic agents.

The present invention also provides the use of a compound, such as a compound of the formula (I), (II), (III), (IV), (V) or any variations thereof, in the manufacture of a medicament for use as an adjunct in cancer therapy or for potentiating tumor cells by combination with ionizing radiation and other chemotherapeutic agents. The compounds can also be used in combination with ionizing radiation and other chemotherapeutic agents.

The invention also provides a method of chemotherapy or radiotherapy, which method comprises administration to a patient in need thereof of an effective amount of a compound detailed herein, such as a compound of the formula (I), (II), (III), (IV), (V) or any variations thereof, or a composition comprising a compound detailed herein, such as a compound of the formula (I), (II), (III), (IV), (V) or any variations thereof, in combination with ionizing radiation or chemotherapeutic agents. The compounds can also be administered in combination with ionizing radiation and other chemotherapeutic agents.

In combination therapy, the compounds of this invention can be administered prior to, concurrently with, or subsequent to the administration of the other anticancer agent to a subject in need thereof.

The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

Examples of cancer agents or chemotherapeutic agents for use in combination with the compounds of the present invention can be found in Cancer Principles and Practice of Oncology by V. T. Devita and S. Hellman (editors), 6th edition (2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors, HIV protease inhibitors, reverse transcriptase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

Examples of "HDAC inhibitors" include suberoylanilide hydroxamic acid (SAHA), LAQ824, LBH589, PXD1OI, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY1 17081, toremifene, fulvestrant, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate, MDV3100.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, CC-difluoromethylornithine, ILX23-7553.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites, biological response modifiers; hormonal/anti-hormonal therapeutic agents, hematopoietic growth factors, monoclonal antibody targeted therapeutic agents, topoisomerase inhibitors, proteasome inhibitors and ubiquitin ligase inhibitors.

Examples of cytotoxic agents include, but are not limited to, cyclophosphamide, chlorambucil carmustine (BCNU), lomustine (CCNU), busulfan, treosulfan, sertenef, cachectin, ifosfamide, tasonermin, lonidamitne, carboplatin, altretamine, prednimustine, dibromodulcitol, ranimustine, fotemustine, nedaplatin, aroplatin, oxaliplatin, temozolornide, methyl methanesulfonate, procarbazine, dacarbazine, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX1OO. (trans, trans, trans)-bis-mu-(hexane-1,6-diamine)-mu-[diamine-platinum(II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, doxorubicin, epirubicin, pirarubicin, antineoplaston, 3'-deamino-3'-morpholino-13-deoxo-10-hydroxycarminomycin, annamycin, galarubicin, elinafide, MEN 10755 and 4-demethoxy-3-deamino-3-aziridinyl-4-methylsulphonyl-daunorubicin (see WO 00/50032). Further examples include Raf kinase inhibitors (such as Bay43-9006) and mTOR inhibitors (such as Wyeth's CCI-779 and Ariad AP23573). Further examples are inhibitors of PBK (for example LY294002). In an embodiment the compounds of this invention can be used in combination with alkylating agents.

Examples of alkylating agents include but are not limited to, nitrogen mustards: cyclophosphamide, ifosfamide, trofosfamide and chlorambucil; nitrosoureas: carmustine (BCNU) and lomustine (CCNU); alkylsulphonates: busulfan and treosulfan; triazenes; dacarbazine, procarbazine and temozolomide; platinum containing complexes: cisplatin, carboplatin, aroplatin and oxaliplatin.

Examples of anti-mitotic agents include: allocolchicine, halichondrin B, colchicine, colchicine derivative, dolstatin 10, maytansine, rhizoxin, thiocolchicine and trityl cysteine. An example of a hypoxia activatable compound is tirapazamine.

Examples of proteasome inhibitors include but are not limited to lactacystin, bortezomib, epoxomicin and peptide aldehydes such as MG 132, MG 115 and PSI.

Examples of microtubule inhibitors/microtubule-stabilizing agents include paclitaxel, vindesine sulfate, vincristine, vinblastine, vinorelbine, 3',4'-didehydro-4'-deoxy-8'-norvincaleukoblastine, docetaxol, rhizoxin, dolastatin, mivobulin isethionate, auristatin, cemadotin, RPR109881, BMS184476, vinfiunine, cryptophycin, TDX258, the epothilones (see for example U.S. Pat. Nos. 6,284,781 and 6,288, 237) and BMS 188797. Some examples of topoisomerase inhibitors are topotecan, hycaptamine, irinotecan, rubitecan, exatecan, gimetecan, difiomotecan, silyl-camptothecins, 9-aminocamptothecin, camptothecin, crisnatol, mitomycin C, lurtotecan, BNP1350, BNPII 1OO, BN80915, BN80942, etoposide phosphate, teniposide, sobuzoxane, 2'-dimethyl-amino-2'-deoxy-etoposide, GL331, asulacrine, and dimesna; non-camptothecin topoisomerase-1 inhibitors such as indolocarbazoles; and dual topoisomerase-1 and II inhibitors such as benzophenazines, XR20 115761, MLN 576 and benzopyridoindoles.

In an embodiment inhibitors of mitotic kinesins include, but are not limited to inhibitors of KSP, inhibitors of MKLP1, inhibitors of CENP-E, inhibitors of MCAK, inhibitors of Kifl4, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-I), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fiudarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, aplidine, ecteinascidin, troxacitabine, aminopterin, 5-flurouracil, alanosine, swainsonine, lometrexol, dexrazoxane, methioninase, and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin, simvastatin, pravastatin, faivastatin, and atorvastatin. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

"Angiogenesis inhibitors" refers to compounds that inhibit the formation of new blood vessels, regardless of mechanism, Examples of angiogenesis inhibitors include, but are not limited to, tyrosine kinase inhibitors, such as inhibitors of the tyrosine kinase receptors FIt-I (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal antiinflammatories (NSAIDs) like aspirin and ibuprofen as well as selective cyclooxy-genase-2 inhibitors like celecoxib and rofecoxib (PNAS (1992) 89:73'84: J Mol. Endocrinol. (1996) 16:107; Jpn. J. Pharmacol. (1997) 75:105; Cancer Res (1991)

57:1625; Cell (1998) 93:705; Intl. J. Mol. Med. (1998) 2:715; J Biol. Chem. (1999) 274:9116, steroidal antiinflammatories (such as corticosteroids, mineralocorticoids, dexamethasone, prednisone, prednisolone, methylpred, betamethasone), carboxyamidotriazole, combretastatin A-4, squalamine, thalidomide, angiostatin, troponin-1, angiotensin II antagonists (see J. Lab, Clin. Med. (1985) 105: 141-145), and antibodies to VEGF (see Nature Biotechnology (1999) 17:963-968: Kim et al (1993) Nature 362:841-844; WO 00/44777; and WO 00/61186).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by flavopiridol, CYC202 (Cyclacel), LY2606368, and BMS-387032.

"Inhibitors of cell proliferation and survival signaling pathway" refer to pharmaceutical agents that inhibit cell surface receptors and signal transduction cascades downstream of those surface receptors, Such agents include inhibitors of EGFR and or HER2 (for example gefitinib, erlotinib, lapatinib, and trastuzumab), inhibitors of IGFR, inhibitors of cytokine receptors, inhibitors of MET, inhibitors of PI3K, inhibitors of serine/threonine kinases, inhibitors of Raf kinase (for example PLX-4032 and PLX-4720), inhibitors of MEK (for example AZD6244, CI-1040 and PD-098059) and inhibitors of mTOR (for example Everolimus and Ariad AP23573). Such agents include small molecule inhibitor compounds and antibody antagonists.

"Apoptosis inducing agents" include activators of TNF receptor family members (including the TRAIL receptors).

In an embodiment the compounds of the present invention, such as a compound of the formula (I), (II), (III), (IV), (V) or any variations thereof, are useful for treating cancer in combination with one or more, particularly one, two or three agents selected from temozolomide, cisplatin, carboplatin, oxaliplatin, irinotecan and topotecan.

A compound of the instant invention may also be useful for treating cancer in combination with any one or more of the following therapeutic agents: abarelix (Plenaxis Depot®); aldesleukin (Prokine®); Aldesleukin (Proleukin®); Alemtuzumnabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®): busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®): goserelin acetate (Zoladex®); histrelin acetate (Histrelin Implant®); hydroxyurea (Hydrea®); Ibritumornab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Fenmara®); leucovorin (Wellcovorin®, Leucovorin®); Leuprolide Acetate (Eligard®); levamisole (Ergamisol®): lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®); zoledronate (Zometa®); nilotinib (Tasigna®) and dasatinib (Sprycel®).

Another embodiment of the instant invention is the use of the compounds detailed herein, such as a compound of the formula (I), (II), (III), (IV), (V) or any variations thereof, in combination with anti-viral agents (such as nucleoside analogs including ganciclovir for the treatment of cancer.

Another embodiment of the instant invention is the use of the compounds detailed herein, such as a compound of the formula (I), (II), (Iii), (IV), (V) or any variations thereof, in combination with gene therapy for the treatment of cancer. For an overview of genetic strategies to treating cancer see Hall et al (Am J Hum Genet (1997) 61:785-789) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer, a uPA/uPAR antagonist ("Adenovirus-Mediated Delivery of a uPA/uPAR Antagonist Suppresses Angiogenesis-Dependent Tumor Growth and Dissemination in Mice," Gene Therapy, August (1998) 5(8): 1105-13), and interferon gamma (J. Immunol. (2000) 164:217-222).

The compounds of the instant invention, such as a compound of the formula (I), (II), (III), (IV), (V) or any variations thereof, may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853, verapamil and PSC833 (valspodar).

A compound of the present invention, such as a compound of the formula (I), (II), (III), (IV), (V) or any variations thereof, may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABA B receptor agonists, such as baclofen, a corticosteroid such as Decadron (dexamethasone), Kenalog, Aristocort, Nasalide, Preferid, Benecorten, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

A compound of the instant invention, such as a compound of the formula (I), (II), (III), (IV), (V) or any variations thereof, may also be administered with an agent useful in the treatment of anemia. Such an anemia treatment agent is, for example, a continuous eythropoiesis receptor activator (such as epoetin alfa).

A compound of the instant invention, such as a compound of the formula (I), (II), (III), (IV), (V) or any variations thereof, may also be administered with an agent useful in the treatment of neutropenia, Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention, such as a compound of the formula (I), (II), (III), (IV), (V) or any variations thereof, may also be administered with an immunologic-enhancing drug, such as levamisole, isoprinosine and Zadaxin.

A compound of the instant invention, such as a compound of the formula (I), (II), (III), (IV), (V) or any variations thereof, may also be useful for treating or preventing cancer, including bone cancer, in combination with Xgeva™ (denosumab), or with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

The invention encompasses the use of the compounds detailed herein, such as a compound of the formula (I), (II), (III), (IV), (V) or any variations thereof, in combination with ionizing radiation and/or in combination with a second compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interferes with a cell cycle checkpoint, an apoptosis inducing agent and a bisphosphonate.

Also included in the scope of the claims is a method of treating cancer that comprises administering a therapeutically effective amount of a compound detailed herein, such as a compound of the formula (I), (II), (III), (IV), (V) or any variations thereof, in combination with radiation therapy and/or in combination with a compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interferes with a cell cycle checkpoint, an apoptosis inducing agent and a bisphosphonate.

EXAMPLES

The invention can be further understood by reference to the following examples, which are provided by way of illustration and are not meant to be limiting.

Abbreviations used in the description of the chemistry and in the Examples that follow are: AcCl (acetyl chloride); Cbz-Cl (benzylchloroformate); DCM (dichloromethane); DIPEA (diisopropylethylamine); DMF (dimethylformamide); DMSO (dimethyl sulfoxide); eq. (equivalent); EtOAc (ethyl acetate); EtOH (ethanol); mol, sieves (molecular sieves); HATU [(7-azabenzotriazol-1-yl)-tetramethyluronium hexafluorophosphate]; MeCN (acetonitrile); MeOH (methanol); MS (mass spectrometry); MW (microwave); NBS (N-bromosuccinimide); NMR (nuclear magnetic resonance); iPrOH (isopropanol): RT (room temperature); sat, aq. (saturated aqueous); $SiO_2$ (silica gel); and THF (tetrahydrofuran). t-BuOH (tert-butanol); TLC (thin layer chromatography) and TFA (trifluoroacetic acid).

Example 1

4-(3-(1-benzyl-4-oxido-1,4-azaphosphinan-4-yl)-4-fluorobenzyl)phthalazin-1(2H)-one

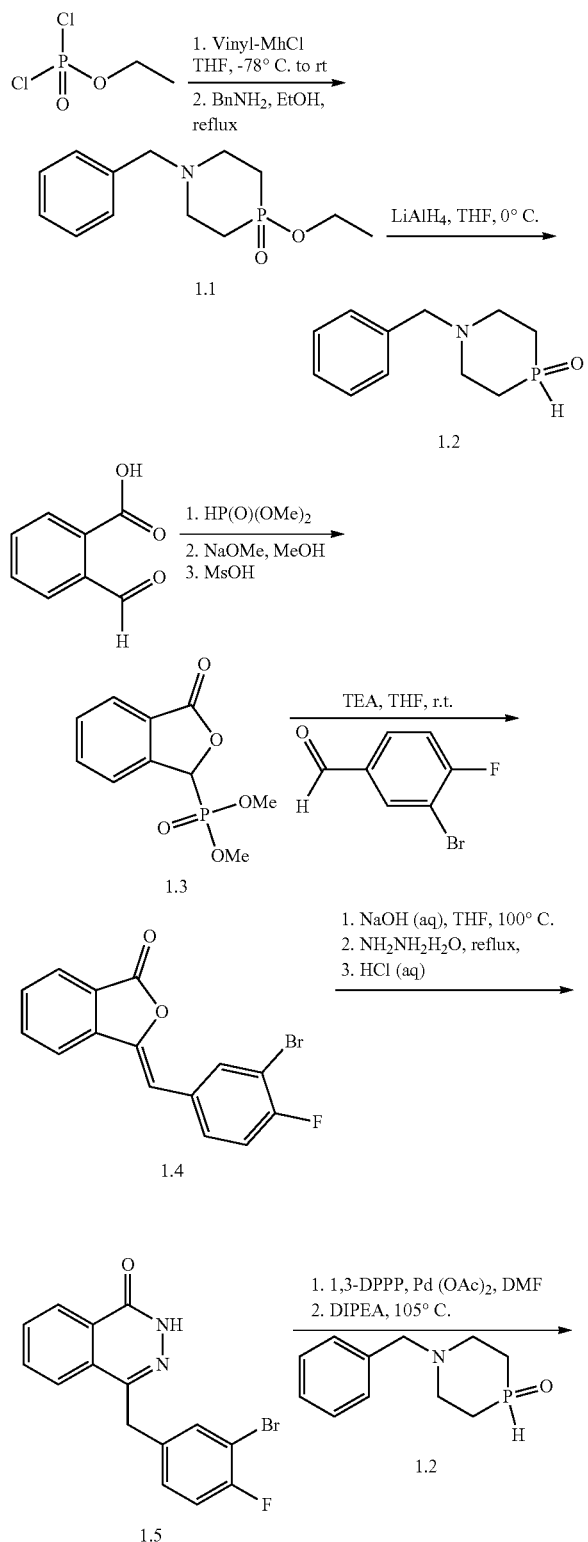

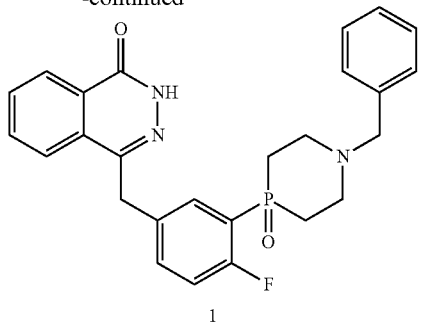

1

Step 1.1: Synthesis of 1-benzyl-4-ethoxy-1,4-azaphosphinane 4-oxide (1.1)

Compound 1.1 was made from ethyl divinylphophinate (Maier, L. *Helv. Chim. Acta* 1971, 54, 275), and followed by coupling with benzyl amine in refluxing ethanol (Dunne et al. *J. Org. Chem.*, 2005, 70, 10803-10809), as disclosed in literature.

Step 1.2: Synthesis of 1-benzyl-1,4-azaphosphinane 4-oxide (1.2)

A 2M solution of lithium aluminum hydride in THF (3.16 mL, 6.32 mmol) was added dropwise to a stirring solution of 1.1 (2.00 g, 7.90 mmol) in THF (30 mL) at 0° C. over the course of 5 min. After stirring for 45 min at 0° C., H$_2$O (300 µL) was added very slowly dropwise, followed by 15% NaOH (300 µL), then H$_2$O (900 µL). The resulting slurry was stirred for 1 h at r.t., filtered, cake washed with THF (200 mL), and the filtrates concentrated to give a crude semisolid. Column chromatography using 0-30% (gradient) MeOH/DCM afforded product 7 as a yellow oil (1.20 g, 72.6%).

Step 1.3: Synthesis of dimethyl 3-oxo-1,3-dihydroisobenzofuran-1-ylphosphonate (1.3)

Dimethyl phosphite (100 g, 0.909 mol) was added dropwisely at 0° C. under nitrogen to a stirred solution of sodium methoxide (0.909 mol) in methanol (800 ml). After completion of the addition, the reaction mixture was stirred for another 5 minutes, and 2-carboxybenzaldehyde (95.5 g, 0.64 mol) was added in 5 portions over 0.5 h. The stirred mixture was allowed to warm to room temperature, then it was stirred for another 30 minutes. The reaction was then cooled in ice, and methanesulfonic acid (96 g, 1.0 mol) was added in portions, while keep the reaction temperature under 10° C. The solvent was removed in vacuo. The residue was partitioned between DCM (1.8 L) and water (0.45 L), and the organic layer was separated, washed with water (2×450 mL) and dried (MgSO4). The solvent was removed in vacuo, the residue was triturated with ether (150 mL). The resulting solid was collected by filtration, washed with ether (30 ml) and dried in vacuo to give 1.3 (140 g) as a white crystalline solid. $^1$H NMR (250 MHz, DMSO-d6) δ (ppm): 3.65 (d, 3H), 3.85 (d, 3H), 6.4 (d, 1H), 7.75 (m, 2H), 7.85-8.05 (m, 2H); LCMS, m/z (M+H): 243.

Step 1.4: Synthesis of 3-(3-bromo-4-fluorobenzylidene)isobenzofuran-1(3H)-one (1.4)

TEA (2.11 mL, 15.17 mmol) was added dropwise to a stirring solution of 3-bromo-4-fluorobenzaldehyde (3.08 g, 15.17 mmol) and compound 1.3 (3.67 g, 15.17 mmol) in THF (40 mL) at 0° C. The reaction mixture warmed to r.t. and stirred overnight, concentrated and the residue was slurried in H₂O) (300 mL) for 1 h, filtered, washed with H₂O (2×150 mL), hexane (2×100 mL), ether (2×150 mL), and dried to give 1.4 as a white powder (3.80 g, 78.5%).

Step 1.5: Synthesis of 4-(3-bromo-4-fluorobenzyl) phthalazin-(2H)-one (1.5)

Aqueous NaOH (13 N, 4.25 mL) was added to a suspension of 1.4 (3.80 g, 11.91 mmol) in H₂O (60 mL) at rt. The mixture was stirred at 90° C. for 1 h, cooled to 70° C. added hydrazine monohydrate (8.11 mL, 116.70 mmol) slowly, and stirred at 90° C. overnight. The reaction mixture was cooled to r.t., acidified to pH ~4 with conc. HCl, filtered, washed with H₂O (2×150 mL), sonicated in ether (200 mL), filtered, washed with ether (100 mL) and dried to afford 1.5 as a white powder (3.17 g, 79.9%).

Step 1.6: Synthesis of 4-(3-(1-benzyl-4-oxido-1,4-azaphosphinan-4-yl)-4-fluorobenzyl)phthalazin-1 (2H)-one (1)

Palladium (II) acetate (386 mg, 1.72 mmol) and 1,3-bis(diphenylphosphino)propane (710 rug, 1.72 mmol) were stirred in DMF (30 mL) for 15 min, A solution of 10 (3.82 g, 11.47 mmol), 7 (2.40 g, 11.47 mmol), and DIPEA (10 mL, 57.36 mmol) in DMF (30 mL) was added and the reaction mixture stirred at 120° C. overnight. After concentrating, column chromatography using 0-10% (gradient) MeOH/DCM gave a light yellow semisolid, which was diluted in DCM (100 mL), washed with H₂O (2×100 mL), the aqueous layer was extracted with DCM (100 mL), combined organic layer was then washed with brine (100 mL), dried over MgSO₄, concentrated, sonicated in ether and filtered to afford 1 as a pale yellow solid (3.27 g, 61.8%). ¹H NMR (CD₃OD, 300 MHz) δ 8.35 (d, 1H), 7.95 (d, 1H), 7.82 (m, 3H), 7.65 (n, 1H), 7.32 (m, 3H), 7.24 (m, 3H), 4.43 (s, 2H), 3.66 (s, 2H), 2.94 (m, 8H), 2.42 (m, 2H), 2.07 (t, 2H). MS (ESI) m/z=462.2 (MH⁺).

Example 2

4-(3-(1-(cyclopentanecarbonyl)-4-oxido-1,4-azaphosphinan-4-yl)-44-fluorobenzyl)phthalazin-1(2H)-one

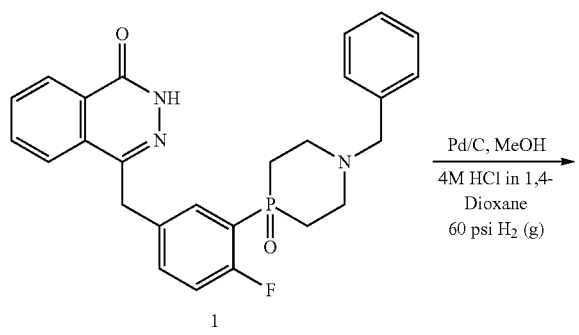

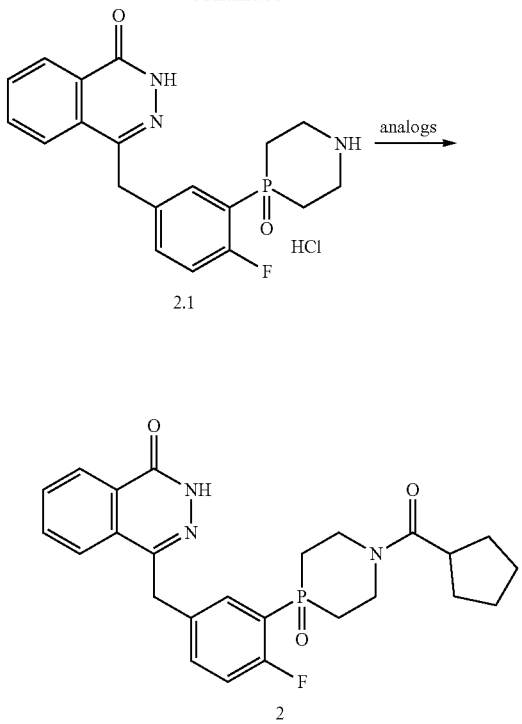

Step 2.1: Synthesis of 4-(4-fluoro-3-(4-oxido-1,4-azaphosphinan-4-yl)benzyl)phthalazin-1(2H)-one hydrochloride (2.1)

A mixture of compound 1 (1.00 g, 2.17 mmol), 4M HCl in 1,4-dioxane (2 mL), and Pd(OH)₂/C (20% wt. wet, 1 g) in MeOH (30 mL) was hydrogenated under 60 psi H₂ overnight. The reaction mixture was filtered through Celite, washed with warm MeOH (100 mL), and combined filtrates were concentrated and lyophilized to give 2.1 as a pale pink hydrochloride salt (800 mg, 90.5%). ¹H NMR (CD₃OD, 300 MHz) δ 8.35 (d, 11H), 7.95 (d, 1H), 7.84 (m, 3H), 7.66 (m, 1H), 7.22 (m, 1H), 4.40 (s, 2H), 3.21 (m, 2H), 2.91 (m, 2H), 2.40 (m, 3H), 2.09 (m, 2H). LCMS (ESI+) m/z=372.1 (M+H).

Step 2.2: Synthesis of 4-(3-(1-(cyclopentanecarbonyl)-4-oxido-1,4-azaphosphinan-4-yl)-4-fluorobenzyl)phthalazin-1 (2H)-one (2)

Cyclopentanecarbonyl chloride (16 μL, 0.13 mmol) was added to a solution of 2.1 (43.9 mg, 0.11 mmol) and DIPEA (28 μL, 0.16 mmol) in DCM (1 mL) at 0° C. and the reaction mixture was stirred for 1 h. The concentrated residue was subjected to prep-TLC using 10% MeOH/DCM and lyophilized to give 2 as a white powder (38 mg, 75.5%). 1H NMR (CD₃OD, 300 MHz) δ 8.35 (d, 1H), 7.95 (d, 1H), 7.84 (m, 3H), 7.66 (m, 1H), 7.22 (m, 1H), 4.55 (m, 1H), 4.43 (s, 2H), 4.32 (m, 1H), 3.91 (m, 1H), 3.50 (m, 1H), 3.14 (m, 1H), 2.38 (m, 2H), 2.15 (m, 2H), 1.76 (m, 8H). LCMS (ESI+) m/z=468.2 (M+H).

Examples 3-10

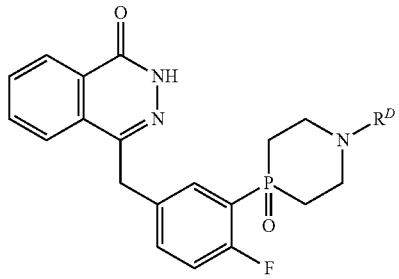

| Example No. | R^D | Chemical Name | $^1$H NMR (300 MHz) (Solvent) δ ppm | LCMS m/z (M + H) |
|---|---|---|---|---|
| 3 | ![cyclopropanecarbonyl] | 4-(3-(1-cyclopropanecarbonyl)-4-oxido-1,4-azaphosphinan-4-yl)-4-fluorobenzyl)phthalazin-1(2H)-one | (DMSO-d6) 12.58 (s, 1H), 8.24 (d, 1H), 8.00 (d, 1H), 7.82 (m, 3H), 7.62 (m, 1H), 7.28 (m, 1H), 4.39 (s, 2H), 4.24 (m, 2H), 3.85 (m, 1H), 2.08 (m, 6H), 0.74 (m, 4H). | 441 |
| 4 | ![cyclobutanecarbonyl] | 4-(3-(1-cyclobutanecarbonyl)-4-oxido-1,4-azaphosphinan-4-yl)-4-fluorobenzyl)phthalazin-1(2H)-one | (DMSO-d6) 12.58 (s, 1H), 8.24 (d, 1H), 8.00 (d, 1H), 7.82 (m, 3H), 7.60 (m, 1H), 7.27 (m, 1H), 4.38 (s, 2H), 4.17 (m, 2H), 3.64 (m, 3H), 2,08 (m, 8H), 1.74 (m, 2H). | 455 |
| 5 | ![3,3-dimethylbutanoyl] | 4-(3-(1-(3,3-dimethylbutanoyl)-4-oxido-1,4-azaphosphinan-4-yl)-4-fluorobenzyl)phthalazin-1(2H)-one | (DMSO-d6) 12.58 (s, 1H), 8.24 (d, 1H), 8.00 (d, 1H), 7.82 (m, 3H), 7.61 (m, 1H), 7.28 (m, 1H), 4.38 (m, 2H), 4.28 (m, 2H), 4.00 (m, 2H), 3.70 (m, 2H), 3.40 (m, 2H), 2.32 (m, 4H), 1.00 (s, 9H). | 471 |
| 6 | ![3,3-difluoropyrrolidine-1-carbonyl] | 4-(3-(1-(3,3-difluoropyrrolidine-1-carbonyl)-4-oxido-1,4-azaphosphinan-4-yl)-4-fluorobenzyl)phthalazin-1(2H)-one | (CD$_3$OD) 8.35 (d, 1H), 7.95 (d, 1H), 7.84 (m, 3H), 7.67 (m, 1H), 7.22 (m, 1H), 4.44 (s, 2H), 3.66 (m, 8H), 2.40 (m, 4H), 2.10 (m, 2H), 1.19 (t, 1H). | 506 |
| 7 | ![tetrahydrofuran-2-carbonyl] | 4-(4-fluoro-3-(4-oxido-1-(tetrahydrofuran-2-carbonyl)-1,4-azaphosphinan-4-yl)benzyl)phthalazin-1(2H)-one | (DMSO-d6) 12.58 (s, 1H), 8.26 (d, 1H), 8.00 (d, 1H), 7.84 (m, 3H), 7.59 (m, 1H), 7.28 (m, 1H), 4.38 (s, 2H), 3.63 (m, 2H), 3.46 (m, 2H), 2.23 (m, 3H), 2.00 (m, 3H), 1.75 (m, 5H). | 471 |
| 8 | ![pivaloyl] | 4-(4-fluoro-3-(4-oxido-1-pivaloyl-1,4-azaphosphinan-4-yl)benzyl)phthalazin-1(2H)-one | (CDCl$_3$) 10.22 (s, 1H), 8.44 (d, 1H), 7.98 (m, 1H), 7.76 (m, 3H), 7.47 (m, 1H), 7,05 (m, 1H), 4.67 (m, 2H), 4.34 (s, 2H), 3.67 (m, 2H), 2.32 (m, 2H), 2.06 (m, 2H), 1.35 (s, 9H). | 457 |
| 9 | ![N,N-dimethylcarboxamide] | 4-(2-fluoro-5-((4-oxo-3,4-dihydrophthalazin-1-yl)methyl)phenyl)-N,N-dimethyl-1,4-azaphosphinane-1-carboxamide 4-oxide | (CDCl$_3$) 10.14 (s, 1H), 8.44 (d, 1H), 7.96 (m, 1H), 7.80 (m, 3H), 7.45 (m, 1H), 7.07 (m, 1H), 4.34 (s, 2H), 3.96 (m, 2H), 3.65 (m, 2H), 2.89 (s, 6H), 2.42 (m, 2H), 2.03 (m, 2H). | 443 |
| 10 | ![pyrrolidinecarbonyl] | 4-(4-fluoro-3-(4-oxido-1-pivaloyl-1,4-azaphosphinan-4-yl)benzyl)phthalazin-1(2H)-one | (DMSO-d$_6$, 300 MHz) 12.58 (s, 1H), 8.26 (d, 1H), 8.00 (d, 1H), 7.84 (m, 3H), 7.59 (m, 1H), 7.28 (m, 1H), 4.38 (s, 2H), 3.67 (m, 2H), 3.44 (m, 2H), 3.27 (m, 4H), 2.23 (m, | 469 |

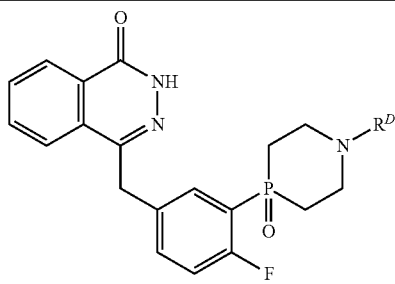

| Example No. | $R^D$ | Chemical Name | $^1$H NMR (300 MHz) (Solvent) δ ppm | LCMS m/z (M + H) |
|---|---|---|---|---|
| | | | 2H), 2.00 (m, 2H), 1.75 (m, 4H). | |

Compounds of Examples 3-10 were prepared using the appropriate starting materials and reagents according to the same procedures as in Example 2.

Example 11

(E/Z)—N-(azetidin-1-yl(4-(2-fluoro-5-((4-oxo-3,4-dihydrophthalazin-1-yl)methyl)phenyl)-4-oxido-1,4-azaphosphinan-1-yl)methylene)cyanamide

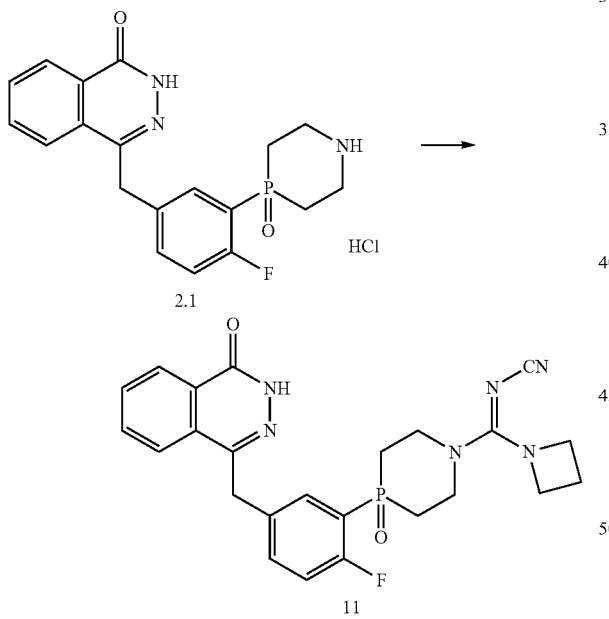

Synthesis of (E/Z)—N-(azetidin-1-yl(4-(2-fluoro-5-((4-oxo-3,4-dihydrophthalazin-1-yl)methyl)phenyl)-4-oxido-1,4-azaphosphinan-1-yl)methylene)cyanamide (11)

Dimethyl N-cyanodithioiminocarbonate (132 mg, 0.90 mmol), DIPEA (157 μL, 0.90 mmol), and 2.1 (85 mg, 0.18 mmol) were mixed together in isopropanol (2 mL) and stirred at 100° C. overnight. After cooling to r.t., azetidine hydrochloride (169 mg, 1.80 mmol) and DIPEA (157 μL, 0.90 mmol) were added and the mixture was stirred at 110° C. overnight. The concentrated residue was subjected to prep-TLC using 10% MeOH/DCM and lyophilized to give 11 as a white powder (40 mg, 46.3%). $^1$H NMR (DMSO-$d_6$, 300 MHz) δ 12.55 (s, 1H), 8.24 (d, 1H), 8.00 (d, 1H), 7.89 (m, 1H), 7.78 (m, 21H), 7.61 (m, 1H), 7.28 (m, 1H), 4.38 (s, 1H), 4.24 (t, 2H), 3.70 (m, 2H), 2.20 (m, 8H). LCMS (ESI+) m/z=479.0 (M+H).

Example 12

4-(4-fluoro-3-(4-oxido-1-(pyrimidin-2-yl)-1,4-azaphosphinan-4-yl)benzyl)phthalazin-1(2H)-one

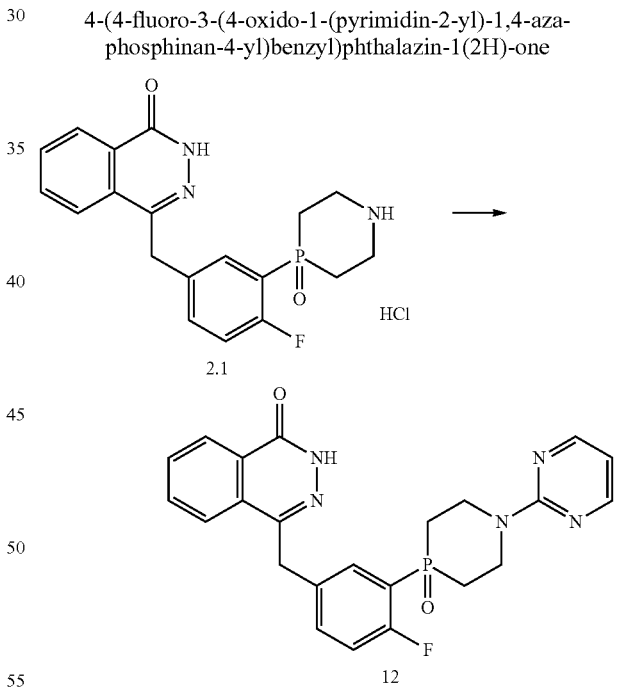

Synthesis of 4-(4-fluoro-3-(4-oxido-1-(pyrimidin-2-yl)-1,4-azaphosphinan-4-yl)benzyl)phthalazin-1(2H)-one (12)

A mixture of 2.1 (50 mg, 0.12 mmol), DIPEA (107 μL, 0.61 mmol), and 2-chloropyrimidine (70 m, 0.61 mmol) in isopropanol (1 mL) was stirred at 100° C. overnight, concentrated and prep-TLC using 10% MeOH/DCM and lyophilized to afford 3a as a white powder (30 mg, 54.4%), $^1$H NMR (CD$_3$OD, 300 MHz) δ 8.38 (m, 3M), 7.96 (d, 1H), 7.85 (m, 3H), 7.63 (m, 1H), 7.16 (m, 1H), 6.69 (t, 1H). 4.73 (m, 3H), 4.43 (s, 2H), 3.91 (m, 2H), 2.37 (m, 2H), 2.05 (t, 2H), LCMS (ESI+) m/z=451.2 (M+H).

Examples 13-37

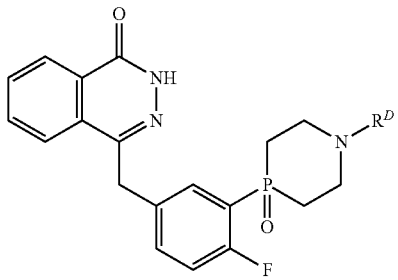

| Example No. | R$^D$ | Chemical Name | $^1$H NMR (300 MHz) (Solvent) δ ppm | LCMS m/z (M + H) |
|---|---|---|---|---|
| 13 | 6-chloropyridazin-3-yl | 4-(3-(1-(6-chloropyridazin-3-yl)-4-oxido-1,4-azaphosphinan-4-yl)-4-fluorobenzyl)phthalazin-1(2H)-one | (CDCl$_3$) 9.96 (s, 1H), 8.45 (d, 1H), 7.96 (m, 1H), 7.78 (m, 3H), 7.46 (m, 1H), 7.33 (d, 1H), 7.00 (m, 2H), 4.66 (m, 2H), 4.33 (s, 2H), 3.98 (m, 2H), 2.40 (m, 2H), 2.12 (m, 2H). | 484 |
| 14 | 5-cyanopyridin-2-yl | 6-(4-(2-fluoro-5-((4-oxo-3,4-dihydrophthalazin-1-yl)methyl)phenyl)-4-oxido-1,4-azaphosphinan-1-yl)nicotinonitrile | (CDCl$_3$) 10.23 (s, 1H), 8.46 (m, 2H), 7.98 (m, 1H), 7.75 (m, 4H), 7.40 (m, 1H), 7.01 (m, 1H), 6.75 (d, 1H), 4.67 (m, 2H), 4.34 (s, 2H), 3.95 (m, 2H), 2.33 (m, 2H), 2.11 (m, 2H). | 474.0 |
| 15 | 4-cyanophenyl | 4-(4-(2-fluoro-5-((4-oxo-3,4-dihydrophthalazin-1-yl)methyl)phenyl)-4-oxido-1,4-azaphosphinan-1-yl)benzonitrile | (DMSO-d$_6$) 8.38 (d, 1H), 8.08 (d, 1H), 7.90 (m, 7H), 7.65 (m, 1H), 7.25 (m, 1H), 4.47 (s, 2H), 4.05 (m, 2H), 3.26 (m, 2H), 2.36 (m, 2H), 1.76 (m, 2H). | 473.0 |
| 16 | 3-cyanopyridin-2-yl | 2-(4-(2-fluoro-5-((4-oxo-3,4-dihydrophthalazin-1-yl)methyl)phenyl)-4-oxido-1,4-azaphosphinan-1-yl)nicotinonitrile | (DMSO-d$_6$) 12.57 (s, 1H), 8.43 (m, 1H), 8.23 (d, 3H). 8.30 (dd, 1H), 7.99 (d, 1H), 7.82 (m, 3H), 7.59 (m, 1H), 7.25 (m, 1H), 6.96 (t, 1H), 4.38 (s, 2H), 4.21 (m, 2H), 3.85 (m, 2H), 2.34 (m, 2H), 2.16 (m, 2H). | 474.0 |
| 17 | 2-chloropyrimidin-4-yl | 4-(3-(1-(2-chloropyrimidin-4-yl)-4-oxido-1,4-azaphosphinan-4-yl)-4-fluorobenzyl)phthalazin-1(2H)-one | | 484.0 |
| 18 | 4-chloropyrimidin-2-yl | 4-(3-(1-(4-chloropyrimidin-2-yl)-4-oxido-1,4-azaphosphinan-4-yl)-4-fluorobenzyl)phthalazin-1(2H)-one | | 484.0 |

-continued

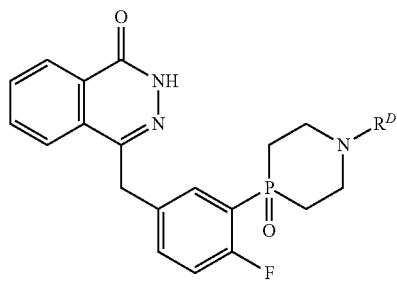

| Example No. | R$^D$ | Chemical Name | $^1$H NMR (300 MHz) (Solvent) δ ppm | LCMS m/z (M + H) |
|---|---|---|---|---|
| 19 | pyridin-2-yl | 4-(4-fluoro-3-(4-oxido-1-(pyridin-2-yl)-1,4-azaphosphinan-4-yl)benzyl)phthalazin-1(2H)-one | | 449.0 |
| 20 | 4-(trifluoromethyl)-6-chloropyridin-2-yl | 4-(3-(1-(3-chloro-5-(trifluoromethyl)pyridin-2-yl)-4-oxido-1,4-azapbosphinan-4-yl)-4-fluorobenzyl)phthalazin-1(2H)-one | | 551.9 |
| 21 | quinazolin-4-yl | 4-(4-fluoro-3-(4-oxido-1-(quinazolin-4-yl)-1,4-azaphosphinan-4-yl)benzyl)phthalazin-1(2H)-one | | 500.0 |
| 22 | 6-chloropyrimidin-4-yl | 4-(3-(1-(6-chloropyrimidin-4-yl)-4-oxido-1,4-azaphosphinan-4-yl)-4-fluorobenzyl)phthalazin-1(2H)-one | | 484.0 |
| 23 | 3-fluoropyridin-2-yl | 4-(4-fluoro-3-(1-(3-fluoropyridin-2-yl)-4-oxido-1,4-azaphosphinan-4-yl)benzyl)phthalazin-1(2H)-one | | 467.0 |
| 24 | 5-(trifluoromethyl)pyridin-2-yl | 4-(4-fluoro-3-(4-oxido-1-(5-(trifluoromethyl)pyridin-2-yl)-1,4-azaphosphinan-4-yl)benzyl)phthalazin-1(2H)-one | | 517.0 |
| 25 | 6-fluoropyridin-2-yl | 4-(4-fluoro-3-(1-(6-fluoropyridin-2-yl)-4-oxido-1,4-azaphosphinan-4-yl)benzyl)phthalazin-1(2H)-one | | 467.0 |

-continued

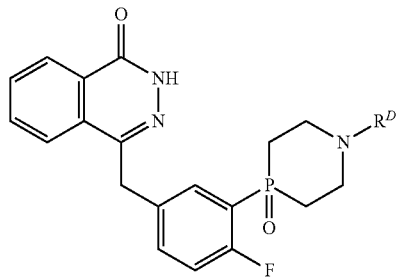

| Example No. | $R^D$ | Chemical Name | $^1$H NMR (300 MHz) (Solvent) δ ppm | LCMS m/z (M + H) |
|---|---|---|---|---|
| 26 | 4-CF₃-pyridin-2-yl | 4-(4-fluoro-3-(4-oxido-1-(4-(trifluoromethyl)pyridin-2-yl)-1,4-azaphosphinan-4-yl)benzyl)phthalazin-1(2H)-one | | 517.0 |
| 27 | 3-CF₃-pyridin-2-yl | 4-(4-fluoro-3-(4-oxido-1-(3-(trifluoromethyl)pyridin-2-yl)-1,4-azaphosphinan-4-yl)benzyl)phthalazin-1(2H)-one | | 517.0 |
| 28 | 3,5-difluoropyridin-2-yl | 4-(4-fluoro-3-(1-(3,5-difluoropyridin-2-yl)-4-oxido-1,4-azaphosphinan-4-yl)benzyl)phthalazin-1(2H)-one | | 485 |
| 29 | 5-fluoropyridin-2-yl | 4-(4-fluoro-3-(1-(5-fluoropyridin-2-yl)-4-oxido-1,4-azaphosphinan-4-yl)benzyl)phthalazin-1(2H)-one | | 467.0 |
| 30 | quinazolin-2-yl | 4-(4-fluoro-3-(4-oxido-1-(quinazolin-2-yl)-1,4-azaphosphinan-4-yl)benzyl)phthalazin-1(2H)-one | | 500.0 |
| 31 | 6-CF₃-pyridin-2-yl | 4-(4-fluoro-3-(4-oxido-1-(6-(trifluoromethyl)pyridin-2-yl)-1,4-azaphosphinan-4-yl)benzyl)phthalazin-1(2H)-one | | 517.0 |
| 32 | thiazol-2-yl | 4-(4-fluoro-3-(4-oxido-1-(thiazol-2-yl)-1,4-azaphosphinan-4-yl)benzyl)phthalazin-1(2H)-one | | 455.0 |

-continued

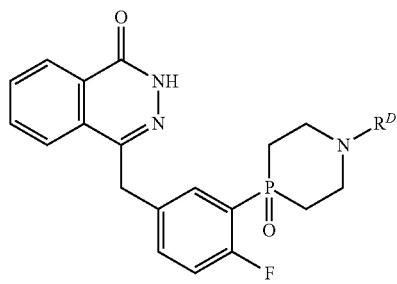

| Example No. | R<sup>D</sup> | Chemical Name | ¹H NMR (300 MHz) (Solvent) δ ppm | LCMS m/z (M + H) |
|---|---|---|---|---|
| 33 | thiadiazol-2-yl | 4-(4-fluoro-3-(4-oxido-1-(thiadiazol-2-yl)-1,4-azaphosphinan-4-yl)benzyl)phthalazin-1(2H)-one | | 456.0 |
| 34 | 3-acetylpyridin-2-yl | 4-(4-fluoro-3-(4-oxido-1-(3-(acetyl)pyridin-2-yl)-1,4-azaphosphinan-4-yl)benzyl)phthalazin-1(2H)-one | | 491.2 |
| 35 | 3-(1-hydroxyethyl)pyridin-2-yl | (±)-4-(4-fluoro-3-(4-oxido-1-(3-(1-hydoxyethyl)pyridin-2-yl)-1,4-azaphosphinan-4-yl)benzyl)phthalazin-1(2H)-one | | 493.1 |
| 35 | 5-fluoropyrimidin-2-yl | 4-(4-fluoro-3-(4-oxido-1-(5-(fluoro)pyrimidin-2-yl)-1,4-azaphosphinan-4-yl)benzyl)phthalazin-1(2H)-one | | 468.1 |
| 36 | 5-chloropyrimidin-2-yl | 4-(4-fluoro-3-(4-oxido-1-(5-(chloro)pyrimidin-2-yl)-1,4-azaphosphinan-4-yl)benzyl)phthalazin-1(2H)-one | | 484.1 |
| 37 | 5-n-propylpyrimidin-2-yl | 4-(4-fluoro-3-(4-oxido-1-(5-(n-propyl)pyrimidin-2-yl)-1,4-azaphosphinan-4-yl)benzyl)phthalazin-1(2H)-one | | 492.2 |

Compounds of Examples 13-37 were prepared using the appropriate starting materials and reagents following the same procedure as in Example 12.

Example 38

4-(3-(1-cyclopropyl-4-oxido-1,4-azaphosphinan-4-yl)-4-fluorobenzyl)phthalazin-1(2H)-one

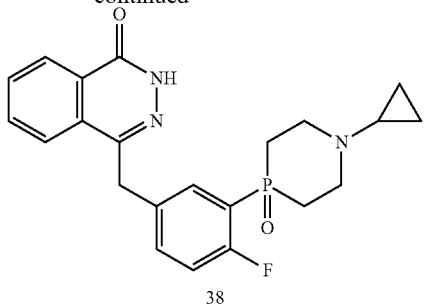

38

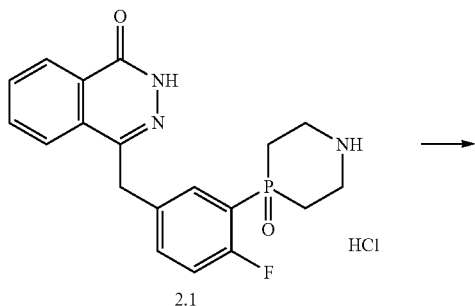

2.1

→

Synthesis of 4-(3-(1-cyclopropyl-4-oxido-1,4-azaphosphinan-4-yl)-4-fluorobenzyl)phthalazin-1(2H)-one (38)

Acetic acid (56 μL, 0.98 mmol) was added to a solution of compound 2.1 (100 mg, 0.25 mmol) and [(1-ethoxy-1-cyclopropyl)oxy]trimethylsilane (74 μL, 0.37 mmol) in MeOH (6 mL) and stirred at r.t, for 5 min. NaBH$_3$CN (25 mg, 0.40 mmol) was added and the mixture stirred at 60° C. for 4 h. concentrated, diluted in EtOAc (30 mL), washed with sat. NaHCO$_3$ (10 mL), brine (10 mL), dried over MgSO$_4$, concentrated and prep-TLC using 10% MeOH/DCM and lyophilized to afford 38 as a white powder (60 mg, 59.5%). $^1$H NMR (CDCl$_3$, 300 MHz) δ 10.24 (s, 1H), 8.45 (d, 1H), 7.96 (m, 1H), 7.76 (m, 3H), 7.43 (m, 1H), 7.05 (m, 1H), 4.33 (s, 2H), 3.17 (m, 3H), 2.28 (m, 2H), 1.93 (m, 6H), 0.55 (d, 2H), LCMS (ESI+) m/z=412.2 (M+H).

Examples 39-48

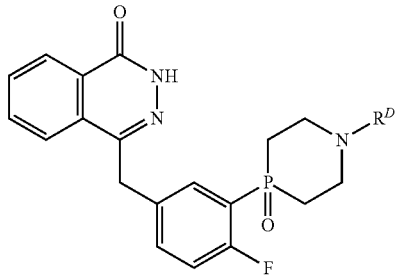

| Example No. | R$^D$ | Chemical Name | $^1$H NMR (300 MHz) (Solvent) δ ppm | LCMS m/z (M + H) |
|---|---|---|---|---|
| 39 | cyclobutyl | 4-(3-(1-cyclobutyl-4-oxido-1,4-azaphosphinan-4-yl)-4-fluorobenzyl)phthalazin-1(2H)-one | (CDCl$_3$) 9.85 (s, 1H), 8.45 (d, 1H), 7.93 (m, 1H), 7.77 (m, 3H), 7.43 (m, 1H), 7.07 (m, 1H), 4.33 (s, 2H), 3.01 (m, 3H), 2.72 (m, 2H), 2.34 (m, 2H), 1.96 (m, 6H), 1.72 (m, 2H). | 426.2 |
| 40 | Me | 4-(4-fluoro-3-(1-methyl-4-oxido-1,4-azaphosphinan-4-yl)benzyl)phthalazin-1(2H)-one | | 386.0 |
| 41 | Et | 4-(3-(1-ethyl-4-oxido-1,4-azaphosphinan-4-yl)-4- | | 400.1 |

-continued

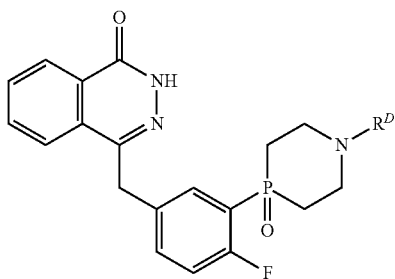

| Example No. | $R^D$ | Chemical Name | $^1$H NMR (300 MHz) (Solvent) δ ppm | LCMS m/z (M + H) |
|---|---|---|---|---|
| | | fluorobenzyl)phthalazin-1(2H)-one | | |
| 42 | CHMe$_2$ | 4-(4-fluoro-3-(1-isopropyl-4-oxido-1,4-azaphosphinan-4-yl)benzyl)phthalazin-1(2H)-one | | 414.2 |
| 43 | ✳-CH$_2$-cyclopropyl | 4-(3-(1-(cyclopropylmethyl)-4-oxido-1,4-azaphosphinan-4-yl)-4-fluorobenzyl)phthalazin-1(2H)-one | | 426.2 |
| 44 | CH$_2$CHMe$_2$ | 4-(4-fluoro-3-(1-isobutyl-4-oxido-1,4-azaphosphinan-4-yl)benzyl)phthalazin-1(2H)-one | | 427.2 |
| 45 | n-Pr | 4-(4-fluoro-3-(4-oxido-4-propyl-1,4-azaphosphinan-4-yl)benzyl)phthalazin-1(2H)-one | | 414.2 |
| 46 | CH$_2$Bu$^t$ | 4-(4-fluoro-3-(1-neopentyl-4-oxido-1,4-azaphosphinan-4-yl)benzyl)phthalazin-1(2H)-one | | |
| 47 | CH$_2$CHEt$_2$ | 4-(4-fluoro-3-(1-neopentyl-4-oxido-1,4-azaphosphinan-4-yl)benzyl)phthalazin-1(2H)-one | | |
| 48 | (CH$_2$)$_2$CHMe$_2$ | 4-(4-fluoro-3-(1-isopentyl)-4-oxido-1,4-azaphosphinan-4-yl)benzyl)phthalazin-1(2H)-one | | |

Compounds of Examples 39-48 were prepared using the appropriate starting materials and reagents following the same procedures as in Example 38.

Example 49

4-(3-(1-cyclopropyl-4-oxido-1,4-azaphosphinan-4-yl)-4-fluorobenzyl)phthalazin-1(2H)-one

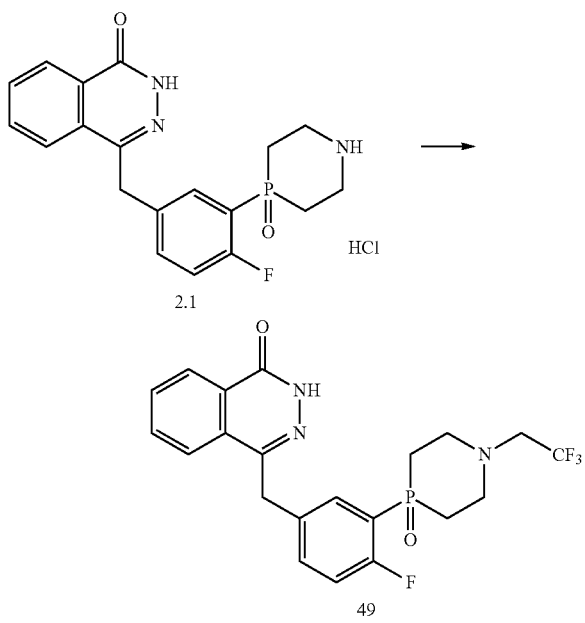

Synthesis of 4-(4-fluoro-3-(4-oxido-1-(2,2,2-trifluoroethyl)-1,4-azaphosphinan-4-yl)benzyl)phthalazin-1(2H)-one (49)

2,2,2-trifluoroethanol (360 μL. 5.00 mmol) was added to a solution of trifluoromethanesulfonic anhydride (839 μL, 5.00 mmol) in toluene (3 mL) at 0° C. and stirred for 1 h at rt. 1.2 (50 mg, 0.12 mmol) and DIPEA (107 μL, 0.61 mmol) were added and the mixture was stirred at 100° C. overnight, concentrated and prep-TLC using 10% MeOH/DCM and lyophilized to afford 49 as a light brown powder. $^1$H NMR (CD$_3$OD, 300 MHz) δ 8.35 (d, 1H), 7.94 (d, 1H), 7.84 (m, 3H), 7.66 (m, 1H), 7.22 (m, 1H), 4.43 (s, 2H), 3.24 (s, 2H), 2.42 (m, 4H), 2.01 (m, 4H). MS (ESI+) m/z=454.2 (M+H).

Example 50

4-[[4-fluoro-3-(4-methyl-4-oxo-1,4-azaphosphinane-1-carbonyl)phenyl]methyl]-2H-phthalazin-1-one

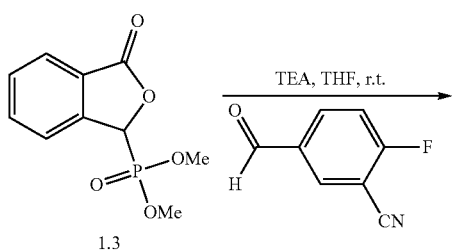

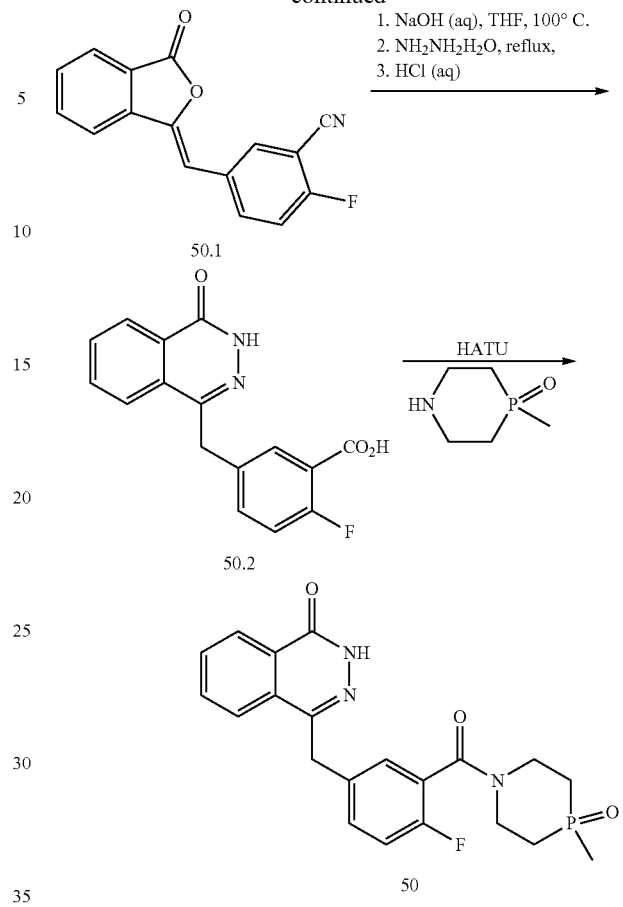

Step 50.1: Synthesis of 3-(3-cyano-4-fluorobenzylidene)isobenzofuran-1(3H)-one (50.1)

To a mixture of 1.3 (2.42 g, 10.0 mmol) and 2-fluoro-5-formylbenzonitrile (1.49 g, 10 mmol) in THF (20 mL) was added triethylamine (1.11 g, 1 mmol) dropwise over 5 min, and the temperature was maintained below 15° C. The reaction mixture was slowly warmed to 20° C. over 1 h and was then concentrated in vacuo. The residue was triturated with water (20 mL). The solid was collected by filtration, washed with water (5 mL), ether (10 mL), and hexane (10 mL), and was dried to produce compound 50.1 as a mixture of E and Z isomers. The material was used without further purification.

Step 50.2: Synthesis of 2-Fluoro-5-[(4-oxo-3H-phthalazin-1-yl)methyl]benzoic Acid (5.2)

As such, to a stirred suspension of 50.1 (~10 mmol) in water (20 mL) was added aqueous NaOH (10 N, 5 mL). The reaction was subsequently heated to 100° C. for 1 h. After the reaction mixture was cooled to roughly 70° C. and hydrazine hydrate (5.0 mL, 100 mmol) was added. The mixture was stirred at 70° C. for 24 h. The reaction was cooled room temperature and acidified with HCl (8 N, ca. 80 mL) to pH 4. After reaction was again cooled to room temperature, the solid was collected with filtration, washed with water (10 mL), ether (3×10 mL) and was dried to produce compound 50.2 (2.41 g) as a white solid. MS (ESI+) m/z=299 (M+H).

Step 50.3: Synthesis of 4-[[4-fluoro-3-(4-methyl-4-oxo-1,4-azaphosphinane-1-carbonyl)phenyl]methyl]-2H-phthalazin-1-one (50)

HATU (85 mg, 0.22 mmol) was added to a solution of compound 40.2 (59 mg, 0.20 mmol) and DIPEA (144 µL, 0.83 mmol) in DMF (3 mL). After 5 min, 4-methyl-1,4-azaphosphinane 4-oxide (preparation seen WO2011/002523A1) 39 mg, 0.30 mmol) was added and stirred at r.t. overnight, concentrated, diluted in EtOAc (30 mL), washed with H$_2$O (2×30 mL), brine (30 mL), dried over MgSO$_4$, concentrated and prep-TLC using 15% MeOH/DCM, followed by lyophilization gave 50 as an off white powder. MS (ESI+) m/z=414 (M+H).

Examples 51-53

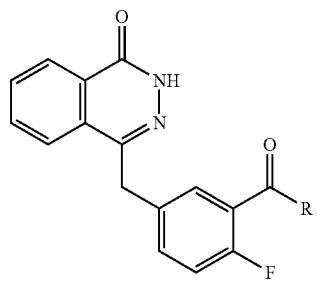

| Example No. | "R" group | Chemical Name | LCMS m/z (M + H) |
|---|---|---|---|
| 51 | | 4-[[4-fluoro-3-(4-ethyl-4-oxo-1,4-azaphosphinane-1-carbonyl)phenyl]methyl]-2H-phthalazin-1-one | 429 |
| 52 | | 4-[[4-fluoro-3-(4-isopropyl-4-oxo-1,4-azaphosphinane-1-carbonyl)phenyl]methyl]-2H-phthalazin-1-one | 443 |
| 53 | | 4-[[4-fluoro-3-(4-ethoxyl-4-oxo-1,4-azaphosphinane-1-carbonyl)phenyl]methyl]-2H-phthalazin-1-one | 445 |

Compounds of Examples 51-53 were prepared using the appropriate starting materials and reagents according to the same procedures as in Example 50. The 1,4-azaphosphinane 4-oxide derivatives were made by using the same procedures as described in WO2011/002523A1.

Example 54

4-(3-(1-cyclopropyl-4-oxido-1,4-azaphosphinan-4-yl)-4-fluorobenzyl)-7-fluorophthalazin-1(2H)-one

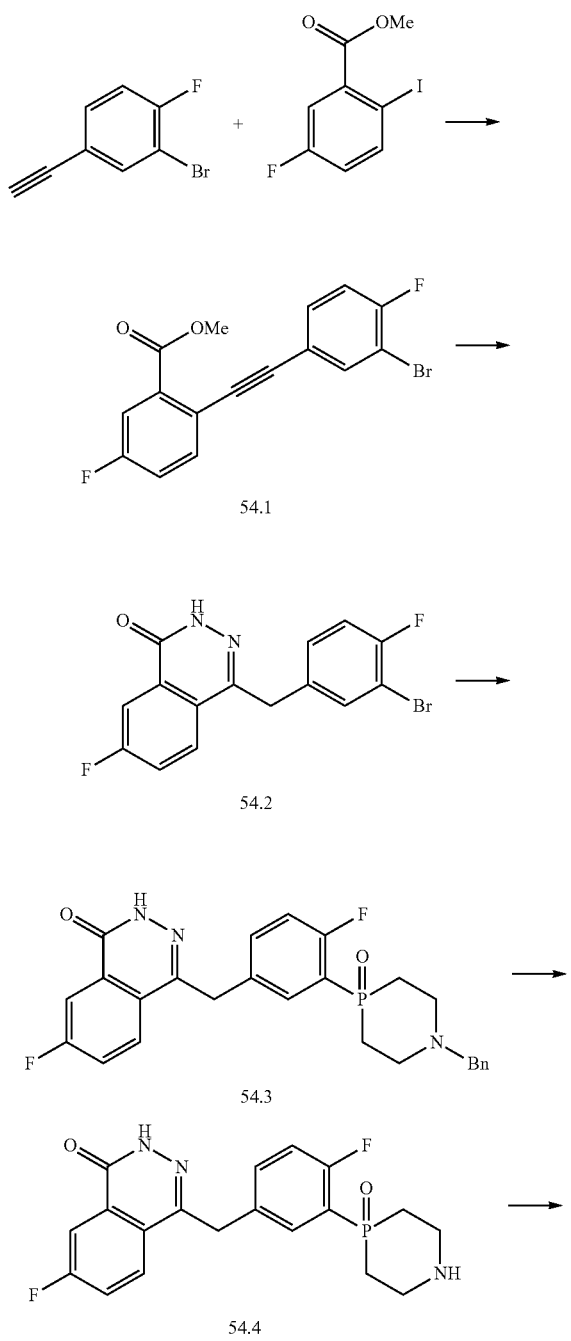

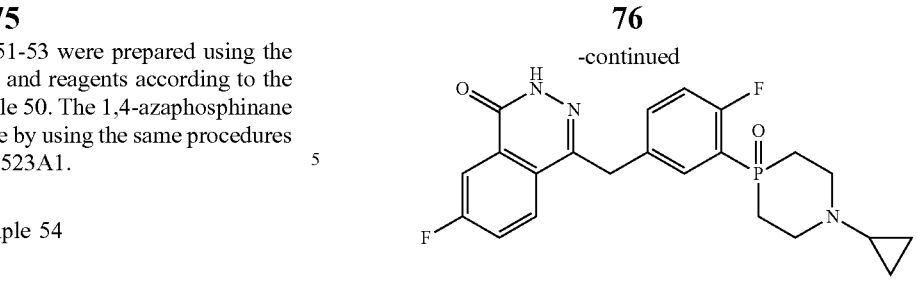

54

Step 1, methyl 2-(2-(3-bromo-4-fluorophenyl)ethynyl)-5-fluorobenzoate (54.1): To a flask with 2-bromo-4-ethynyl-1-fluorobenzene (1.3 g. 6.5 mmole) and methyl 5-fluoro-2-iodobenzoate (2 g, 7.1 mmole) in DMF (10 mL) was added triethyl amine (2 mL), CuI (200 mg), Pd(dppf)Cl2 (100 mg) under nitrogen, the mixture was heated to 80° C. overnight. After cooling down, the solvent was removed and the residue was purified through chromatography to provide the desired product (1.67 g).

Step 2, 4-(3-bromo-4-fluorobenzyl)-7-fluorophthalazin-1 (2H)-one (54.2): A mixture of methyl 2-(2-(3-bromo-4-fluorophenyl)ethynyl)-5-fluorobenzoate (54.1, 1.5 g, 4.3 mmole) and 9 mmole of 80% NH2NH2.H2O were refluxed in 10 mL of ethanol for 8 h until full disappearance of the ester. The reaction mixture was cooled and the precipitate was filtered. A mixture of the hydrazide and 1.2 equiv. of KOH was refluxed in 10 ml of EtOH until full disappearance of the hydrazide. The desired product was purified through chromatography to give the desired product (860 mg).

Step 3, compound (54.3): Palladium (II) acetate (386 mg, 1.72 mmol) and 1,3-bis(diphenylphosphino)-propane (710 mg, 1.72 mmol) were stirred in DMF (30 mL) for 15 min. A solution of phosphine oxide (3.82 g, 11.47 mmol), 54.2 (2.40 g, 11.47 mmol), and DIPEA (10 mL, 57.36 mmol) in DMF (10 mL) was added and the reaction mixture stirred at 120° C. overnight. After concentrating, column chromatography using 0-10% (gradient) MeOH/DCM gave a light yellow semisolid, which was diluted in DCM (100 mL), washed with $H_2O$ (2×100 mL), the aqueous layer was extracted with DCM (100 mL), combined organic layer was then washed with brine (100 mL), dried over $MgSO_4$, concentrated, sonicated in ether and filtered to afford 54.3 as a pale yellow solid (3.27 g, 61.8%).

Step 4 Compound (54.4): A mixture of 54.3 (1.00 g, 2.17 mmol), 4M HCl in 1,4-dioxane (2 mL), and Pd(OH)$_2$/C (20% wt. wet, 1 g) in MeOH (30 mL) was hydrogenated under 60 psi $H_{2(g)}$ overnight. The reaction mixture was filtered through celite, cake washed with warm MeOH (100 mL), combined filtrates concentrated and lyophilized to give 54.4 as a pale yellow hydrochloride salt (800 mg, 90.5%).

Step 5, synthesis of 4-(3-(1-cyclopropyl-4-oxido-4-azaphosphinan-4-yl)-4-fluorobenzyl)-7-Fluorophthalazin-1 (2H)-one (54): Acetic acid (56 μL, 0.98 mmol) was added to a solution of 54.4 (100 mg, 0.25 mmol) and [(1-ethoxy-1-cyclopropyl)oxy]trimethylsilane (74 μL, 0.37 mmol) in MeOH (6 mL) and stirred at rt for 5 min. NaBH$_3$CN (25 mg, 0.40 mmol) was added and the mixture stirred at 60° C. for 4 h, concentrated, diluted in EtOAc (30 mL), washed with sat. NaHCO$_3$ (10 mL), brine (10 mL), dried over MgSO$_4$, concentrated and prep-TLC using 10% MeOH/DCM and lyophilized to afford 54 as a white powder (60 mg, 59.5%). $^1$H NMR (CDCl$_3$, 300 MHz) δ 8.31 (d, 1H), 7.86 (m, 3H), 7.66 (m, 1H), 7.28 (m, 1H), 3.14 (m, 4H), 2.39 (m, 2H), 2.10 (m, 2H), 1.89 (m, 1H), 0.47 (m, 4H). LCMS (ESI+) m/z=430.0 (M+H).

Example 55

4-[(3-(1-cyclopropyl-4-oxido-1,4-azaphosphinan-4-yl)-4-fluorophenyl)dideuteromethyl]-7-fluorophthalazin-1 (2H)-one

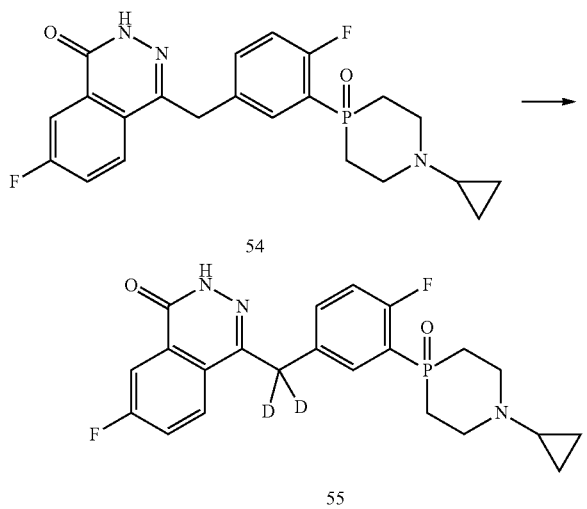

To a solution of compound 54 (20 mg) in $D_2O$: D-DMSO (2 mL, 1:1) was added DBU (1 mL) and the mixture was heated to 50° C. for 2 h. The reaction mixture was cooled down to room temperature and water was added. The desired product was extracted with methylene chloride and dried to give the desired product 52 (18 mg). LCMS (ESI+) m/z=432.0 (M+H).

Example 56

4-(4-fluoro-3-(4-oxido-1-(pyrimidin-2-yl)-1,4-azaphosphinan-4-yl)benzyl)-7-fluorophthalazin-1(2H)-one

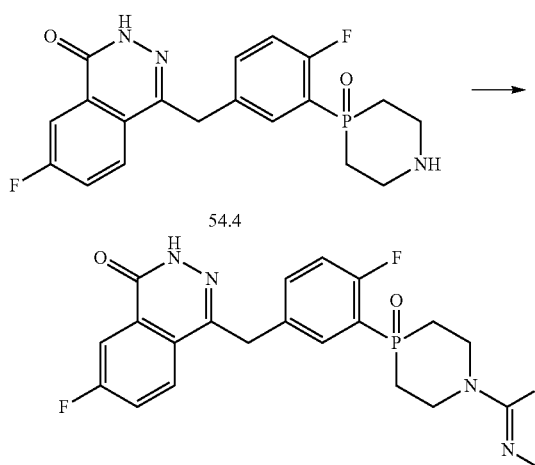

A mixture of 54.4 (50 mg, 0.12 mmol), DIPEA (107 μL, 0.61 mmol), and 2-chloropyrimidine (70 mg, 0.61 mmol) in isopropanol (1 mL) was stirred at 100° C. overnight, concentrated and prep-TLC using 10% MeOH/DCM and lyophilized to afford 56 as a white powder (30 mg, 54.4%), $^1$H NMR (CD$_3$OD, 300 MHz) δ 8.38 (m, 3H), 7.96 (d, 1H). 7.85 (m, 3H), 7.63 (m, 1H). 7.16 (m, 1H), 6.69 (t, 1H), 4.73 (m, 3H). 4.43 (s, 2H). 3.91 (m, 2H), 2.37 (nm, 2H), 2.05 (t, 2H), LCMS (ESI+) m/z=451.2 (M+H).

Example 57

4-[(4-fluoro-3-(4-oxido-1-(pyrimidin-2-yl)-1,4-azaphosphinan-4-yl)phenyl)dideuteromethyl]-7-fluorophthalazin-1(2H)-one

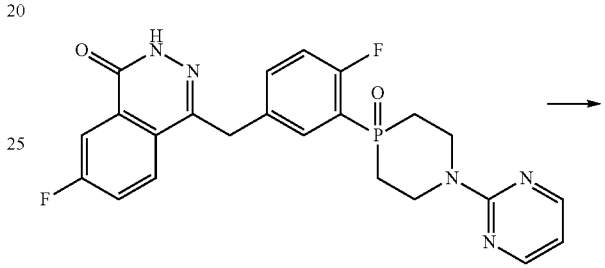

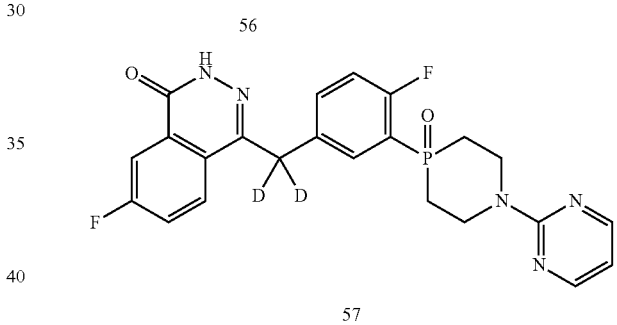

The general procedure described in example 55 is followed and the desired produce 57 is obtained.

Example 58

(±)-4-[(3-(1-cyclopropyl-4-oxido-1,4-azaphosphinan-4-yl)-4-fluoro-1-phenyl)(hydroxymethyl)]phthalazin-1(2H)-one

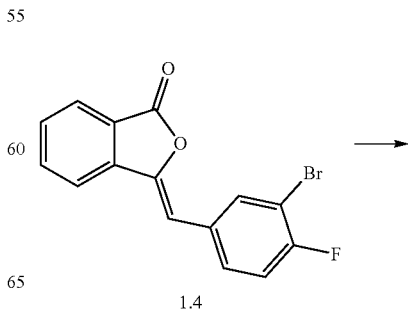

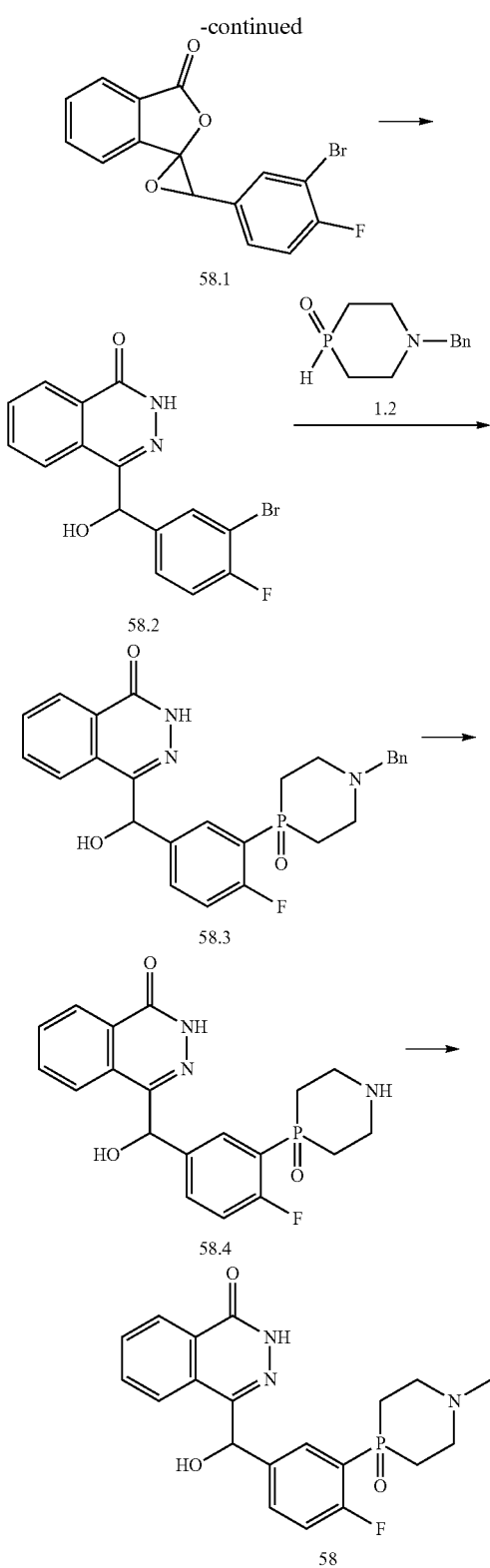

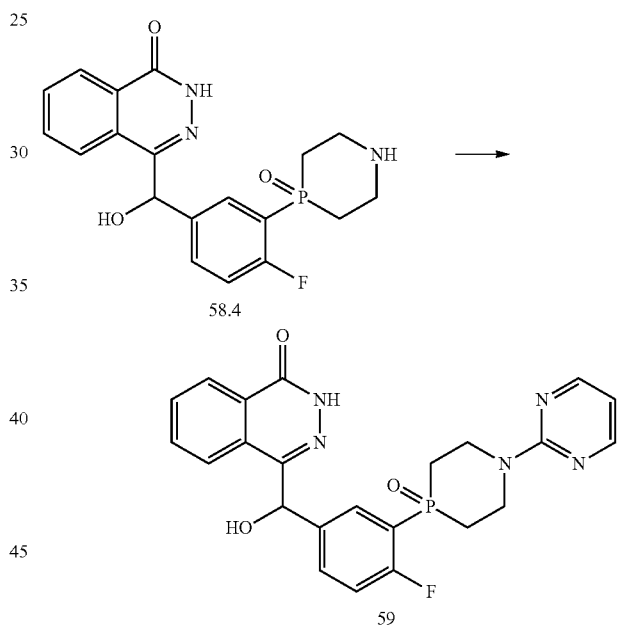

water and brine, dried over anhydrous magnesium sulfate, filtered and concentrated to give the crude product of 58.1, which was used without further purification Step 2, 3 and 4, synthesis of (±)-4-[(3-(4-oxido-1,4-azaphosphinan-4-yl)-4-fluoro-1-phenyl)(hydroxymethyl)]-phthalazin-1(2H)-one (58.4). The title compound was synthesized with the same procedures as the synthesis of compound 2.1 from compound 1.4, by using compound 58.1 instead of compound 1.4. MS (ESI) m/z=388 (M+H⁺).

Step 5, synthesis of (±)-4-[(3-(1-cyclopropyl-4-oxido-1,4-azaphosphinan-4-yl)-4-fluoro-1-phenyl)(hydroxymethyl)]-phthalazin-1 (2H)-one (58). The title compound was synthesized with the same procedures as the synthesis of example 38, by using compound 58.4 instead of compound 2.1. LCMS (ESI) m/z=428 (M+$^H$).

Example 59

(+)-4-[[4-fluoro-3-(4-oxido-1-(pyrimidin-2-yl)-1,4-azaphosphinan-4-yl)phenyl)](hydroxymethyl)]-7-fluorophthalazin-1(2H)-one The title compound was synthesized with the same procedures as the synthesis of example 12, by using compound 58.4 instead of compound 2.1. MS (ESI) r/z=466 (M+H⁺).

Example 60

PARP-1 Enzyme Assay

Inhibition of PARP-1 enzymatic activities was measured using an HT Universal Colorimetric PARP Assay Kit (Trevigen, catalogue #4677-096-K) following the standard procedures.

Serial dilutions of PARP compounds were added to appropriate wells. The compound was incubated with PARP enzyme at RT for 10 min, and the reaction was initiated by addition of the PARP substrate cocktail, Each concentration of compound was tested in triplicate wells. After 15 min reaction, the reaction was stopped, and the Strep-HRP was Step 1, synthesis of compound 58.1. To a solution of compound 1.4 (1.69 g, 5.0 mmol) in DCM (20 mL) was added mCPBA (2.88 g, ~60% pure, ~10 mmol). Reaction was stirred at room temperature for 12 hour. The reaction was then diluted with EtOAc (80 mL), and the mixture was washed with 20 mL each of 1 M aqueous sodium carbonate, added into each well and incubated for 1 h at RT. After addition of TACS-Sapphire™ colorimetric substrate and incubated in dark for 15 min, the OD450 was read out with an EnVision instrument. $IC_{50}$ values (the concentration at which 50% of the enzyme activity is inhibited) were calculated, which are determined over a range of different concentrations, normally from 10 μM to 0.1 nM.

Selected compounds of the present invention were tested and the activities ($IC_{50}$) are summarized in Table 2.

Example 61

PARP Cell Assay

Inhibition of intracellular PARP enzyme was determined using an immunohistochemistry (IHC) assay. The cellular assay measures the formation of poly (ADP)-ribose catalyzed by PARP inside cells. Activity indicates that the compound can permeate into the intact cells to inhibit PARP enzymes.

Materials:
Anti-PAR (Ab-1) Mouse mAb (10H) (Calbiochem, AM-80); Anti-Mouse IgG (whole molecule)-FITC antibody produced in goat (sigma, F2012); DAPI (sigma, D9542).

Assay Procedures:
The C41 cells (Human cervical carcinoma; ATCC No. CRL-1594) were planted into 96-well plates at 8.0E4 cells/well and incubated at 37° C. overnight. Cells were washed with 37° C. warmed PBS once and treated with test compounds for 2 h in 96-well plates. Cells were washed with 37° C. warmed PBS once, and PARP was activated by damaging DNA with 1.0 mM $H_2O_2$ for 10 min. Cells were washed with ice-cold PBS once and fixed with pre-chilled methanol/acetone (7:3) at −20° C. for 10 min. After air-drying, plates were rehydrated with PBS and blocked using 5% nonfat dry milk in PBS-Tween (0.05%) (block solution) for 30 min at room temperature. Cells were incubated with anti-PAR antibody 10H (1:100) in blocking solution at room temperature for 60 min, followed by washing with PBS-Tween20.5 times and incubation with goat anti-mouse FITC-coupled antibody (1:50) and 1 μg/mL DAPI in blocking solution at room temperature for 60 min. After washing with PBS-Tween20.5 times, analysis was performed using Vector 3 Microplate Reader (PerkinElmer) set at the excitation (485 nm) and emission (535 nm) wavelength for FITC or the excitation (364 nm) and emission (454 nm) wavelength for DAPI. PARP activity (FITC signal) was normalized with cell numbers (DAPI). The $EC_{50}$ values (the concentration at which 50% of the PARP activity is inhibited) were calculated based on the PARP activities determined over a range of different concentrations.

Selected compounds of the present invention were tested and the activities ($EC_{50}$) are summarized in Table 2.

TABLE 2

PARP Inhibition Data

| Example No. | $IC_{50}$ (PARP-1 inhibition)[a] | $EC_{50}$ (TARP cell assay)[a] |
|---|---|---|
| 1 | +++ | ND |
| 2 | + | ND |
| 3 | +++ | ND |
| 4 | +++ | ND |
| 5 | +++ | ND |
| 6 | +++ | ND |
| 7 | ++ | ND |
| 8 | +++ | ND |
| 9 | ++ | ND |
| 10 | ++ | ND |
| 11 | +++ | ND |
| 12 | +++ | +++ |
| 13 | +++ | ++ |
| 14 | +++ | +++ |
| 15 | + | ND |
| 16 | +++ | ND |
| 17 | +++ | ND |
| 18 | +++ | ++ |
| 19 | +++ | ++ |
| 20 | ++ | ND |
| 21 | +++ | ++ |
| 22 | +++ | +++ |
| 23 | +++ | +++ |
| 24 | +++ | ND |
| 25 | +++ | +++ |
| 26 | +++ | ND |
| 27 | ++ | ND |
| 28 | +++ | ++ |
| 29 | ND | ND |
| 30 | +++ | ND |
| 31 | ++ | ND |
| 32 | ND | ND |
| 33 | ND | ND |
| 34 | +++ | ND |
| 35 | ++ | ND |
| 35 | +++ | +++ |
| 36 | +++ | ++ |
| 37 | ++ | ND |
| 38 | +++ | +++ |
| 39 | +++ | +++ |
| 40 | ++ | ND |
| 41 | +++ | ++ |
| 42 | +++ | ND |
| 43 | +++ | ++ |
| 44 | +++ | +++ |
| 45 | +++ | +++ |
| 46 | +++ | ND |
| 47 | ++ | ND |
| 48 | +++ | ++ |
| 49 | +++ | ND |
| 50 | +++ | ND |
| 51 | +++ | ND |
| 52 | +++ | ND |
| 53 | +++ | ND |
| 54 | +++ | ND |
| 55 | +++ | ND |
| 56 | +++ | ND |
| 57 | +++ | ND |
| 58 | +++ | ND |
| 59 | +++ | ND |

[a]"+++" indicates $IC_{50}$ or $EC_{50}$ value below 100 nM;
"++" indicates $IC_{50}$ or $EC_{50}$ value between 100 nM and 1000 nM;
"+" indicates $IC_{50}$ or $EC_{50}$ value between 1000 nM and 10,000 nM; and
"ND" means not determined.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:
1. A compound of the formula (I):

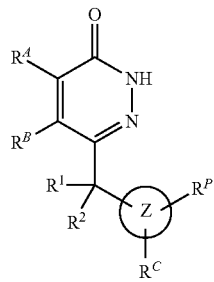
(I)

wherein
$R^A$ and $R^B$ are taken together with the carbon atoms to which they are attached to form a substituted or unsubstituted 6-membered aromatic ring, wherein the substituted 6-membered aromatic ring is substituted by $R^F$, wherein $R^F$ is hydrogen, halo, —CF$_3$, unsubstituted C$_1$-C$_3$ alkyl or unsubstituted C$_1$-C$_3$ alkoxy;
each $R^1$ and $R^2$ is independently hydrogen, halo, hydroxy, unsubstituted C$_1$-C$_3$ alkyl or unsubstituted C$_1$-C$_3$ alkoxy;
Z is a 6-membered aryl substituted with $R^C$ and $R^P$;
$R^C$ is hydrogen, halo, —CF$_3$, unsubstituted C$_1$-C$_3$ alkyl or unsubstituted C$_1$-C$_3$ alkoxy;
$R^P$ is a moiety of the formula (Ia) or (Ib):

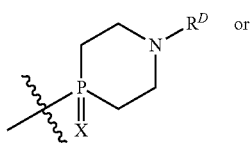
(Ia)

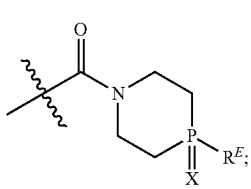
(Ib)

each X is independently O, S or absent;
$R^D$ is hydrogen, substituted or unsubstituted alkyl, unsubstituted cycloalkyl, substituted or unsubstituted aryl, substituted or unsubstituted heteroaryl, —C(O)R$^4$, —C(=N—CN)NR$^8$R$^9$ or —C(O)NR$^5$R$^6$;
$R^4$ is an unsubstituted alkyl, unsubstituted cycloalkyl, unsubstituted alkoxy, or substituted or unsubstituted heterocyclyl;
each $R^5$ and $R^6$ is independently hydrogen, unsubstituted alkyl or unsubstituted cycloalkyl;
each $R^8$ and $R^9$ is independently hydrogen, unsubstituted alkyl or unsubstituted cycloalkyl, or $R^8$ and $R^9$ are taken together with the nitrogen to which they are attached to form an unsubstituted heterocyclyl;
$R^E$ is unsubstituted alkyl, unsubstituted cycloalkyl, unsubstituted aryl, or —OR$^7$; and $R^7$ is an unsubstituted alkyl or unsubstituted cycloalkyl;
wherein the substituted alkyl, the substituted aryl, the substituted heteroaryl, and the substituted heterocyclyl are independently substituted by one, two, three, or more substituents, wherein the substituents are independently cyano, halo, haloalkyl, alkyl, alkylcarbonyl, cycloalkyl, or aryl; wherein said alkyl substituents are optionally substituted with hydroxyl,
or a pharmaceutically acceptable salt or solvate thereof.

2. The compound of claim 1, or a pharmaceutically acceptable salt or solvate thereof, wherein each $R^1$ and $R^2$ is hydrogen.

3. The compound of claim 1, or a pharmaceutically acceptable salt or solvate thereof, wherein $R^F$ is hydrogen.

4. The compound of claim 1, wherein the compound is of the formula (III):

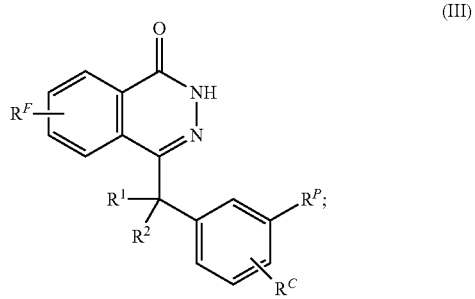
(III)

or a pharmaceutically acceptable salt or solvate thereof.

5. The compound of claim 1, wherein the compound is of the formula (IIIa):

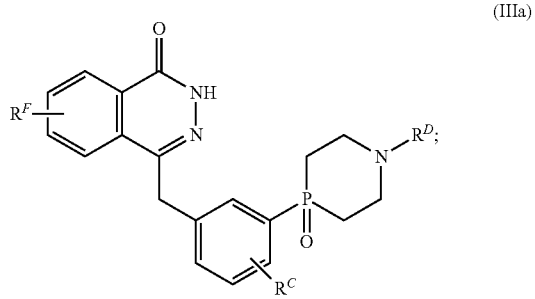
(IIIa)

or a pharmaceutically acceptable salt or solvate thereof.

6. The compound of claim 5, or a pharmaceutically acceptable salt or solvate thereof, wherein $R^D$ is unsubstituted C$_1$-C$_6$ cycloalkyl.

7. The compound of claim 5, or a pharmaceutically acceptable salt or solvate thereof, wherein $R^C$ is halo.

8. The compound of claim 1, wherein the compound is of the formula (IIIb):

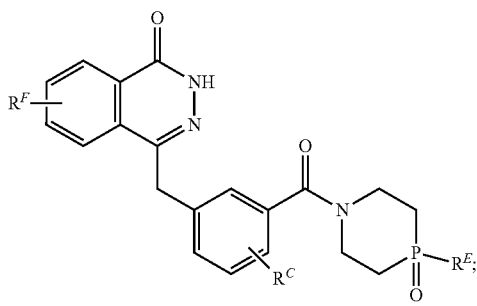

or a pharmaceutically acceptable salt or solvate thereof.

9. A compound selected from the group consisting of:
4-(3-(1-benzyl-4-oxido-1,4-azaphosphinan-4-yl)-4-fluorobenzyl)phthalazin-1(2H)-one;
4-(3-(1-(cyclopentanecarbonyl)-4-oxido-1,4-azaphosphinan-4-yl)-4-fluorobenzyl)phthalazin-1(2H)-one;
4-(3-(1-(cyclopropanecarbonyl)-4-oxido-1,4-azaphosphinan-4-yl)-4-fluorobenzyl)phthalazin-1(2H)-one;
4-(3-(1-(cyclobutanecarbonyl)-4-oxido-1,4-azaphosphinan-4-yl)-4-fluorobenzyl)phthalazin-1(2H)-one;
4-(3-(1-(3,3-dimethylbutanoyl)-4-oxido-1,4-azaphosphinan-4-yl)-4-fluorobenzyl)phthalazin-1(2H)-one;
4-(3-(1-(3,3-difluoropyrrolidine-1-carbonyl)-4-oxido-1,4-azaphosphinan-4-yl)-4-fluorobenzyl)phthalazin-1(2H)-one;
4-(4-fluoro-3-(4-oxido-1-(tetrahydrofuran-2-carbonyl)-1,4-azaphosphinan-4-yl)benzyl)phthalazin-1(2H)-one;
4-(4-fluoro-3-(4-oxido-1-pivaloyl-1,4-azaphosphinan-4-yl)benzyl)phthalazin-1(2H)-one;
4-(2-fluoro-5-((4-oxo-3,4-dihydrophthalazin-1-yl)methyl)phenyl)-N,N-dimethyl-1,4-azaphosphinane-1-carboxamide 4-oxide;
4-(4-fluoro-3-(4-oxido-1-(pyrrolidine-1-carbonyl)-1,4-azaphosphinan-4-yl)benzyl)phthalazin-1(2H)-one;
N-(azetidin-1-yl(4-(2-fluoro-5-((4-oxo-3,4-dihydrophthalazin-1-yl)methyl)phenyl)-4-oxido-1,4-azaphosphinan-1-yl)methylene)cyanamide;
4-(4-fluoro-3-(4-oxido-1-(pyrimidin-2-yl)-1,4-azaphosphinan-4-yl)benzyl)phthalazin-1(2H)-one;
4-(3-(1-(6-chloropyridazin-3-yl)-4-oxido-1,4-azaphosphinan-4-yl)-4-fluorobenzyl)phthalazin-1(2H)-one;
6-(4-(2-fluoro-5-((4-oxo-3,4-dihydrophthalazin-1-yl)methyl)phenyl)-4-oxido-1,4-azaphosphinan-1-yl)nicotinonitrile;
4-(4-(2-fluoro-5-((4-oxo-3,4-dihydrophthalazin-1-yl)methyl)phenyl)-4-oxido-1,4-azaphosphinan-1-yl)benzonitrile;
2-(4-(2-fluoro-5-((4-oxo-3,4-dihydrophthalazin-1-yl)methyl)phenyl)-4-oxido-1,4-azaphosphinan-1-yl)nicotinonitrile;
4-(3-(1-(2-chloropyrimidin-4-yl)-4-oxido-1,4-azaphosphinan-4-yl)-4-fluorobenzyl)phthalazin-1(2H)-one;
4-(3-(1-(4-chloropyrimidin-2-yl)-4-oxido-1,4-azaphosphinan-4-yl)-4-fluorobenzyl)phthalazin-1(2H)-one;
4-(4-fluoro-3-(4-oxido-1-(pyridin-2-yl)-1,4-azaphosphinan-4-yl)benzyl)phthalazin-1(2H)-one;
4-(3-(1-(3-chloro-5-(trifluoromethyl)pyridin-2-yl)-4-oxido-1,4-azaphosphinan-4-yl)-4-fluorobenzyl)phthalazin-1(2H)-one;
4-(4-fluoro-3-(4-oxido-1-(quinazolin-4-yl)-1,4-azaphosphinan-4-yl)benzyl)phthalazin-1(2H)-one;
4-(3-(1-(6-chloropyrimidin-4-yl)-4-oxido-1,4-azaphosphinan-4-yl)-4-fluorobenzyl)phthalazin-1(2H)-one;
4-(4-fluoro-3-(1-(3-fluoropyridin-2-yl)-4-oxido-1,4-azaphosphinan-4-yl)benzyl)phthalazin-1(2H)-one;
4-(4-fluoro-3-(4-oxido-1-(5-(trifluoromethyl)pyridin-2-yl)-1,4-azaphosphinan-4-yl)benzyl)phthalazin-1(2H)-one;
4-(4-fluoro-3-(1-(6-fluoropyridin-2-yl)-4-oxido-1,4-azaphosphinan-4-yl)benzyl)phthalazin-1(2H)-one;
4-(4-fluoro-3-(4-oxido-1-(4-(trifluoromethyl)pyridin-2-yl)-1,4-azaphosphinan-4-yl)benzyl)phthalazin-1(2H)-one;
4-(4-fluoro-3-(4-oxido-1-(3-(trifluoromethyl)pyridin-2-yl)-1,4-azaphosphinan-4-yl)benzyl)phthalazin-1(2H)-one;
4-(4-fluoro-3-(1-(3,5-difluoropyridin-2-yl)-4-oxido-1,4-azaphosphinan-4-yl)benzyl)phthalazin-1(2H)-one;
4-(4-fluoro-3-(1-(5-fluoropyridin-2-yl)-4-oxido-1,4-azaphosphinan-4-yl)benzyl)phthalazin-1(2H)-one;
4-(4-fluoro-3-(4-oxido-1-(quinazolin-2-yl)-1,4-azaphosphinan-4-yl)benzyl)phthalazin-1(2H)-one;
4-(4-fluoro-3-(4-oxido-1-(6-(trifluoromethyl)pyridin-2-yl)-1,4-azaphosphinan-4-yl)benzyl)phthalazin-1(2H)-one;
4-(4-fluoro-3-(4-oxido-1-(thiazol-2-yl)-1,4-azaphosphinan-4-yl)benzyl)phthalazin-1(2H)-one;
4-(4-fluoro-3-(4-oxido-1-(thiadiazol-2-yl)-1,4-azaphosphinan-4-yl)benzyl)phthalazin-1(2H)-one;
4-(4-fluoro-3-(4-oxido-1-(3-(acetyl)pyridin-2-yl)-1,4-azaphosphinan-4-yl)benzyl)phthalazin-1(2H)-one;
(±)-4-(4-fluoro-3-(4-oxido-1-(3-(1-hydroxyethyl)pyridin-2-yl)-1,4-azaphosphinan-4-yl)benzyl)phthalazin-1(2H)-one;
4-(4-fluoro-3-(4-oxido-1-(5-(fluoro)pyrimidin-2-yl)-1,4-azaphosphinan-4-yl)benzyl)phthalazin-1(2H)-one;
4-(4-fluoro-3-(4-oxido-1-(5-(chloro)pyrimidin-2-yl)-1,4-azaphosphinan-4-yl)benzyl)phthalazin-1(2H)-one;
4-(4-fluoro-3-(4-oxido-1-(5-(n-propyl)pyrimidin-2-yl)-1,4-azaphosphinan-4-yl)benzyl)phthalazin-1(2H)-one;
4-(3-(1-cyclopropyl-4-oxido-1,4-azaphosphinan-4-yl)-4-fluorobenzyl)phthalazin-1(2H)-one;
4-(3-(1-cyclobutyl-4-oxido-1,4-azaphosphinan-4-yl)-4-fluorobenzyl)phthalazin-1(2H)-one;
4-(4-fluoro-3-(1-methyl-4-oxido-1,4-azaphosphinan-4-yl)benzyl)phthalazin-1(2H)-one;
4-(3-(1-ethyl-4-oxido-1,4-azaphosphinan-4-yl)-4-fluorobenzyl)phthalazin-1(2H)-one;
4-(4-fluoro-3-(1-isopropyl-4-oxido-1,4-azaphosphinan-4-yl)benzyl)phthalazin-1(2H)-one;
4-(3-(1-(cyclopropylmethyl)-4-oxido-1,4-azaphosphinan-4-yl)-4-fluorobenzyl)phthalazin-1(2H)-one;
4-(4-fluoro-3-(1-isobutyl-4-oxido-1,4-azaphosphinan-4-yl)benzyl)phthalazin-1(2H)-one;
4-(4-fluoro-3-(4-oxido-1-propyl-1,4-azaphosphinan-4-yl)benzyl)phthalazin-1(2H)-one;
4-(4-fluoro-3-(1-neopentyl-4-oxido-1,4-azaphosphinan-4-yl)benzyl)phthalazin-1(2H)-one;
4-(3-(1-(2-ethylbutyl)-4-oxido-1,4-azaphosphinan-4-yl)-4-fluorobenzyl)phthalazin-1(2H)-one;
4-(4-fluoro-3-(1-isopentyl-4-oxido-1,4-azaphosphinan-4-yl)benzyl)phthalazin-1(2H)-one;
4-(4-fluoro-3-(4-oxido-1-(2,2,2-trifluoroethyl)-1,4-azaphosphinan-4-yl)benzyl)phthalazin-1-(2H)-one;
4-[[4-fluoro-3-(4-methyl-4-oxo-1,4-azaphosphinane-1-carbonyl)phenyl]methyl]-2H-phthalazin-1-one;

4-[[4-fluoro-3-(4-ethyl-4-oxo-1,4-azaphosphinane-1-carbonyl)phenyl]methyl]-2H-phthalazin-1-one;

4-[[4-fluoro-3-(4-isopropyl-4-oxo-1,4-azaphosphinane-1-carbonyl)phenyl]methyl]-2H-phthalazin-1-one;

4-[[4-fluoro-3-(4-ethoxyl-4-oxo-1,4-azaphosphinane-1-carbonyl)phenyl]methyl]-2H-phthalazin-1-one;

4-(3-(1-cyclopropyl-4-oxido-1,4-azaphosphinan-4-yl)-4-fluorobenzyl)-7-fluorophthalazin-1(2H)-one;

4-(4-fluoro-3-(4-oxido-1-(pyrimidin-2-yl)-1,4-azaphosphinan-4-yl)benzyl)-7-fluorophthalazin-1(2H)-one;

(±)-4-[(3-(1-cyclopropyl-4-oxido-1,4-azaphosphinan-4-yl)-4-fluoro-1-phenyl)(hydroxymethyl)]phthalazin-1(2H)-one; and (±)-4-{[4-fluoro-3-(4-oxido-1-(pyrimidin-2-yl)-1,4-azaphosphinan-4-yl)phenyl)](hydroxymethyl)]-7-fluorophthalazin-1(2H)-one;

or a pharmaceutically acceptable salt or solvate thereof.

10. The compound of claim 1, wherein the compound is a compound of the formula (IV):

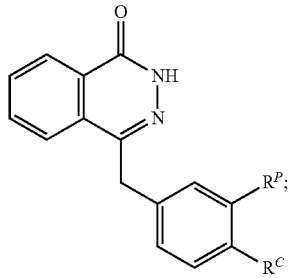

(IV)

wherein
$R^C$ is hydrogen, halo, —CF$_3$, unsubstituted C$_1$-C$_3$ alkyl or unsubstituted C$_1$-C$_3$ alkoxy;
$R^P$ is a moiety of the formula (Ia) or (Ib):

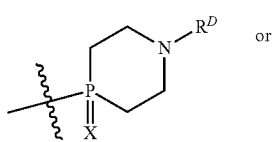

(Ia) or

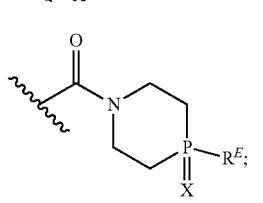

(Ib)

X is O;
$R^D$ is hydrogen, substituted or unsubstituted alkyl unsubstituted cycloalkyl, substituted or unsubstituted aryl, substituted or unsubstituted heteroaryl, —C(O)R$^4$, —C(=N—CN)NR$^8$R$^9$ or —C(O)NR$^5$R$^6$;
$R^4$ is unsubstituted alkyl, unsubstituted cycloalkyl, unsubstituted alkoxy, or substituted or unsubstituted heterocyclyl;
each $R^5$ and $R^6$ is independently hydrogen, unsubstituted alkyl or unsubstituted cycloalkyl;
each $R^8$ and $R^9$ is independently hydrogen, unsubstituted alkyl or unsubstituted cycloalkyl, or $R^8$ and $R^9$ are taken together with the nitrogen to which they are attached to form an unsubstituted heterocyclyl;
$R^E$ is unsubstituted alkyl, unsubstituted cycloalkyl, unsubstituted aryl, or —OR$^7$; and
$R^7$ is unsubstituted alkyl or unsubstituted cycloalkyl;
wherein the substituted alkyl, the substituted cycloalkyl, the substituted alkoxy, the substituted aryl, the substituted heteroaryl, and the substituted heterocyclyl are independently substituted by one, two, three, or more substituents, wherein the substituents are independently cyano, halo, haloalkyl, alkyl alkylcarbonyl, cycloalkyl or aryl; wherein said alkyl substituents are optionally substituted with hydroxyl, or a pharmaceutically acceptable salt or solvate thereof.

11. The compound of claim 10, wherein the compound is of the formula (IVa):

(IVa)

or a pharmaceutically acceptable salt or solvate thereof.

12. A compound of the formula (IVb):

(IVb)

wherein:
$R^C$ is hydrogen, halo, —CF$_3$, unsubstituted C$_1$-C$_3$ alkyl or unsubstituted C$_1$-C$_3$ alkoxy;
$R^E$ is unsubstituted alkyl, unsubstituted cycloalkyl, unsubstituted aryl, or —OR$^7$; and
$R^7$ is an unsubstituted alkyl or unsubstituted cycloalkyl;
or a pharmaceutically acceptable salt or solvate thereof.

13. The compound of claim 1, wherein the compound is a compound of the formula (V):

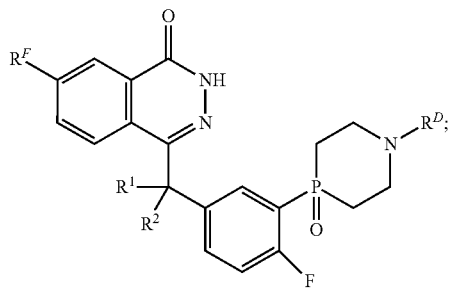

(V)

wherein
each $R^1$ and $R^2$ is independently hydrogen, halo, hydroxy, unsubstituted $C_1$-$C_3$ alkyl or unsubstituted $C_1$-$C_3$ alkoxy;
$R^D$ is hydrogen, substituted or unsubstituted alkyl, unsubstituted cycloalkyl, substituted or unsubstituted aryl, substituted or unsubstituted heteroaryl; and
$R^F$ is hydrogen, halo, —$CF_3$, unsubstituted $C_1$-$C_3$ alkyl or unsubstituted $C_1$-$C_3$ alkoxy;
wherein the substituted alkyl, the substituted aryl, the substituted heteroaryl, and the substituted heterocyclyl are independently substituted by one, two, three, or more substituents, wherein the substituents are independently cyano, halo, haloalkyl, alkyl, alkylcarbonyl, cycloalkyl, or aryl; wherein said alkyl substituents are optionally substituted with hydroxyl,
or a pharmaceutically acceptable salt or solvate thereof.

14. The compound of claim 13, or a pharmaceutically acceptable salt or solvate thereof, wherein $R^D$ is cyclopropyl or 2-pyrimidinyl.

15. A pharmaceutical composition comprising a compound of claim 1 or a pharmaceutically acceptable salt or solvate thereof, and a pharmaceutically acceptable carrier.

16. A pharmaceutical composition, comprising a compound of claim 9, or a pharmaceutically acceptable salt or solvate thereof, and a pharmaceutically acceptable carrier.

17. A pharmaceutical composition, comprising a compound of claim 12, or a pharmaceutically acceptable salt or solvate thereof, and a pharmaceutically acceptable carrier.

18. A compound of the formula (V):

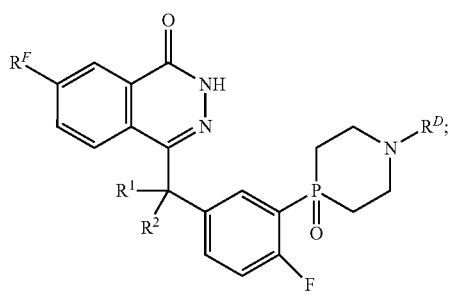

(V)

wherein
each $R^1$ and $R^2$ is independently hydrogen, halo, hydroxy, unsubstituted $C_1$-$C_3$ alkyl or unsubstituted $C_1$-$C_3$ alkoxy;

$R^D$ is selected from the group consisting of:

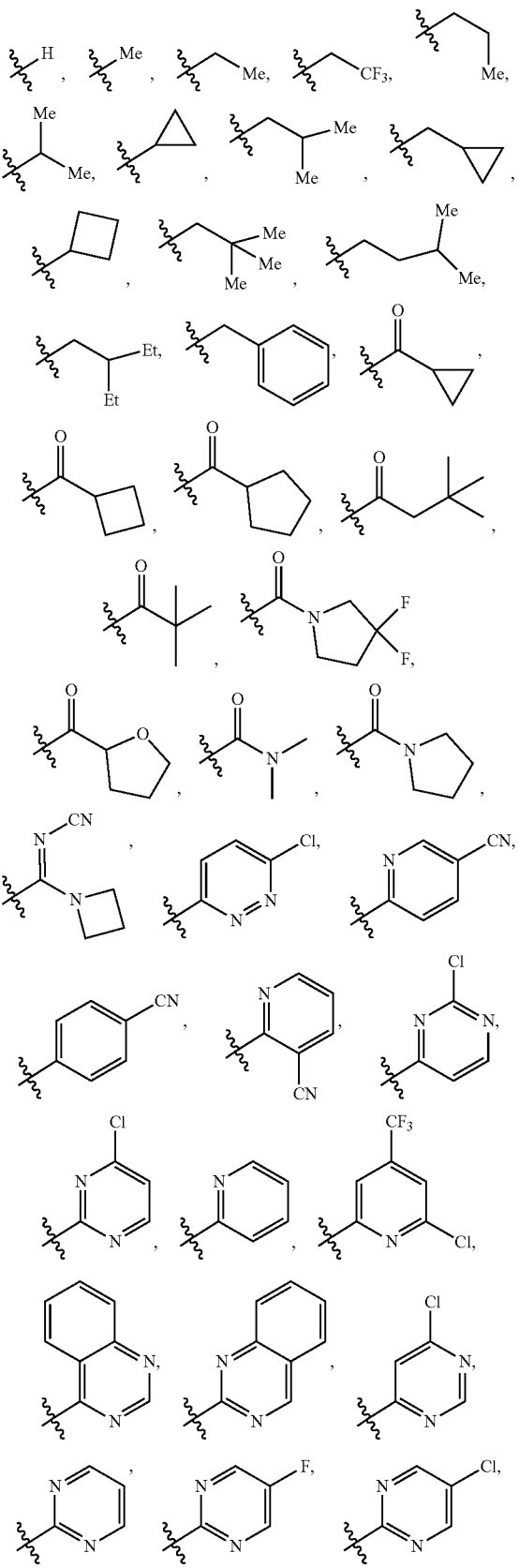

91

-continued

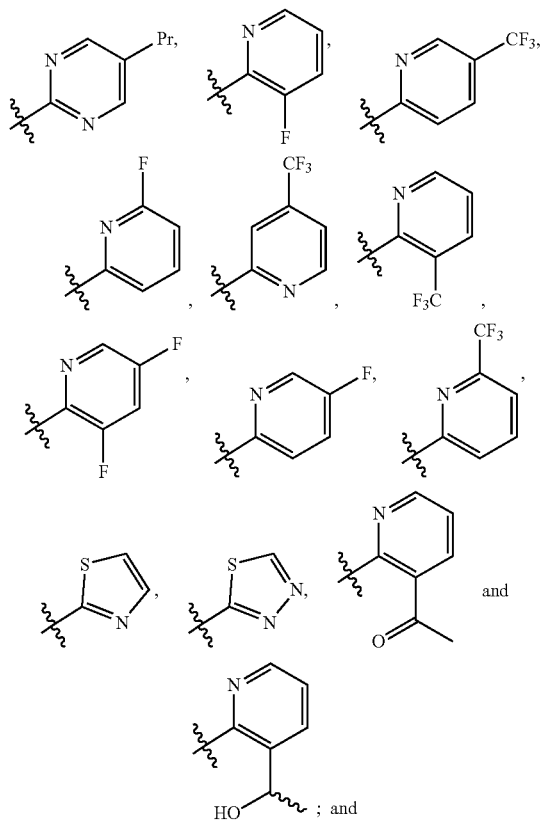

$R^F$ is hydrogen, halo, —CF$_3$, unsubstituted C$_1$-C$_3$ alkyl or unsubstituted C$_1$-C$_3$ alkoxy, or a pharmaceutically acceptable salt or solvate thereof.

19. A pharmaceutical composition, comprising a compound of claim 18, or a pharmaceutically acceptable salt or solvate thereof, and a pharmaceutically acceptable carrier.

20. The compound of claim 1, wherein the compound is selected from the group consisting of:

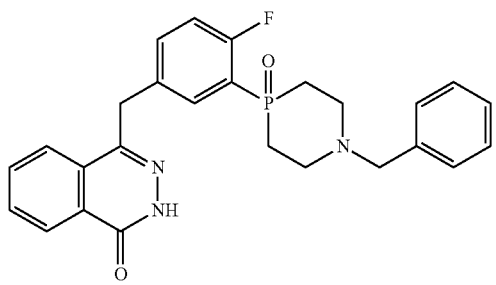

,

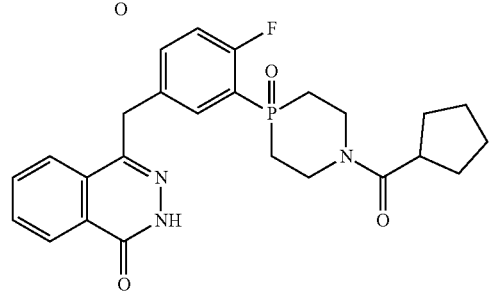

,

92

-continued

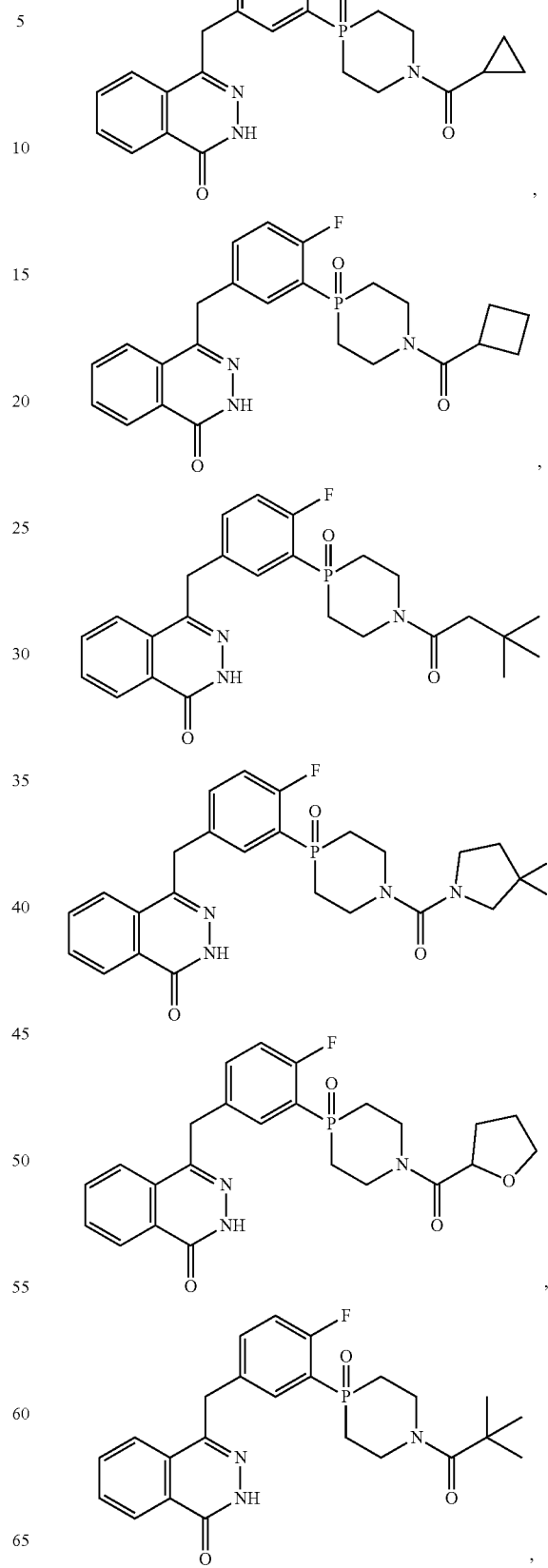

,

93
-continued
94
-continued
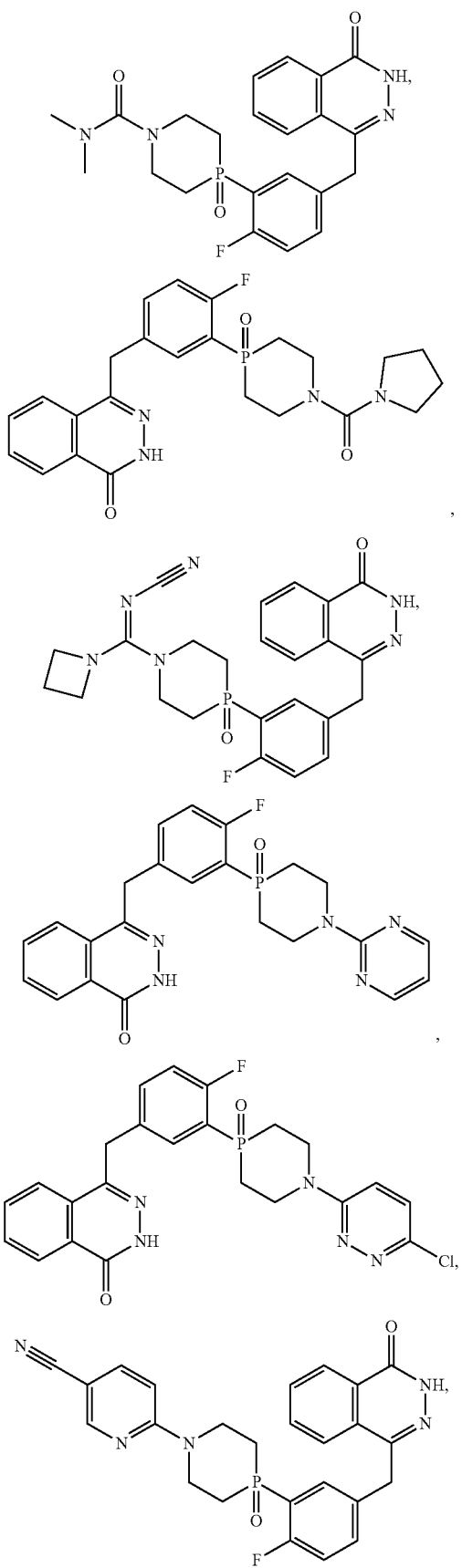
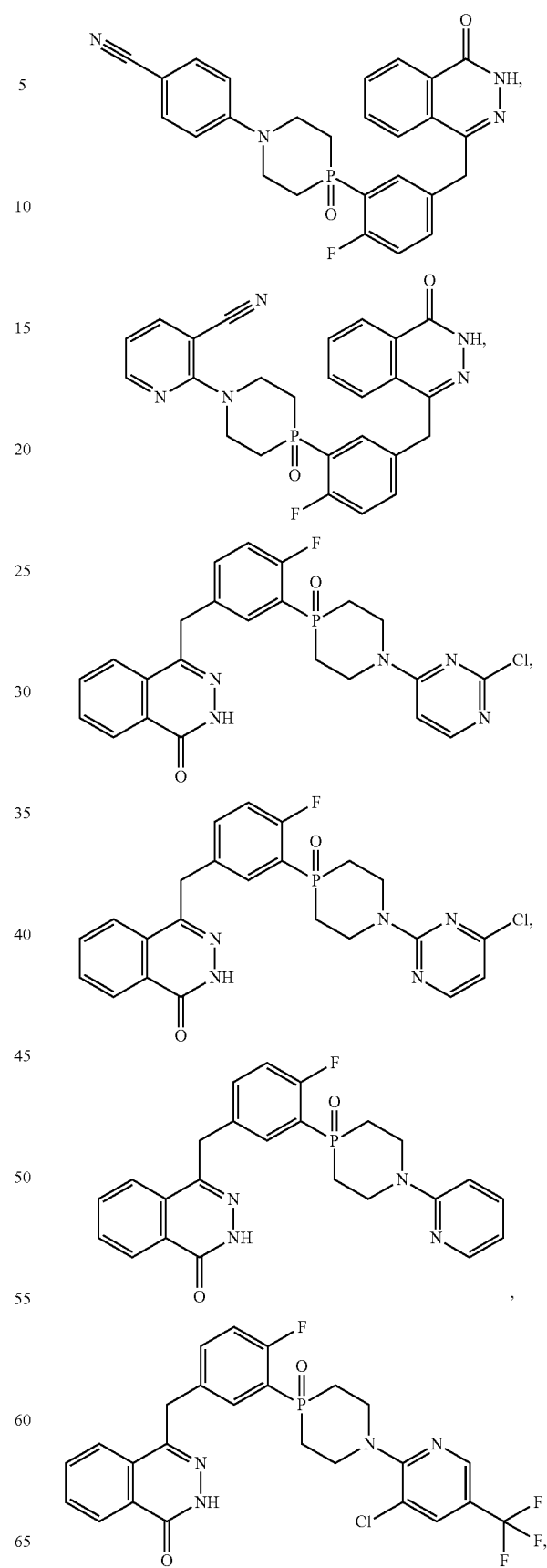

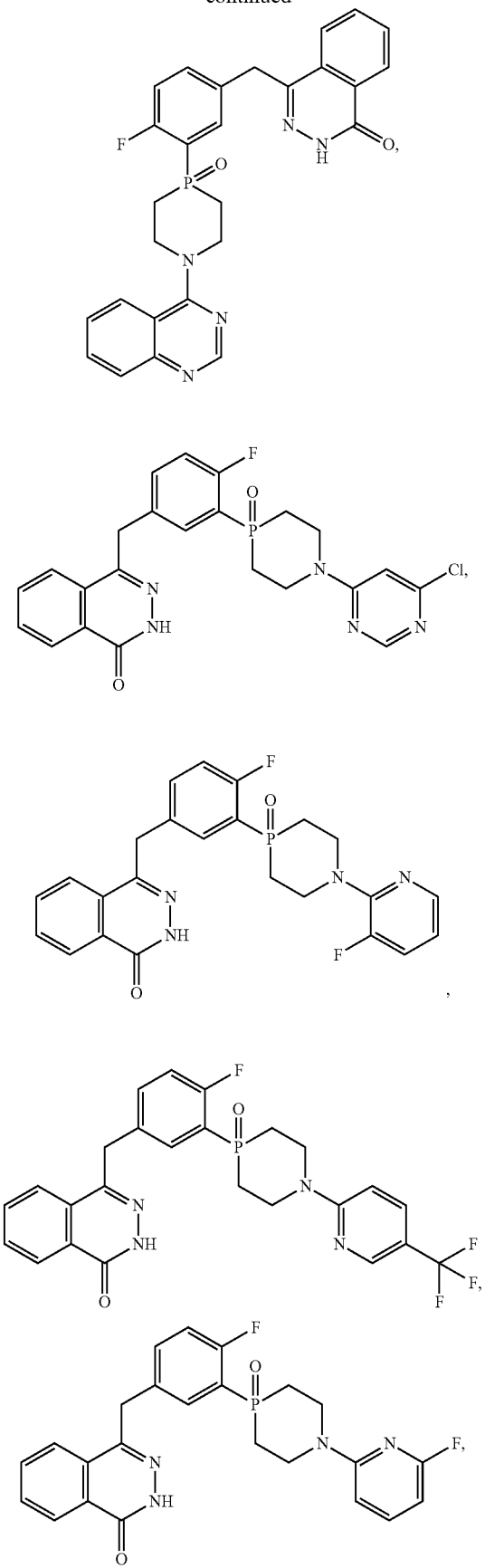

97
-continued
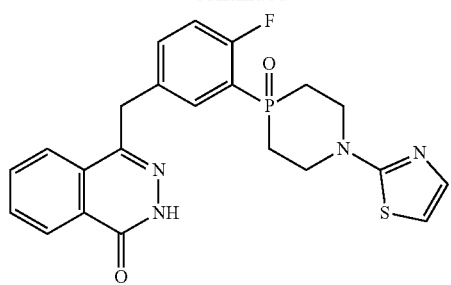
,
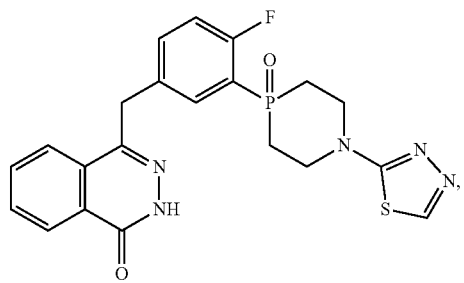
,
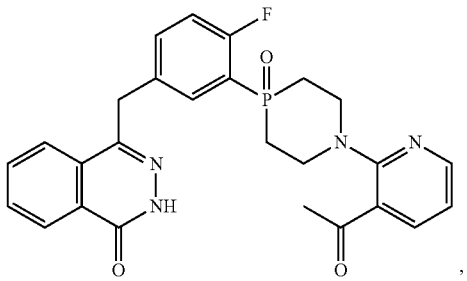
,
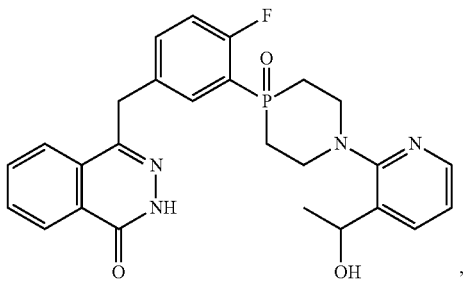
,
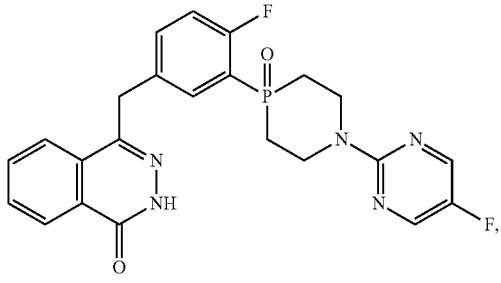
,
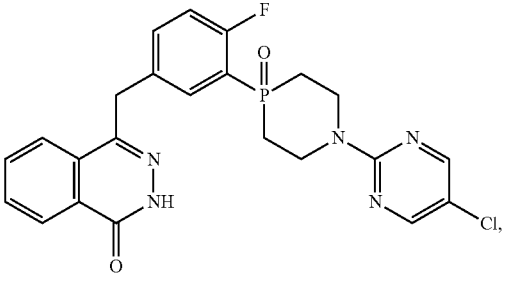
,
98
-continued
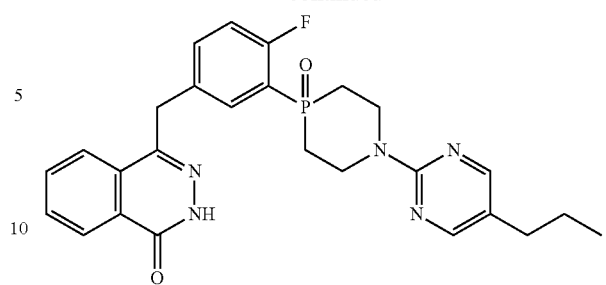
,
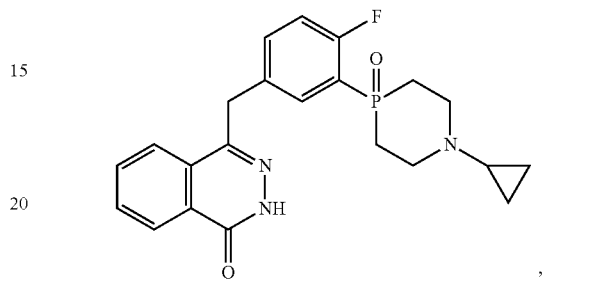
,
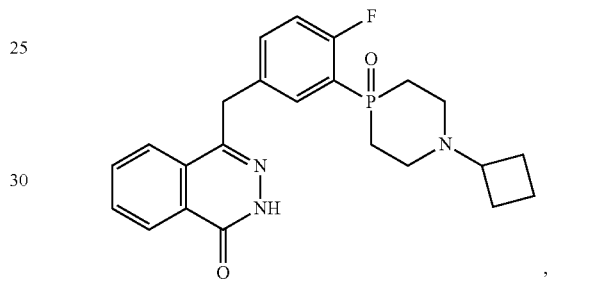
,
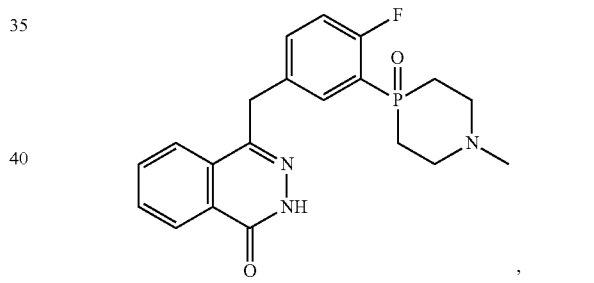
,
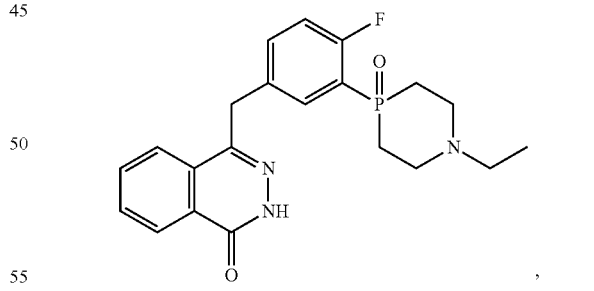
,
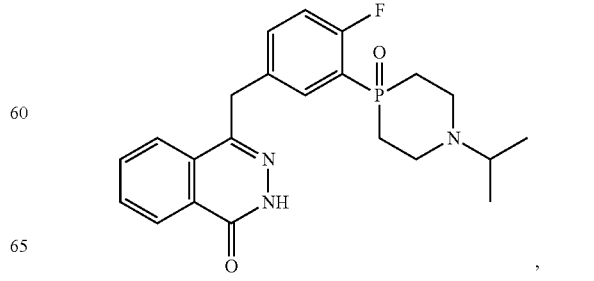
,

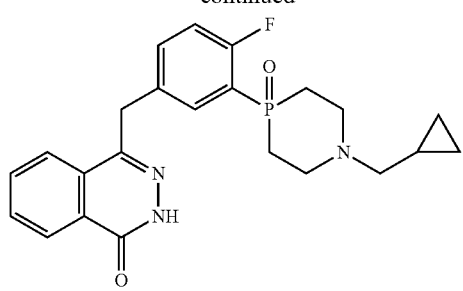
,
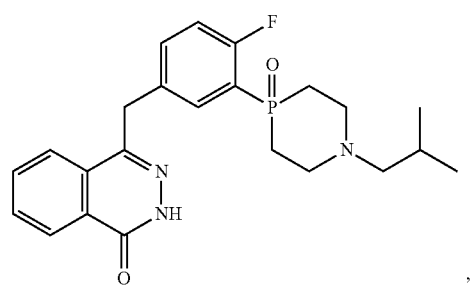
,
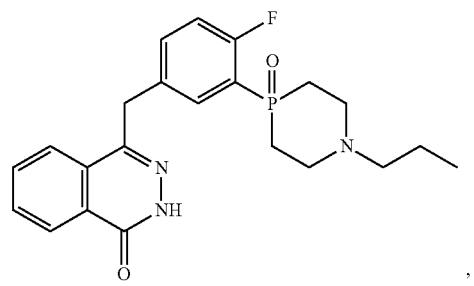
,
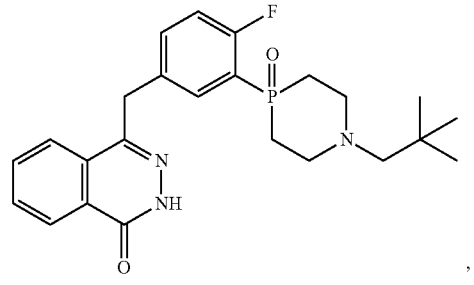
,
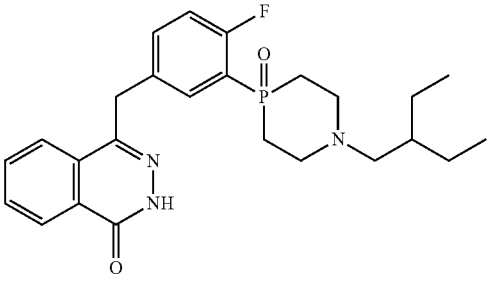
,
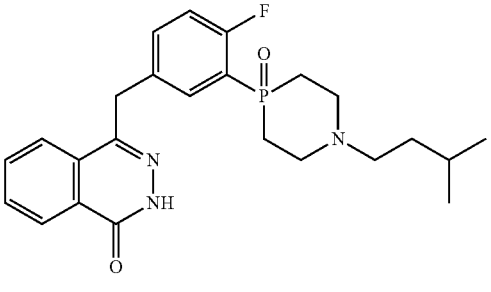
,
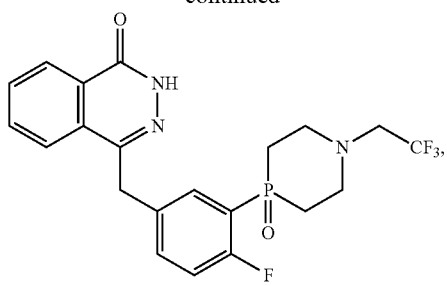
,
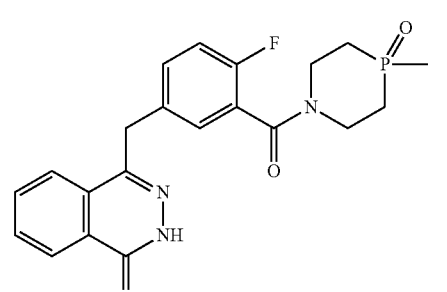
,
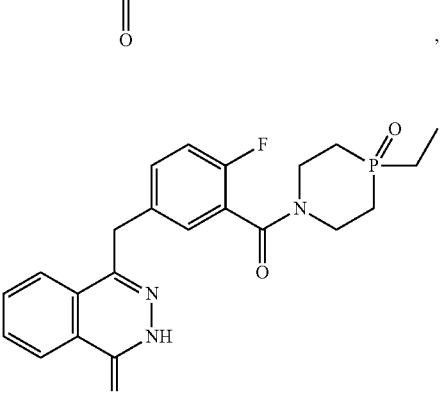
,
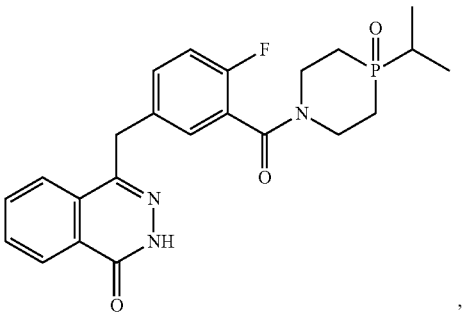
,
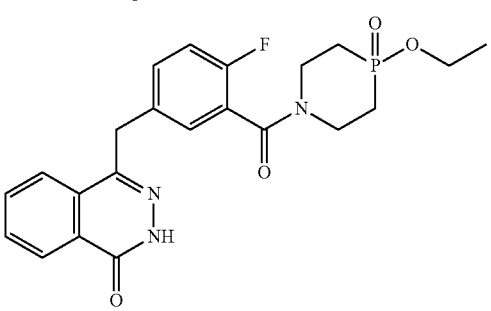
,

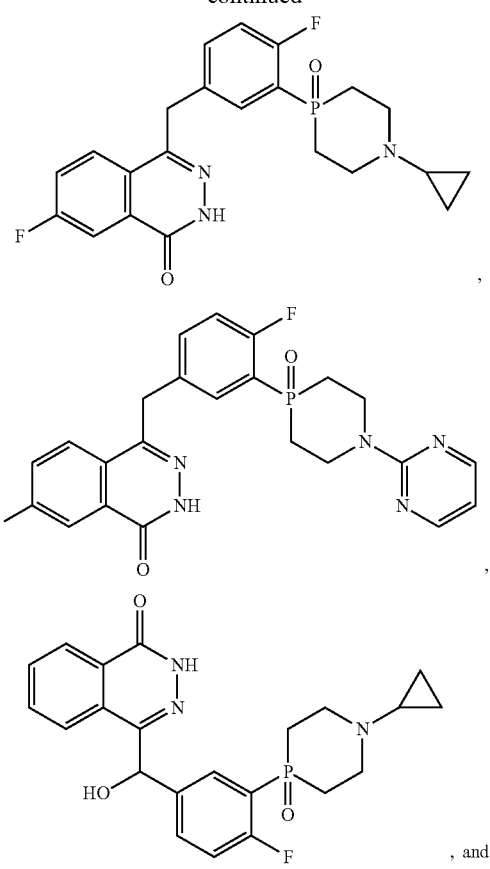

21. The compound of claim 18, wherein the compound is or a pharmaceutically acceptable salt or solvate thereof.

22. A pharmaceutical composition, comprising a B compound of claim 20, and a pharmaceutically acceptable carrier.

23. A pharmaceutical composition, comprising a compound of claim 21, or a pharmaceutically acceptable salt or solvate thereof, and a pharmaceutically acceptable carrier.

* * * * *